United States Patent
Labeeuw et al.

Patent Number: 5,939,449
Date of Patent: Aug. 17, 1999

[54] SUBSTITUTED 1-PHENYL-3-PYRAZOLECARBOXAMIDES ACTIVE ON NEUROTENSIN RECEPTORS, THEIR PREPARATION AND PHARMACEUTICAL COMPOSITIONS CONTAINING THEM

[75] Inventors: Bernard Labeeuw, Montpellier; Danielle Gully, Saubens; Francis Jeanjean, Valflaunes; Jean-Charles Molimard, St. Gely Du Fesc; Robert Boigegrain, Assas, all of France

[73] Assignee: Sanofi, Paris, France

[21] Appl. No.: 08/977,496

[22] Filed: Nov. 24, 1997

Related U.S. Application Data

[62] Division of application No. 08/630,761, Apr. 10, 1996, Pat. No. 5,723,483.

[30] Foreign Application Priority Data

Apr. 11, 1995 [FR] France .................................. 96 04350

[51] Int. Cl.$^6$ ...................... A61K 31/415; C07C 233/63; C07C 235/40; C07D 231/12
[52] U.S. Cl. .......................... 514/406; 514/210; 514/396; 514/399; 514/402; 514/408; 514/428; 540/362; 548/335.5; 548/341.1; 548/347.1; 548/354.1; 548/518; 548/521; 548/962; 548/356.1; 564/171; 564/181
[58] Field of Search ..................................... 514/406, 210, 514/396, 399, 402, 408, 428; 540/362; 548/335.5, 341.1, 347.1, 354.1, 518, 521, 962, 356.1; 564/171, 181

[56] References Cited

U.S. PATENT DOCUMENTS

| | | | |
|---|---|---|---|
| 5,420,141 | 5/1995 | Boigegrain et al. | 514/314 |
| 5,502,059 | 3/1996 | Labeeuw et al. | 514/296 |
| 5,585,497 | 12/1996 | Labeeuw et al. | 548/374.1 |
| 5,616,592 | 4/1997 | Boigegrain et al. | 514/314 |

OTHER PUBLICATIONS

Data Base Crossfire, BRN=509890, & Justus Liebigs AA. Chem., vol. 120, (1861) p. 126.
Database Crossfire, BRN=1841460, & J. Chem. Soc., p. 4060(1964).
Database Crossfire, BRN=3297648 & Andre 'Dissertation', (1909), Bonn p. 27.
Database Crossfire, BRN=3257569, & Auden Dissertation, (1897) Tuebingen, p. 17.
Database Crossfire, BRN=3312692, & Chem. Ber., vol. 62,(1929) p. 2566.
Database Cross Fire, BRN=1818200, & Helv. Chim. Acta, pp. 793–797, vol. 43,(1960).
Database Crossfire, BRN=910233, & Chem. Ber., vol. 21,(1988) p. 3409.
Database Crossfire, BRN=1818353, & Indian J. Chem., vol. 1,(1963) pp. 247–249.
Database Crossfire, BRN=1818417, & US–A–4 105 766 (Sterling Drug) (1978).
Database Cross Fire, BRN—1818415, & US–A–4 105 766 (Sterling Drug) (1978).
Database Crossfire, BRN=1819156, & Chem Ber., vol. 96,(1963)pp. 184–187.
Database Crossfire, BRN=3274365, & Chem. Ber., vol. 18(1885) p. 3175.
Database Crossfire, BRN=3285701, & Chem. Ber., vol. 21(1888), p. 3223.
Database Crossfire, BRN=3293381, & ZH Obshch. Khim., vol. 4(1934) pp. 728–731.
Database Crossfire, BRN=3330098, & J Amer. Chem. Soc., vol. 45,(1923) p. 1491.
Database Crossfire, BRN=3285692, & Recl. Trav. Chim. Pays–Bas, vol. 24,(1905), p. 206.
Database Crossfire, BRN=387378, & Chem. Ber., vol. 86,(1953), pp. 1073–1075.
Database Crossfire, BRN=1818729, & Chem. Ber., vol. 85,(1952) pp. 760–773.
Database Crossfire, BRN=1841461, & J. Amer. Chem. Soc., vol. 66,(1944) pp. 1851–1854.
Database Crossfire, BRN—514779, & Helv. Chim. Acta, vol. 17,(1934) pp. 1416–1417.
Database Crossfire, BRN=776989, & Am. Chem. J., vol. 37,(1907), p. 365.
Database Crossfire,BRN=3274303, & Chem. Ber., vol. 18,(1885) p. 2193.
Database Crossfire, BRN=3283626, & Chem. Ber., vol. 18, (1882) p. 2193.
Database Crossfire, BRN=1818557, Indian J. Chem., vol. 1,(1963), pp. 247–250.
Gully et al., "Biochemical and Pharmacological Profile of a Patent and Selective Nonpeptide Antagonist of the Neurotensin Receptor", *Proc. Natl. Acad. Sci.*, USA, 90, pp. 65–69 (Jan. 1993).

Primary Examiner—Deborah C. Lambkin
Assistant Examiner—Jane C. Oswecki
Attorney, Agent, or Firm—Bacon & Thomas

[57] ABSTRACT

The invention relates to compounds of the formula:

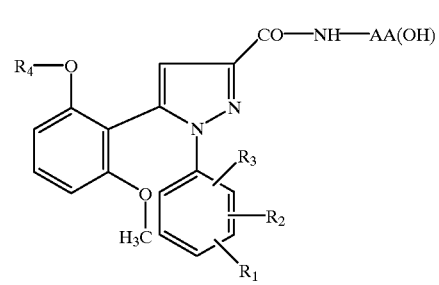

(I)

The compounds have great affinity for the neurotensin receptors.

14 Claims, No Drawings

SUBSTITUTED 1-PHENYL-3-PYRAZOLECARBOXAMIDES ACTIVE ON NEUROTENSIN RECEPTORS, THEIR PREPARATION AND PHARMACEUTICAL COMPOSITIONS CONTAINING THEM

This application is a Division of application Ser. No. 08/630,761, filed on Apr. 10, 1996, now U.S. Pat. No. 5,723,483.

The present invention relates to new substituted 1-phenyl-3-pyrazolecarboxamides having a great affinity for human neurotensin receptors, to a process for preparing them and to pharmaceutical compositions containing them as active principles.

The first synthetic non-peptide potential medicinal products capable of binding to neutotensin receptors have been described in EP-0,477,049. They are amides of 3-pyrazolecarboxylic acid, variously substituted with amino acids, which displace iodinated neurotensin from its receptor, at doses of less than one micromole, on guinea pig brain membranes. This series led to the development of a compound, 2-[(1-(7-chloro-4-quinolyl)-5-(2,6-dimethoxyphenyl)-3-pyrazolyl)carbonylamino]-2-adamantanecarboxylic acid, SR 48692, endowed with potent and selective neurotensin-antagonist activity (D. Gully et al., Proc. Natl. Acad. Sci. U.S.A., 1993, 90, 65–69).

The feature of the series of products described in EP-0,477,049 is the presence at position 1 of the pyrazole ring of, in particular, a phenyl, naphthyl or 4-quinolyl group, substituted or unsubstituted. More especially, SR 48692 possesses a 7-chloro-4-quinolyl group in position 1 of the pyrazole. The products described in this document having a 1-naphthyl or 4-chloro-1-naphthyl group in position 1 of the pyrazole ring have an extremely high affinity for the guinea pig neurotensin receptor, since their $IC_{50}$ is of the order of 1 to 10 nanomoles, whereas their affinity for the human receptor is lower since their $IC_{50}$ is from 10 to 100 nmol.

It has now been found that, by substituting the phenyl group of 1-phenyl-3-pyrazolecarboxamide compounds with particular groups, the affinity for neurotensin receptors is increased, and more especially the affinity for human neurotensin receptors is increased.

In addition, the compounds according to the present invention show in vivo a broader spectrum of activity than the compounds described in EP-0,477,049 as antagonists of the neurotensin receptors.

Thus, the present invention relates, according to one of its aspects, to new substituted 1-phenyl-3-pyrazolecarboxamides of formula:

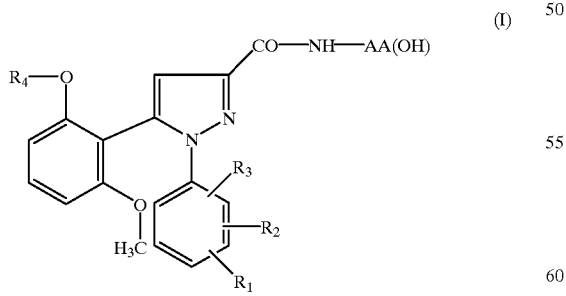

(I)

in which:

$R_1$ represents a group chosen from:
—T—CN;
—C(NH$_2$)=NOH;
—(=NOH)NH(CH$_2$)$_r$NR$_5$R$_6$;
—T—C(NR$_{12}$R$_{13}$)=NR$_{14}$;
—C(NH$_2$)=NO(CH$_2$)$_r$NR$_5$R$_6$;
—T—CONR$_a$R$_b$;
—T—CONR$_7$R$_c$;
—Y—CO$_2$R$_7$;
—OR$_d$;
—T—NR$_5$R$_6$, on condition that $R_5$ and $R_6$ do not simultaneously represent hydrogen when T represents a direct bond;
—T—N(R$_7$)COR$_e$;
—SO$_2$NR$_a$R$_b$;
—T—N(R$_7$)SO$_2$R'$_7$;
—T—NR$_{27}$R$_{28}$;

—NR$_a$R$_b$ represents a group chosen from:
—NR$_5$R$_6$; —NR$_9$(CH$_2$)$_s$CR$_7$R$_8$(CH$_2$)$_t$NR$_5$R$_6$; —NR$_{21}$(CH$_2$)$_s$CR$_7$R$_8$(CH$_2$)$_t$$^{\oplus}$NR$_{22}$R$_{23}$R$_{24}$Q$^{\ominus}$

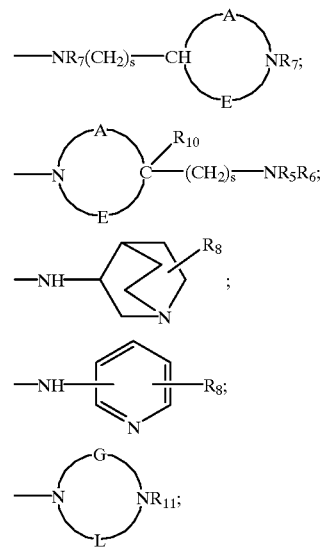

—NR$_7$(CH$_2$)$_q$CN; —NR$_7$(CH$_2$)$_q$C(NR$_{12}$R$_{13}$)=NR$_{14}$;
—NR$_7$(CH$_2$)$_q$CONH$_2$; —NR$_7$(CH$_2$)$_q$CO$_2$R$_7$;
—NR$_{21}$(CH$_2$)$_s$CR$_7$R$_8$(CH$_2$)$_t$NR$_{25}$R$_{26}$;

$R_c$ represents a group chosen from:
—X—OR$_7$; —CHR$_{20}$CO$_2$R$_7$; —(CH$_2$)$_4$CH(NH$_2$)CO$_2$R$_7$;

$R_d$ represents a group chosen from:
—X—NR$_5$R$_6$; —Y—CONR$_5$R$_6$; —Y—CO$_2$R$_7$;
—Y—SO$_2$NR$_5$R$_6$;

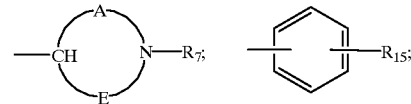

$R_e$ represents a group chosen from:
—R$_{16}$; —Y—NR$_5$R$_6$; —Y—NHCOR$_{16}$; —CH(R$_{17}$)NR$_5$R$_6$; —Y—$^{\oplus}$NR$_{22}$R$_{23}$R$_{24}$Q$^{\ominus}$

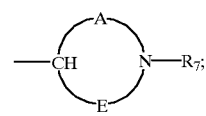

—(CH$_2$)$_q$CN; —(CH$_2$)$_q$C(NR$_{12}$R$_{13}$)=NR$_{14}$;
—NR$_{18}$R$_{19}$;

$R_2$ and $R_3$ each independently represent hydrogen, a $(C_1-C_6)$alkyl, a $(C_3-C_8)$cycloalkylmethyl, a $(C_3-C_8)$ cycloalkyl, a halogen, a nitro, a trifluoromethyl, a group —$OR_4$, a group —$NR_5R_6$, a 1-pyrrolyl, a cyano, a carbamoyl;

or $R_2$ and $R_3$ together constitute a trimethylene, tetramethylene or pentamethylene group;

$R_4$ represents hydrogen; a $(C_1-C_6)$alkyl; a $(C_3-C_4)$ alkenyl; a $(C_3-C_8)$cycloalkyl; a $(C_3-C_8)$ cycloalkylmethyl; a $(C_1-C_4)$alkoxy$(C_1-C_4)$alkylene; a benzyl;

$R_5$ and $R_6$ each independently represent a hydrogen, a $(C_1-C_6)$alkyl; a $(C_3-C_8)$alkenyl; a $(C_3-C_8)$ cycloalkylmethyl; a benzyl; or $R_5$ and $R_6$, together with the nitrogen atom to which they are attached, represent a heterocycle chosen from: pyrrolidine, piperidine, morpholine, thiomorpholine, piperazine substituted at position 4 with $R_9$, aziridine, azetidine and perhydroazepine;

$R'_5$ and $R'_6$ each independently represent a hydrogen or a $(C_1-C_6)$alkyl; or alternatively, $R'_5$ and $R'_6$, together with the nitrogen atom to which they are attached, represent a heterocycle chosen from: pyrrolidine, piperidine, morpholine, thiomorpholine and piperazine which is unsubstituted or substituted at position 4 with a $(C_1-C_6)$alkyl;

$R'_7$ represents a $(C_1-C_4)$alkyl; a phenyl which is unsubstituted or substituted one or more times with a $(C_1-C_4)$ alkyl; a group —X—$NR_5R_6$;

$R_7$ represents a hydrogen, a $(C_1-C_4)$alkyl or a benzyl;

$R_8$ represents a hydrogen, a $(C_1-C_4)$alkyl, a hydroxyl, or $R_7$ and $R_8$, together with the carbon atom to which they are attached, constitute a $(C_3-C_5)$cycloalkane;

$R_9$ represents hydrogen, a $(C_1-C_4)$alkyl, a benzyl, a group —X—OH or a group —X—$NR'_5R'_6$, a $(C_3-C_8)$ alkenyl;

$R_{10}$ represents a hydrogen, a $(C_1-C_4)$alkyl, a benzyl, a carbamoyl, a cyano;

$R_{11}$ represents a hydrogen, a $(C_1-C_4)$alkyl, a group —X—OH, a group —X—$NR'_5R'_6$;

$R_{12}$ and $R_{13}$ each independently represent a hydrogen or a $(C_1-C_4)$alkyl;

$R_{14}$ represents hydrogen, $R_{14}$ can, in addition, represent a $(C_1-C_4)$alkyl when $R_{12}$ represents hydrogen and $R_{13}$ represents a $(C_1-C_4)$alkyl;

or $R_{13}$ and $R_{14}$ together represent a group Z;

$R_{15}$ represents hydrogen, a $(C_1-C_4)$alkyl, a group —$(CH_2)_s NR_5R_6$;

$R_{16}$ represents hydrogen, a $(C_1-C_8)$alkyl, a $(C_3-C_8)$ cycloalkyl, a phenyl, a 2-piperidyl, a 3-piperidyl, a 4-piperidyl;

$R_{17}$ represents a $(C_1-C_6)$alkyl, a phenyl, a benzyl, a hydroxy$(C_1-C_4)$alkyl, an amino$(C_1-C_4)$alkyl;

$R_{18}$ and $R_{19}$ each independently represent a hydrogen, a $(C_1-C_4)$alkyl; $R_{18}$ can, in addition, represent a group —$(CH_2)_q-NR_5R_6$;

or $R_{18}$ and $R_{19}$, together with the nitrogen atom to which they are attached, represent a heterocycle chosen from: pyrrolidine, piperidine, morpholine, thiomorpholine, piperazine substituted at position 4 with $R_9$;

$R_{20}$ represents hydrogen, a $(C_1-C_4)$alkyl, a benzyl, a hydroxyphenylmethyl, preferably a 4-hydroxyphenylmethyl, a hydroxy$(C_1-C_4)$alkyl, a mercapto$(C_1-C_4)$alkyl; a —$(CH_2)_3$—NH—C(=NH) $NH_2$ group, a —$(CH_2)_4NH_2$ group, a group —$CH_2$— Im in which Im represents a 4-imidazolyl;

$R_{21}$ represents a $(C_1-C_4)$alkyl, an allyl or a benzyl;

$R_{22}$ and $R_{23}$ each independently represent a $(C_1-C_6)$alkyl; or alternatively $R_{22}$ and $R_{23}$, together with the nitrogen atom to which they are attached, represent a heterocycle chosen from: pyrrolidine, piperidine, morpholine and perhydroazepine;

$R_{24}$ represents a $(C_1-C_4)$alkyl, a benzyl, an allyl, a hydroxy$(C_1-C_4)$alkyl, a $(C_1-C_4)$alkoxy$(C_1-C_4)$alkyl;

$Q^\ominus$ represents an anion;

$R_{25}$ represents hydrogen or a $(C_1-C_6)$alkyl;

$R_{26}$ represents a $(C_1-C_4)$alkoxycarbonyl, a benzyloxycarbonyl; a $(C_1-C_4)$alkylcarbonyl;

$R_{27}$ represents a hydrogen; a $(C_1-C_4)$alkyl, a $(C_1-C_4)$ alkylcarbonyl; a group —CO—$(CH_2)_r$—OH; a group $SO_2R'_7$;

$R_{28}$ represents a group —X—$NR_5R_6$;

s=0 to 3;

t=0 to 3, on the condition that (s+t), in a same group, is greater than or equal to 1;

r=2 to 5;

q=1 to 5;

T represents a direct bond or $(C_1-C_7)$alkylene;

X represents a $(C_2-C_7)$alkylene;

Y represents a $(C_1-C_7)$alkylene;

Z represents a $(C_2-C_6)$alkylene;

the bivalent radicals A and E, together with the carbon atom and the nitrogen atom to which they are attached, constitute a saturated 4- to 7-membered heterocycle which can, in addition, be substituted with one or more $(C_1-C_4)$alkyls;

the bivalent radicals G and L, together with the nitrogen atoms to which they are attached, constitute a piperazine or imidazolidine or imidazoline ring, the said rings being optionally substituted on the carbon atoms with one or more $(C_1-C_4)$alkyls;

the group —NH—AA(OH) represents the residue of an amino acid:

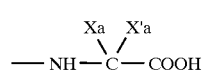

where $X_a$ is hydrogen and $X'_a$ is hydrogen, a $(C_1-C_5)$alkyl or a non-aromatic $C_3-C_{15}$ carbocyclic radical; or alternatively, $X_a$ and $X'_a$, together with the carbon atom to which they are attached, form a non-aromatic $C_3-C_{15}$ carbocycle;

their salts and their quaternary ammonium salts formed with acyclic or cyclic tertiary amines and their solvates.

When a compound according to the invention comprises one or more asymmetric carbon atoms, each of the optical isomers forms part of the invention, as does the racemic form.

When a compound according to the invention possesses several tautomeric forms, each of these forms part of the invention. This is the case, in particular, when the substituent $R_1$ contains a substituted amidine group —$C(NR_{12}R_{13})$ =$NR_{14}$.

When the group —NH(AA)OH represents the residue of a cycloaliphatic amino acid, the amino or aminomethyl groups may be in the endo position or in the exo position with respect to the ring system; in both cases, the compounds of formula (I) form part of the invention.

According to the present invention, alkyl or alkylene is understood to mean an unbranched or branched alkyl or alkylene qualified by the number of carbon atoms it contains; halogen is understood to mean a chlorine, bromine, fluorine or iodine atom.

Non-aromatic $C_3$–$C_{15}$ carbocyclic radicals comprise saturated or unsaturated, fused or bridged mono- or polycyclic radicals, optionally terpenic. These radicals are optionally mono- or polysubstituted with a $C_1$–$C_4$ alkyl.

Monocyclic radicals include cycloalkyls, for example cyclopropyl, cyclopentyl, cyclohexyl, cycloheptyl, cyclooctyl, cyclododecyl.

In the above residue of the amino acid, when $X_a$ and $X'_a$, together with the carbon atom to which they are attached, form a non-aromatic $C_3$–$C_{15}$ carbocycle, the said carbocycle is as defined for the corresponding radicals above.

Among polycyclic non-aromatic carbocycles, adamantane, bicyclo[3.3.1]nonane and norbornane are the preferred members. The radical corresponding to adamantane may be 1-adamantyl when $X_a$ is hydrogen, or 2-adamantylidene when $X_a$ and $X'_a$, together with the carbon atom to which they are attached, form a carbocycle.

Among monocyclic non-aromatic carbocycles, cyclopentane and cyclohexane are especially preferred.

The salts of the compounds of the invention can be internal salts or alternatively salts with alkali metals, preferably sodium or potassium, and alkaline-earth metals, preferably calcium, and with organic bases such as diethylamine, tromethamine, meglumine (N-methyl-D-glucamine), lysine, arginine, histidine, choline or diethanolamine, or optically pure organic bases such as α-methylbenzylamine.

The salts of the compounds of formula (I) according to the present invention also comprise those with inorganic or organic acids which permit an appropriate separation or crystallization of the compounds of formula I, such as picric acid, oxalic acid or an optically active acid, for example a mandelic acid or a camphorsulphonic acid, and preferably those which form pharmaceutically acceptable salts such as the hydrochloride, acetate, hydrogen sulphate, dihydrogen phosphate, methanesulphonate, maleate, fumarate, 2-naphthalenesulphonate, isethionate, benzenesulphonate, para-toluenesulphonate, tartrate, citrate or edisilate.

The quaternary ammonium salts with acyclic or cyclic tertiary amines are formed by substitution of the amine with a ($C_1$–$C_4$)alkyl, a benzyl, an allyl, a hydroxy($C_1$–$C_4$)alkyl or a ($C_1$–$C_4$)alkoxy($C_1$–$C_4$)alkylene; the anion preferably being a pharmaceutically acceptable anion.

Advantageously, the invention relates to compounds of formula (Ip):

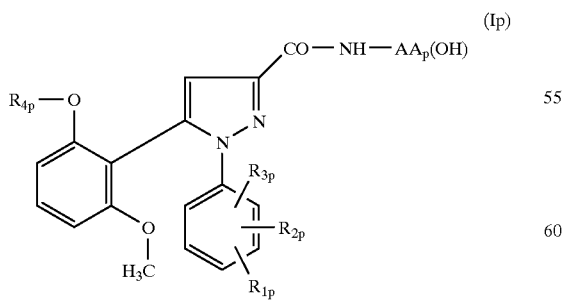

(Ip)

in which:

$R_1p$ represents a group chosen from:
—T—CN;
—C(NH$_2$)=NOH;
—C(=NOH)NH(CH$_2$)$_r$NR$_5$R$_6$;
—T—C(NR$_{12}$R$_{13}$)=NR$_{14}$;
—C(NH$_2$)=NO(CH$_2$)$_r$NR$_5$R$_6$;
—T—CONR$_a$R$_b$;
—T—CONR$_7$R$_c$;
—Y—CO$_2$R$_7$;
—OR$_d$;
—T—NR$_5$R$_6$, on condition that $R_5$ and $R_6$ do not simultaneously represent hydrogen when T represents a direct bond;
—T—N(R$_7$)COR$_e$;
—SO$_2$NR$_a$R$_b$;
—T—N(R$_7$)SO$_2$R'$_7$;

—NR$_a$R$_b$ represents a group chosen from:
—NR$_5$R$_6$; —NR$_9$(CH$_2$)$_s$CR$_7$R$_8$(CH$_2$)$_t$NR$_5$R$_6$;

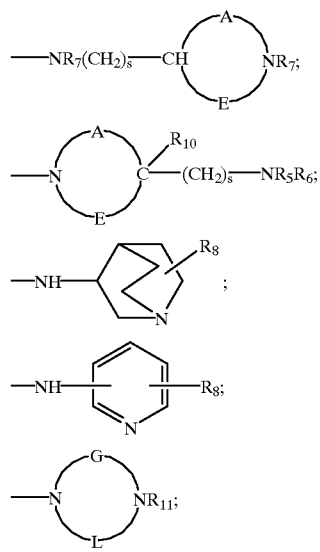

—NR$_7$(CH$_2$)$_q$CN; —NR$_7$(CH$_2$)$_q$C(NR$_{12}$R$_{13}$)=NR$_{14}$;

$R_c$ represents a group chosen from:
—X—OR$_7$; —CHR$_{20}$CO$_2$R$_7$; —(CH$_2$)$_4$CH(NH$_2$)CO$_2$R$_7$;

$R_d$ represents a group chosen from:
—X—NR$_5$R$_6$; —Y—CONR$_5$R$_6$; —Y—CO$_2$R$_7$; —Y—SO$_2$NR$_5$R$_6$;

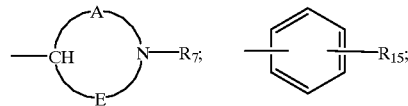

$R_e$ represents a group chosen from:
—R$_{16}$; —Y—NR$_5$R$_6$; —Y—NHCOR$_{16}$; —CH(R$_{17}$)NR$_5$R$_6$;

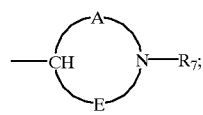

—(CH$_2$)$_q$CN; —(CH$_2$)$_q$C(NR$_{12}$R$_{13}$)=NR$_{14}$;
—NR$_{18}$R$_{19}$;

$R_{2p}$ and $R_{3p}$ each independently represent hydrogen, a ($C_1$–$C_6$)alkyl, a ($C_3$–$C_8$)cycloalkylmethyl, a ($C_3$–$C_8$)

cycloalkyl, a halogen, a nitro, a trifluoromethyl, a group —$OR_4$, a group —$NR_5R_6$, a 1-pyrrolyl, a cyano, a carbamoyl;

or $R_{2p}$ and $R_{3p}$ together constitute a trimethylene, tetramethylene or pentamethylene group;

$R_{4p}$ represents hydrogen; a ($C_1$–$C_6$)alkyl; a ($C_3$–$C_4$) alkenyl; a ($C_3$–$C_8$)cycloalkyl; a ($C_3$–$C_8$) cycloalkylmethyl; a ($C_1$–$C_4$)alkoxy($C_1$–$C_4$)alkyl; a benzyl;

$R_5$ and $R_6$ each independently represent a hydrogen, a ($C_1$–$C_6$)alkyl; or $R_5$ and $R_6$, together with the nitrogen atom to which they are attached, represent a heterocycle chosen from: pyrrolidine, piperidine, morpholine, thiomorpholine, piperazine substituted at position 4 with $R_9$;

$R'_7$ represents a ($C_1$–$C_4$)alkyl;

$R_7$ represents a hydrogen, a ($C_1$–$C_4$)alkyl or a benzyl;

$R_8$ represents a hydrogen, a ($C_1$–$C_4$)alkyl, a hydroxyl, or $R_7$ and $R_8$, together with the carbon atom to which they are attached, constitute a ($C_3$–$C_5$)cycloalkane;

$R_9$ represents hydrogen, a methyl, a group —X—OH or a group —X—$NR_5R_6$;

$R_{10}$ represents a hydrogen, a ($C_1$–$C_4$)alkyl, a benzyl, a carbamoyl, a cyano;

$R_{11}$ represents a hydrogen, a ($C_1$–$C_4$)alkyl, a group —X—OH, a group —X—$NR_5R_6$;

$R_{12}$ and $R_{13}$ each independently represent a hydrogen or a ($C_1$–$C_4$)alkyl;

$R_{14}$ represents hydrogen, $R_{14}$ can, in addition, represent a ($C_1$–$C_4$)alkyl when $R_{12}$ represents hydrogen and $R_{13}$ represents a ($C_1$–$C_4$)alkyl;

or $R_{13}$ and $R_{14}$ together represent a group Z;

$R_{15}$ represents hydrogen, a ($C_1$–$C_4$)alkyl, a group —$(CH_2)_sNR_5R_6$;

$R_{16}$ represents hydrogen, a ($C_1$–$C_8$)alkyl, a ($C_3$–$C_8$) cycloalkyl, a phenyl, a 2-piperidyl, a 3-piperidyl, a 4-piperidyl;

$R_{17}$ represents a ($C_1$–$C_6$)alkyl, a phenyl, a benzyl, a hydroxy($C_1$–$C_4$)alkyl, an amino($C_1$–$C_4$)alkyl;

$R_{18}$ and $R_{19}$ each independently represent a hydrogen, a ($C_1$–$C_4$)alkyl; $R_{18}$ can, in addition, represent a group —$(CH_2)_q$—$NR_5R_6$;

or $R_{18}$ and $R_{19}$, together with the nitrogen atom to which they are attached, represent a heterocycle chosen from: pyrrolidine, piperidine, morpholine, thiomorpholine, piperazine substituted at position 4 with $R_9$;

$R_{20}$ represents hydrogen, a ($C_1$–$C_4$)alkyl, a benzyl, a hydroxyphenylmethyl, a hydroxy($C_1$–$C_4$)alkyl, a mercapto($C_1$–$C_4$)alkyl; a —$(CH_2)_3$—NH—C(=NH) $NH_2$ group, a —$(CH_2)_4NH_2$ group, a group —$CH_2$— Im in which Im represents a 4-imidazolyl;

s=0 to 3;

t=0 to 3, on the condition that (s+t) is greater than or equal to 1;

r=2 to 5;

q=1 to 5;

T represents a direct bond or ($C_1$–$C_7$)alkylene;

X represents a ($C_2$–$C_7$)alkylene;

Y represents a ($C_1$–$C_7$)alkylene;

z represents a ($C_2$–$C_6$)alkylene;

the bivalent radicals A and E, together with the carbon atom and the nitrogen atom to which they are attached, constitute a saturated 5- to 7-membered heterocycle which can, in addition, be substituted with one or more ($C_1$–$C_4$)alkyls;

the bivalent radicals G and L, together with the nitrogen atoms to which they are attached, constitute a piperazine or imidazolidine or imidazoline ring, the said rings being optionally substituted on the carbon atoms with one or more ($C_1$–$C_4$)alkyls;

the group —NH—$AA_p$(OH) represents the residue of an amino acid:

$$-NH-\underset{\underset{X'_a}{/}}{\overset{\overset{X_a}{\backslash}}{C}}-COOH$$

where $X_a$ is hydrogen and $X'_a$ is hydrogen, a ($C_1$–$C_5$)alkyl or a non-aromatic $C_3$–$C_{15}$ carbocyclic radical; or alternatively $X_a$ and $X'_a$, together with the carbon atom to which they are attached, form a non-aromatic $C_3$–$C_{15}$ carbocycle;

and their salts.

Preferred compounds according to the invention correspond to the formula:

(I")

[Chemical structure diagram showing a pyrazole compound with OR"$_4$, CH$_3$O substituents on one phenyl ring, CO—NH—AA"(OH) group, and a phenyl ring with W$_2$, W$_3$, W$_4$, W$_5$ substituents]

in which:

R"$_4$ represents hydrogen, a methyl or a cyclopropylmethyl;

AA"(OH) represents a 2-carboxy-2-adamantyl, α-carboxycyclohexylmethyl or 9-carboxybicyclo [3.3.1]nonan-9-yl group;

among the substituents $w_2$, $W_3$, $w_4$ and $w_5$, at least one is hydrogen and at least one other is other than hydrogen, such that:

either (i) $w_5$ is hydrogen;

$w_3$ is hydrogen or methyl;

$w_2$ is ($C_1$–$C_4$)alkyl, ($C_3$–$C_6$)cycloalkyl, ($C_1$–$C_4$)alkoxy, chlorine or trifluoromethyl, or $w_2$ and $w_3$ together form a 1,4-butylene group;

$w_4$ is chosen either from the following groups:

(i1) dialkylaminoalkylaminocarbonyl $$\underset{ALK}{\overset{ALK}{\diagdown}}N-ALK'-NH-CO-$$

(i2) dialkylaminoalkyl(N-methyl)aminocarbonyl

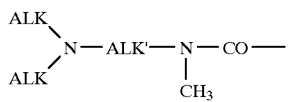

(i3) dialkylaminoalkyl(N-ethyl)aminocarbonyl

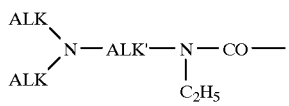

(i4) cyanoalkyl(N-methyl)aminocarbonyl

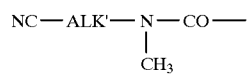

(i5) aminoalkylaminocarbonyl

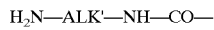

(i6) aminoalkyl(N-methyl)aminocarbonyl

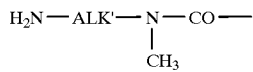

(i7) (N'-methyl)-(N'-alkoxycarbonyl)aminoalkyl(N-methyl)carbonyl

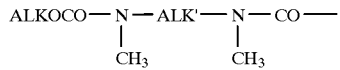

(i8) amidinoalkylaminocarbonyl

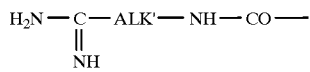

(i9) pyrrolidinoalkylaminocarbonyl

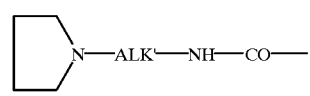

(i10) morpholinoalkylaminocarbonyl

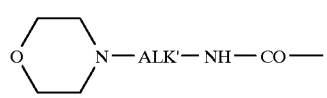

(i11) alkylaminoalkyl(N-methyl)aminocarbonyl

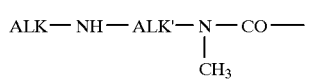

(i12) 2(1H)-imidazolinylalkylaminocarbonyl

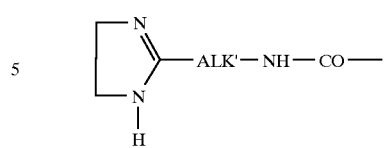

(i13) bis(dialkylaminoalkyl)aminocarbonyl $$(ALK_2N-ALK')_2N-CO-$$

(i14) aminocarbonylalkyl(N-methyl)aminocarbonyl

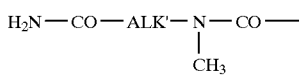

(i15) carboxyalkyl(N-methyl)aminocarbonyl

(i16) a group of structure

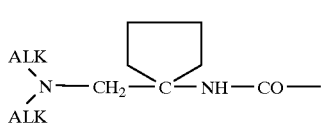

(i17) 2-pyridylaminocarbonyl

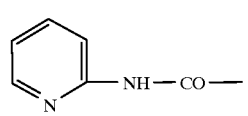

(i18) 1-benzyl-4-piperidylaminocarbonyl

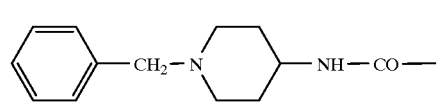

(i19) 3-quinuclidinylaminocarbonyl

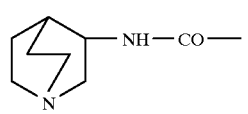

(i20) 4-piperidylaminocarbonyl

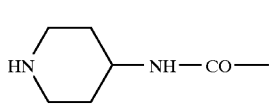

(i21) 2,2,6,6-tetramethyl-4-piperidylaminocarbonyl

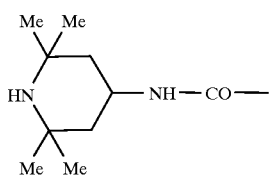

(i22) aminocarbonyl

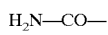

(i23) 4-alkylpiperazinocarbonyl

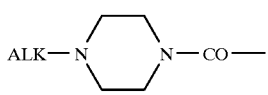

(i24) 4-dialkylaminopiperidinocarbonyl

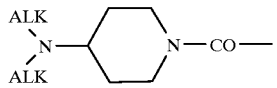

(i25) 3-dialkylaminopyrrolidinocarbonyl

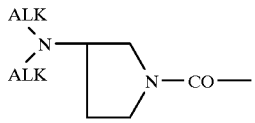

(i26) dialkylaminoalkyl(N-methyl)aminosulphonyl

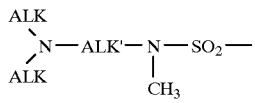

(i27) dialkylaminoalkyl(N-benzyl)aminosulphonyl

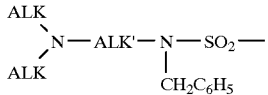

(i28) 1-alkyl-2-pyrrolidinylmethylaminocarbonyl

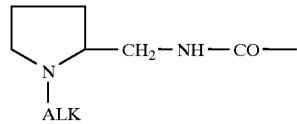

(i29) allylaminocarbonyl

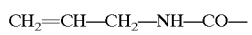

(i30) dialkylaminoalkyl(N-acetyl)amino

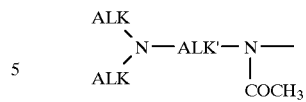

(i31) dialkylaminoalkylamino

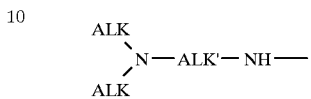

(i32) dialkylaminoalkylcarboxamido

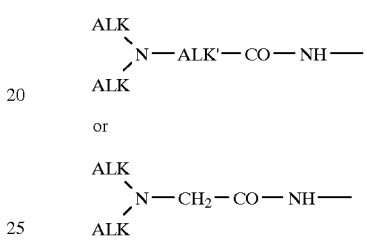

or alternatively $w_4$ is chosen from the following groups:

(i33) piperidinoalkylcarboxamido

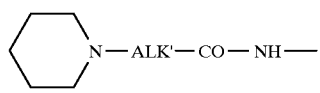

(i34) glycinamido

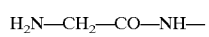

(i35) tosylamido

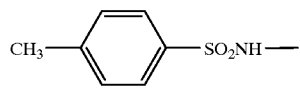

(i36) aminoalkylsulphonamido

or

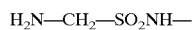

(i37) trialkylammonioalkyl(N-methyl)aminocarbonyl salt

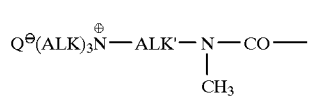

ALK being $(C_1-C_4)$alkyl and ALK' being $(C_2-C_5)$alkylene;
or
(ii)
$w_2$ and $w_5$ are hydrogen
$w_3$ is chlorine
$w_4$ is cyano or aminocarbonyl
or (iii)
   $w_2$ and $w_5$ are hydrogen, $w_3$ is isopropyl and $w_4$ is dialkylaminoalkylaminocarbonyl

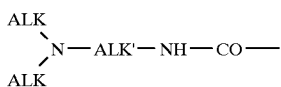

ALK and ALK' being as defined above;
or
(iv) $w_2$ and $w_5$ are hydrogen, $w_3$ is dialkylaminoalkyl(N-methyl)aminocarbonyl

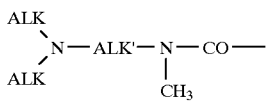

and $w_4$ is chloro;
ALK and ALK' being as defined above;
or
(v)
   $w_3$ and $w_4$ are hydrogen
   $w_2$ is chloro, $(C_1-C_4)$alkoxy or $(C_1-C_4)$alkyl
   $w_5$ is
(v1) dialkylaminoalkyl(N-methyl)aminocarbonyl

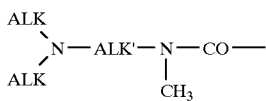

(v2) dialkylaminoalkylcarbonylamino

ALK and ALK' being as defined above;
their internal salts and their pharmaceutically acceptable salts, their quaternary ammonium salts and their solvates.

A preferred group of compounds according to the invention consists of the compounds of formula:

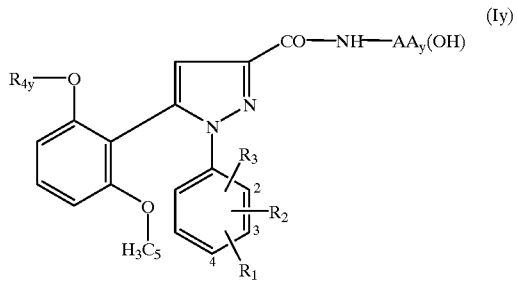

in which:
   $R_1$, $R_2$ and $R_3$ are as defined above for (I);
   $R_{4y}$ represents hydrogen, a $(C_1-C_4)$alkyl group, an allyl or a cyclopropylmethyl; and
   the group —NH—AA$_y$—(OH) represents either a residue selected from the residue of 2-aminoadamantane-2-carboxylic acid, of (S)-α-aminocyclohexaneacetic acid and of 9-aminobicyclo[3.3.1]-nonane-9-carboxylic acid, or the residue of 2-aminonorbornane-2-carboxylic acid;

their salts and their quaternary ammonium salts formed with acyclic or cyclic tertiary amines and their solvates.

Among the compounds of formula (Iy) as defined above, preference is given to those in which:
   $R_1$, as defined for (I), is at position 4 or 5;
   $R_2$ is at position 2 and represents a group chosen from: hydrogen, a $(C_1-C_6)$alkyl, a $(C_3-C_8)$cycloalkyl, a $(C_3-C_8)$cycloalkylmethyl, a $(C_1-C_6)$alkoxy, a $(C_3-C_8)$cycloalkyloxy, a chlorine, a trifluoromethyl;
   $R_3$ is at position 3 and represents hydrogen, a $(C_1-C_6)$alkyl, a $(C_3-C_8)$cycloalkyl, a $(C_3-C_8)$cycloalkylmethyl;
   or $R_2$ and $R_3$ together constitute a trimethylene, a tetramethylene or a pentamethylene; their salts and their quaternary ammonium salts formed with acyclic or cyclic tertiary amines and their solvates.

In particular, preference is given to the compounds of formula (Iy'):

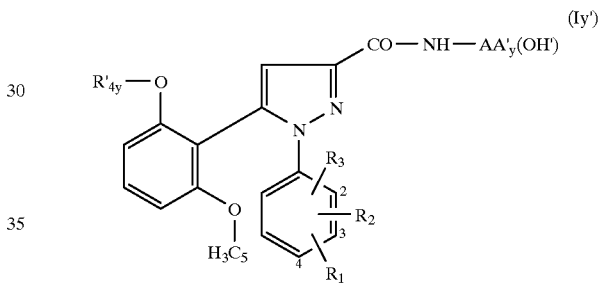

in which:
   $R_1$, $R_2$ and $R_3$ represent, respectively, $R_{1p}$, $R_{2p}$ and $R_{3p}$ as defined above for (Ip);
   $R'_{4y}$ represents a $(C_1-C_4)$alkyl or cyclopropylmethyl group; and
   the group —NH—AA'y—(OH) represents the residue of 2-aminoadamantane-2-carboxylic acid or of (S)-α-aminocyclohexaneacetic acid or of 2-aminonorbornane-2-carboxylic acid.

Among the compounds of formula (Iy') as defined above, preference is given to those in which:
   $R_1$ represents $R_{1p}$ as defined for (I) and is at position 4 or 5;
   R2 is at position 2 and represents a group chosen from: hydrogen, a $(C_1-C_6)$alkyl, a $(C_3-C_8)$cycloalkyl, a $(C_1-C_6)$alkoxy, a chlorine, a trifluoromethyl;
   $R_3$ is at position 3 and represents hydrogen or a $(C_1-C_6)$alkyl;
   or $R_2$ and $R_3$ together constitute a trimethylene, a tetramethylene or a pentamethylene;

and their salts.

Very special preference is given to the compounds of formula:

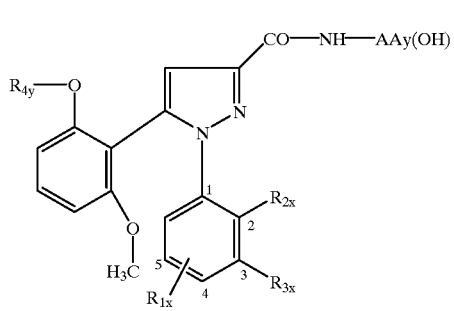

(Ix)

in which:

—R$_{4y}$ and NH—AA$_y$(OH) are as defined above for (Iy);

R$_{1x}$ is at position 4 or 5 and represents a group chosen from —T—CONR$_a$R$_b$, —SO$_2$NR$_a$R$_b$, —T—NR$_5$R$_6$, —N(R$_7$)COR$_e$, —OR$_d$, —N(R$_7$)SO$_2$R'$_7$, —T—NR$_{27}$R$_{28}$; the groups —T—, R$_a$, R$_b$, R$_d$, R$_e$, R$_5$, R$_6$, R$_7$, R'$_7$, R$_{27}$ and R$_{28}$ being as defined above for (I);

R$_{2x}$ and R$_{3x}$ each independently represent hydrogen; a (C$_1$–C$_6$)alkyl; a (C$_3$–C$_8$)cycloalkyl; a (C$_3$–C$_8$) cycloalkylmethyl;

on condition that R$_{2x}$ and R$_{3x}$ do not simultaneously represent hydrogen;

or R$_{2x}$ and R$_{3x}$ together constitute a tetramethylene group;

their salts and their quaternary ammonium salts formed with acyclic or cyclic tertiary amines and their solvates.

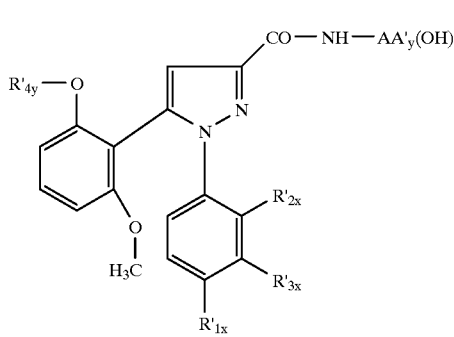

(Ix')

in which:

R'$_{4y}$ represents a (C$_1$–C$_4$)alkyl or cyclopropylmethyl group and NH—AA'$_y$(OH) is as defined above for (Iy');

R'$_{1x}$ represents a group chosen from —T—CONR$_a$R$_b$, —SO$_2$NR$_a$R$_b$, —Y—NR$_5$R$_6$, —N(R$_7$)COR$_e$, —OR$_d$; the groups —T—, NR$_a$R$_b$, R$_d$, R$_e$, R$_5$, R$_6$ and R$_7$ being as defined above for (Ip):

R'$_{2x}$ represents a (C$_1$–C$_6$)alkyl, a (C$_3$–C$_8$)cycloalkyl;

R'$_{3x}$ represents hydrogen or a (C$_1$–C$_6$)alkyl;

or R'$_{2x}$ and R'$_{3x}$ together constitute a tetramethylene group;

and their salts.

Among the compounds of formula (Iy), a preferred group consists of the compounds of formula:

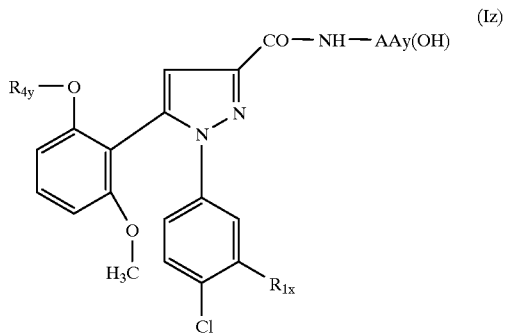

(Iz)

in which R$_{4y}$, R$_{1x}$ and NH—AAy(OH) are as defined above; preferably represents R'$_{4y}$, R$_{1p}$ and NH—AA'y(OH) as defined for (Iy')

their salts and their quaternary ammonium salts formed with acyclic or cyclic tertiary amines and their solvates.

The compounds of the following formula are chosen more especially:

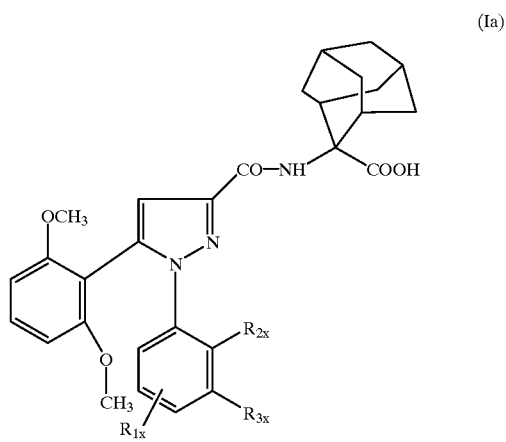

(Ia)

in which:

R$_{1x}$, R$_{2x}$ and R$_{3x}$ are as defined above for (Ix) preferably R'$_{1x}$, R'$_{2x}$ and R'$_{3x}$ as defined above for (Ix'), R'$_{1x}$ preferably being at the para position;

their salts and their quaternary ammonium salts formed with acyclic or cyclic tertiary amines and their solvates.

Preferentially, the invention relates to 2-[5-(2,6-dimethoxyphenyl)-1-[4-[N-methyl-N-(3-dimethylaminopropyl)carbamoyl]-2-isopropylphenyl]-3-pyrazolyl-carbonylamino]-2-adamantanecarboxylic acid, its internal salt and its salts which are preferably pharmaceutically acceptable, and its solvates.

According to another of its aspects, the present invention relates to a process for the preparation of the substituted 1-phenyl-3-pyrazolecarboxamides of formula (I) and their salts, characterized in that:

1) a functional derivative of a 1-phenyl-3-pyrazolecarboxylic acid of formula:

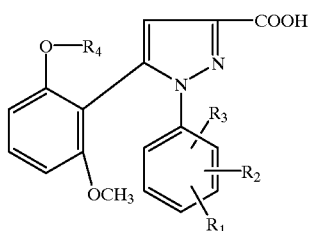

(II)

or

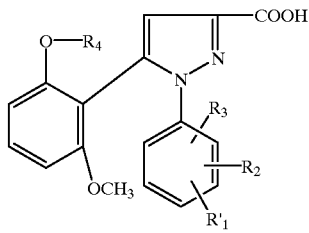

(II')

in which $R_1$, $R_2$, $R_3$ and $R_4$ have the meanings given above for the compound of formula (I) and $R'_1$ represents a precursor of $R_1$ chosen from nitro, amino, phthalimido, halo, hydroxyl, sulpho, hydroxy($C_1$–$C_7$)alkylene, cyano, carboxyl, ($C_1$–$C_4$)alkoxycarbonyl and benzyloxycarbonyl groups, is treated with an amino acid, optionally protected by protective groups which are customary in peptide synthesis, of formula:

$$H-HN-AA(OH) \quad (III)$$

in which —NH—AA(OH) is as defined above for the compound of formula (I);

2) where appropriate, the functional acid derivative thereby obtained, of formula:

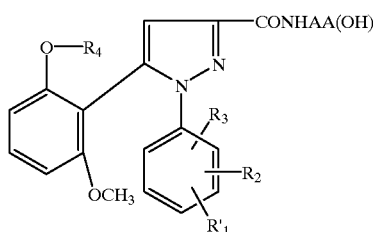

(I')

is subjected to a subsequent treatment suitable for converting the substituent $R'_1$, a precursor of $R_1$, to the substituent $R_1$;

3) if necessary, the compound thereby obtained in step 1) or in step 2) is deprotected to yield the corresponding free acid of formula (I);

4) where appropriate, a salt of the compound (I) thereby obtained or its quaternary ammonium salt is prepared.

As a functional derivative of the substituted 1-phenyl-3-pyrazolecarboxylic acid of formula (II) or (II'), it is possible to use the acid chloride, the anhydride, a mixed anhydride, a $C_1$–$C_4$ alkyl ester, an activated ester, for example the p-nitrophenyl ester, or the free acid appropriately activated, for example with N,N'-dicyclohexylcarbodiimide or with benzotriazol-1-yloxytris(dimethylamino)phosphonium hexafluorophosphate (BOP).

The amino acids of formula (III) may be used either as they are, or after prior protection of the carboxyl group with protective groups which are customary in peptide synthesis, as described, for example, in Protective Groups in Organic Chemistry, Ed. J. F. W. McOmie, Plenum Press, 1973, page 183, or in Protective Groups in Organic Synthesis, II Ed. J. F. W. Greene and P. G. M. Wuts, John Wiley & Sons, 1991, page 224.

For this protection, the carboxyl group of the amino acid (III) may be quite simply esterified, for example in the form of the methyl, benzyl or tert-butyl ester, the esterifying group then being removed by acid or basic hydrolysis or by hydrogenolysis. Protection by esterification can be used only when the group $R_1$ or $R'_1$ does not contain, for its part also, either an ester group which must be preserved, as in the case where, for example, $R_1$ might represent a group O—Y—$COOR_7$ or —Y—$COOR_7$ or —T—$CONR_7CHR_{20}COOR_7$ or —T—$CONR_7(CH_2)_4CH(NH_2)CO_2R_7$ with $R_7$=alkyl, or, in any case, a group liable to be affected during the unblocking of the ester group. Protection of the carboxyl group of the amino acid (III) may also be performed by silylation, for example with bis(trimethylsilyl)acetamide, it being possible for the said protection to be performed in situ. The silyl ester of the compound (I) is then readily removed during the isolation of the final product by simple acidification, hydrolysis or exchange with an alcohol.

Thus, in step 1) of the process, the chloride of a 1-phenyl-3-pyrazolecarboxylic acid, obtained by reacting thionyl chloride with an acid of formula (II) or (II'), may be reacted with an amino acid of formula (III), in a solvent such as acetonitrile, THF, DMF or DCM, under an inert atmosphere, at room temperature, for a time between a few hours and a few days, in the presence of a base such as pyridine, sodium hydroxide or triethylamine.

A variant of step 1) consists in preparing the acid chloride or the mixed anhydride of a 1-phenyl-3-pyrazolecarboxylic acid by reacting isobutyl or ethyl chloroformate with an acid of formula (II) or (II'), in the presence of a base such as triethylamine, and in reacting it with an N,O-bis (trimethylsilyl) derivative of an amino acid of formula (III), obtained by reacting bis(trimethylsilyl)acetamide or 1,3-bis (trimethylsilyl)urea or bis(trifluoromethylsilyl)acetamide with an amino acid of formula (III), in solvents such as acetonitrile and DCM, under an inert atmosphere, and for a time between 1 hour and a few days, at a temperature between room temperature and the refluxing temperature of the solvent.

Another variant to the procedure of step 1) consists in reacting the mixed anhydride of a 1-phenyl-3-pyrazolecarboxylic acid of formula (II) or (II') with an amino acid of formula (III), in a solvent such as DCM, under an inert atmosphere, at room temperature, for a time between 1 day and a few days, in the presence of a base such as triethylamine.

When the compound of formula (I) possesses a basic function and is obtained in the form of a free base, salification is performed by treatment with the chosen acid in an organic or aqueous solvent. By treatment of the free base, dissolved, for example, in an alcohol such as isopropanol, with a solution of the chosen acid in the same solvent, the corresponding salt is obtained, which salt is isolated according to standard techniques. Thus, for example, the hydrochloride, hydrobromide, sulphate, hydrogen sulphate, dihydrogen phosphate, methanesulphonate, methyl sulphate, oxalate, maleate, fumarate or 2-naphthalenesulphonate is prepared.

When the compound of formula (I) possesses a basic function and is isolated in the form of one of its salts, for example the hydrochloride or oxalate, the free base may be prepared by neutralization of the said salt with an inorganic or organic base such as sodium hydroxide or triethylamine, or with an alkali metal carbonate or bicarbonate such as sodium or potassium carbonate or bicarbonate.

When the product of formula (I) is obtained in acid form, it may be converted to a metal salt, in particular an alkali metal salt such as the sodium salt or an alkaline-earth metal salt such as the calcium salt, according to standard processes.

The compounds of formula (I) or (I') can undergo a dehydration in the presence of an anhydride, for example acetic anhydride, to form an oxazolone derivative of formula:

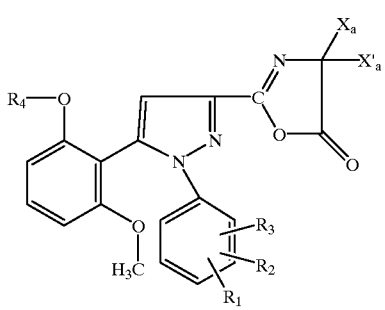
(Ic)

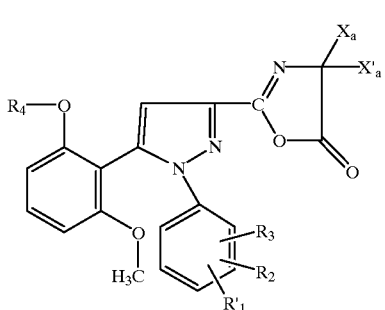
(I'c)

in which $R_1$, $R'_1$, $R_2$, $R_3$, $R_4$, $X_a$ and $X'_a$ have the meanings given above for (I) and $R'_1$ represents a precursor of $R_1$ as defined above.

These compounds are new and constitute a further aspect of the invention.

Among the compounds of formula (Ic) and (I'c), preference is given to those for which $X_a$ and $X'_a$, together with the carbon atom to which they are attached, constitute an adamantane ring system or a bicyclo[3.3.1]nonane, or alternatively $X_a$ is hydrogen and $X'_a$ represents a cyclohexane.

From a compound of formula (I'c) or (Ic), a compound of formula (I) or (I') is prepared again by hydrolysis in an acid medium or in a basic medium, for example in the presence of an alkali metal salt such as potassium tert-butylate.

The intermediate preparation of a compound of formula (Ic) may be useful to permit the purification of a compound of formula (I). Moreover, the intermediate preparation of a compound of formula (I'c) may be useful to permit the conversion of a substituent $R'_1$ to another substituent $R'_1$ or $R_1$, the acid function of the group NHAA(OH) being protected in the oxazolone group.

The substituted 1-phenyl-3-pyrazolecarboxylic acids of the formula:

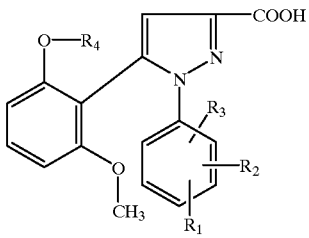
(II)

or

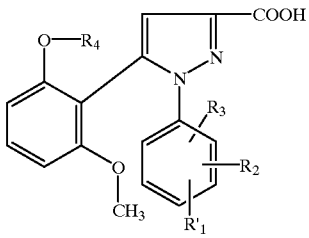
(II')

in which $R_1$, $R_2$, $R_3$ and $R_4$ have the definitions given above for the compounds (I) and $R'_1$ represents a precursor of $R_1$ chosen from halo, nitro, amino, phthalimido, hydroxyl, hydroxy($C_1$–$C_7$)alkylene, sulpho, cyano, carboxyl, ($C_1$–$C_4$) alkoxycarbonyl and benzyloxycarbonyl groups, as well as their functional derivatives of the acid function, are key intermediates in the preparation of the compounds of formula (I). When $R'_1$ is other than carboxyl or halo, the compounds of formula (II) and (II') are new, and they constitute a further aspect of the present invention.

The acids of formulae (II) and (II'), the chlorides of the acids of formulae (II) and (II'), the $C_1$–$C_4$ alkyl esters of the acids of formulae (II) and (II'), which can also be precursors of the said acids (in particular the methyl, ethyl and tert-butyl esters), and the mixed anhydride of the acids of formulae (II) and (II') with isobutyl or ethyl chloroformate are especially preferred intermediate products.

The process for preparing the compounds (II) or (II') via the esters (IIa) or (II'a) is represented by the following scheme:

SCHEME 1

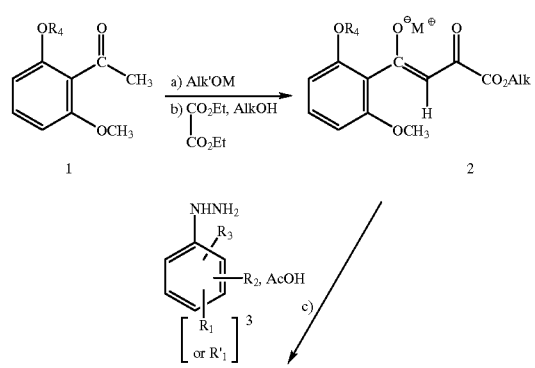

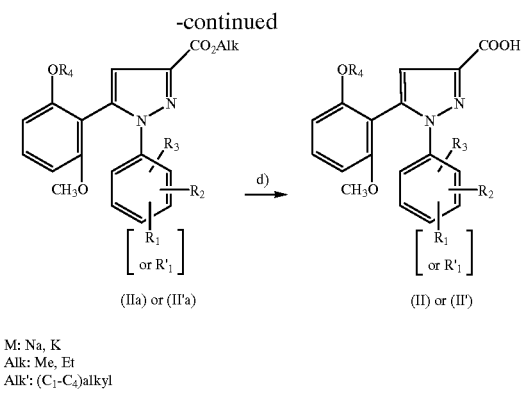

M: Na, K
Alk: Me, Et
Alk': (C$_1$-C$_4$)alkyl

In the first step a), a strong base such as a metal alcoholate is reacted with a ketone of formula 1 in which R$_4$ is as defined above, and then (step b) an equimolar amount of ethyl oxalate in an alkanol such as, for example, methanol or ethanol is reacted according to L. Claisen, Ber., 1909, 42, 59. After precipitation in an ether such as ethyl ether or isopropyl ether, the enolates 2 are separated by filtration. It is also possible to prepare a lithium enolate according to W. V. Murray et al., J. Heterocyclic Chem., 1989, 26, 1389.

The metal enolate 2 thereby prepared and an excess of phenylhydrazine derivative 3, or of a salt of the latter, are then heated to reflux of acetic acid (step c) to obtain the esters IIa or II'a.

On saponification of the esters IIa or II'a by the action of an alkaline agent such as, for example, potassium hydroxide, sodium hydroxide or lithium hydroxide, followed by acidification, the acids II or II' are obtained (step d).

Among the compounds of formula 3, some are new and constitute a further subject of the present invention.

Thus, the compounds of formula:

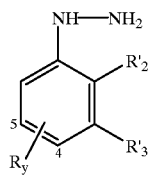

3' in which:
R'$_2$ and R'$_3$ each independently represent a hydrogen, a (C$_1$-C$_6$)alkyl, a (C$_3$-C$_8$)cycloalkyl, a (C$_3$-C$_8$) cycloalkylmethyl;

or R'$_2$ and R'$_3$ together constitute a trimethylene, tetramethylene or pentamethylene group;

R$_y$ is at position 4 or at position 5 and represents a group chosen from: cyano, carboxyl, (C$_1$-C$_4$)alkoxycarbonyl, benzyloxycarbonyl, sulpho, (C$_1$-C$_4$) alkylsulphonylamino, (C$_1$-C$_4$) alkylphenylsulphonylamino, carbamoyl, (C$_1$-C$_4$) alkylcarboxamido;

on condition that R'$_2$ and R'$_3$ do not simultaneously represent hydrogen and on condition that R'$_2$ is other than methyl when R$_y$ is a sulpho group; and their salts, are new and constitute a further subject of the present invention.

The phenylhydrazine derivatives (3) may be prepared according to Houben-Weyl, 1967, X-2, 169. For example, it is possible to carry out diazotization of the corresponding phenylamine in the presence of sodium nitrite, followed by reduction of the diazonium salt, for example by the action of stannous chloride. When the phenyl contains an electron-attracting substituent such as cyano or nitro, a fluorophenyl derivative may also be substituted with hydrazine hydrate to obtain the corresponding hydrazinophenyl derivative. The substituted phenylamines are known or prepared by known methods. For example, the aminosulphonic acids are prepared according to Houben-Weyl, Methoden der Organischen Chemie. Verlag, 1955, vol. IX, 450.

The phenylhydrazine derivatives substituted with a group R$_1$=YCO$_2$R$_7$ are prepared from corresponding aniline or nitrophenyl derivatives.

The conversion of a compound of formula I' or respectively of formula II' or of formula II'a in which the phenyl group is substituted with R'$_1$ to a compound of formula I or respectively of formula II or of formula IIa in which the phenyl group is substituted with R$_1$ is performed by standard methods well known to a person skilled in the art.

The compounds of formula IIa or II'a in which R$_1$ or R'$_1$ represents a carboxyl or carboxy(C$_1$-C$_7$)alkylene group enable compounds of formula IIa in which R$_1$ represents a group —TCONR$_a$R$_b$ to be prepared, with an amine HNR$_a$R$_b$, by reaction of the acid chloride prepared in an intermediate step, or of any other activated derivative of the acid such as the mixed anhydrides, activated esters or derivatives obtained with 1,3-dicyclohexylcarbodiimide.

In the same way, the compounds of formula I' in which R'$_1$ represents a group —TCOOH enable the compounds of formula I in which R$_1$ represents a group —TCONR$_a$R$_b$ to be prepared; the carboxylic acid function of the amino acid residue NHAA(OH) must then be protected in an intermediate step, for example by an ester group such as tert-butyl ester or by formation of the oxazolone derivative of formula (Ic).

From a compound of formula I or respectively Ic, or respectively from an ester of formula IIa, or respectively from an alkali metal salt of an acid of formula II, in which compounds the substituent R$_1$ is a group TCONH(CH$_2$)$_s$ CR$_7$R$_8$(CH$_2$)$_t$NR$_5$R$_6$, a compound of formula I or respectively of formula Ic or respectively of formula IIa, or respectively an alkali metal salt of acid of formula II, in which compounds the substituent R$_1$ is a group TCONR$_9$ (CH$_2$)$_s$CR$_7$R$_8$(CH$_2$)$_t$NR$_5$R$_6$, may be prepared by the action of an iodide of formula R$_9$I.

The compounds of formula IIa or respectively II or respectively Ic in which R$_1$ represents a carboxy(C$_1$-C$_7$) alkylene group enable the compounds of formula IIa or respectively II or respectively I in which R$_1$ represents a group —TCONR$_7$R$_c$ to be prepared by reacting the acid chloride prepared in an intermediate step with a compound NHR$_7$R$_c$, that is to say with a compound of formula NHR$_7$XOR$_7$ or a compound of formula HNR$_7$CHR$_{20}$CO$_2$R$_7$ or a compound of formula HNR$_7$(CH$_2$)$_4$CH—(NHPro) CO$_2$R$_7$ in which Pro represents a protecting group of the amine function used traditionally in peptide chemistry, for example tert-butoxycarbonyl or benzyloxycarbonyl.

By reacting the compounds of formula I in which R$_1$ represents a —CH$_2$CONH$_2$ group with sodium peroxide, the compounds of formula I in which R$_1$ represents a carboxymethyl group are obtained. By reducing the compounds of formula I in which R$_1$ represents a —CH$_2$CN group, for example by hydrogenation in the presence of a catalyst such as Raney® nickel, the compounds of formula I in which R$_1$ represents a —CH$_2$CH$_2$NH$_2$ group are obtained. The latter compounds enable compounds of formula I in which R$_1$ represents a group —CH$_2$CH$_2$NR$_5$R$_6$, a group —CH$_2$CH$_2$N (R$_7$)COR$_e$ or a group —CH$_2$CH$_2$N(R$_7$)SO$_2$R'$_7$ to be prepared by methods known to a person skilled in the art.

Similarly, the compounds of formula (I) in which $R_1$ represents a group —T'—CN, T' being a direct bond or a $(C_{1-C6})$alkylene, enable compounds of formula I to be prepared in which $R_1$ represents a group —T'—$CH_2NH_2$, and then compounds of formula I in which $R_1$ is a group —T'—$CH_2NR_5R_6$, a group —T'—$CH_2N(R_7)COR_e$ or a group —T'—$CH_2N(R_7)SO_2R'_7$.

The catalytic reduction may be carried out according to Catalytic Hydrogenation, R. L. Augustine— Marcel Dekker, 1967, 96–97; it may be applied to the compounds of formula I in which $R_2$ and $R_3$ are other than a nitro or a cyano and $R_4$ is other than a $(C_3$–$C_4)$alkenyl. The substitution of the amino group may be performed by different processes described, for example, in Catalytic Hydrogenation, R. L. Augustine—M. Dekker, 1965, 102–113, and Catalytic Hydrogenation over Platinum Metals, P. N. Rylander—Academic Press, 1967, 291. Thus, for example, the addition of an aldehyde of formula $R_V$CHO to an amino group yields an imine group which, on catalytic hydrogenation, is converted to secondary amine —$NHCH_2R_V$ in which $R_V$ represents a hydrogen or a $(C_1$–$C_3)$alkyl. The addition of a ketone of formula RCOR' yields an amine —NHCHRR' in which —CHRR' represents a group $R_5$, and $R_6$ is hydrogen. The addition of a $(C_{1-C4})$alkyl halide also enables an amino group substituted with one or two $(C_{1-C4})$alkyls to be prepared. The addition of a suitable dihalide enables compounds to be prepared in which $R_5$ and $R_6$, together with the nitrogen atom to which they are attached, constitute a heterocycle chosen from pyrrolidine, piperidine, morpholine, thiomorpholine and piperazine substituted at position 4 with $R_9$, aziridine, azetidine and perhydroazepine.

The compounds of formula IIa in which $R_1$ represents a group T—$NHSO_2R'_7$ enable compounds of formula II'a in which $R_1$ represents a group T—$N(XNR_5R_6)SO_2R'_7$ to be prepared by the action of a halide of formula $HalXNR_5R_6$. In an acid medium, compounds of formula II in which $R_1$ is a group $TNHXNR_5R_6$ which represents $TNHR_{28}$, may then be prepared. To obtain the compounds of formula I in which $R_1$ represents a group $TNR_{27}R_{28}$, substitution of the nitrogen is performed by known methods, either on a compound of formula II or on a compound of formula I.

The compounds of formula II'a, or respectively the compounds of formula II' or the compounds of formula I', in which $R'^1$ represents a nitro group may be converted to compounds of formula II'a, or respectively of formula II' or of formula I', in which $R'_1$ is an amino group; then, by known methods, the compounds of formula IIa, or respectively of formula II or of formula I, in which $R_1$ represents a group —$N(R_7)COR_e$ or $NR_5R_6$ are prepared.

The compounds of formula II'a, or respectively of formula II' or of formula I', in which $R'_1$ is an amino group also enable compounds of formula II'a, or respectively of formula II' or of formula I', in which $R'_1$ represents a hydroxyl group to be prepared; then, by known methods, the compounds of formula IIa, or respectively of formula II or of formula I, in which $R_1$ represents a group —$OR_d$ are prepared.

From the compounds of formula II'a in which $R'_1$ is a group —Y—OH, compounds of formula II'a in which $R'_1$ is a group —Y—Cl may be prepared by the action of hydrochloric acid or thionyl chloride; by the action of a sulphonic acid derivative on these same compounds bearing the substituent —Y—OH, compounds of the formula II'a in which $R'_1$ is the group —Y—$OSO_2W$, W representing a methyl, a trifluoromethyl or a tolyl, may be prepared. The action of an amine $NHR_5R_6$ on compounds of formula II'a substituted with a group —Y—Cl or a group —Y—O—$SO_2W$ enables compounds of formula IIa in which $R_1$ represents a group —Y—$NR_5R_6$ to be prepared.

When $R_2$ represents a nitro or cyano and $R_3$ represents hydrogen, the action of a compound $R_dOH$ in a basic medium on a compound of formula II'a, or respectively of formula II' or respectively of formula I', in which $R'_1$ is a halogen at the ortho or para position with respect to $R_2$ enables compounds of formula IIa, or respectively of formula II or respectively of formula I, in which $R_1$ is a group —$OR_d$ to be prepared.

When $R_2$ and $R_3$ are other than a halogen atom, a compound of formula IIa, or respectively of formula II or respectively of formula I, in which $R_1$ is a cyano may also be prepared from a compound of formula II'a, or respectively of formula II' or respectively of formula I', in which $R'_1$ is a halogen, by the action of a cyanide derivative, for example the cuprous cyanide.

The compounds of formula I in which $R_1$ is a cyano group enable the compounds of formula I in which $R_1$ is a carbamoyl group to be prepared by reaction with hydrogen peroxide in the presence of a base such as sodium hydroxide. In the same way, the compounds of formula II in which $R_1$ is a carbamoyl group are prepared from the compounds of formula IIa in which $R_1$ is a cyano group.

The compounds of formula I in which $R_1$ is a cyano group also enable the compounds of formula I in which $R_1$ represents a —$C(NH_2)$=NOH group or a group —$C(NH_2)$=$NO(CH_2)_rNR_5R_6$ to be prepared by reaction with hydroxylamine, where appropriate O-substituted with —$(CH_2)_qNR_5R_6$, in the presence of a base such as potassium carbonate.

From the compounds of formula IIa, or respectively of formula II or respectively of formula I, in which $R_1$ represents a $C(NH_2)$=NOH group, the compounds of formula IIa, or respectively of formula II or respectively of formula I, in which $R_1$ represents $C($=$NOH)NH(CH_2)_rNR_5R_6$ are prepared according to Chem. Ber., 1970, 103, 2330–2335.

By reducing the compounds of formula IIa, or respectively of formula II or of formula I, in which $R_1$ represents a cyano group, for example by hydrogenation in the presence of a catalyst such as platinum oxide, followed by reaction with an acid chloride or a suitable anhydride or respectively with a sulphonyl chloride, the compounds of formula IIa, or respectively of formula II or of formula I, in which $R_1$ represents a group —$CH_2NHCOR_{16}$ or respectively —$CH_2NHSO_2R'_7$ are obtained. Similarly, the compounds of formula IIa, or respectively of formula II or of formula I, in which $R_1$ represents a group —$CH_2N(R_7)COR_{16}$ or a group —$CH_2N(R_7)SO_2R'_7$, with $R_7$ other than hydrogen, are obtained by performing an alkylation reaction on the amide obtained in an intermediate step.

When the hydrogenation of a compound of formula II'a or respectively of formula II' or respectively of formula I', in which $R'_1$ represents a cyano group is performed in the presence of an amine $HNR_5R_6$, a compound of formula I or respectively of formula II or respectively of formula IIa, in which $R_1$ represents a group $CH_2NR_5R_6$ is obtained.

The reaction of the compounds of formula I in which $R_1$ represents a group TCN or —T—$CON(R_7)(CH_2)_qCN$ or a group —T—$N(R_7)CO(CH_2)_qCN$ or a group —$SO_2N(R_7)(CH_2)_qCN$ with hydrochloric acid in alcoholic solution AlkOH enables the corresponding imidate of formula:

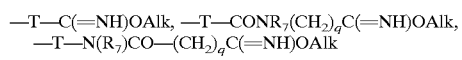
—T—N($R_7$)CO—$(CH_2)_qC$(=NH)OAlk or

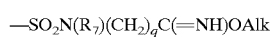

in which

Alk is a ($C_1$–$C_4$)alkyl to be obtained in an intermediate step.

If the imidate is reacted with an equimolar amount of amine $HNR_{12}R_{13}$, the compounds of formula I in which $R_1$ represents:

a group —$TC(NR_{12}R_{13})$=$NR_{14}$ a group —$TCON(R_7)(CH_2)_qC(NR_{12}R_{13})$=$NR_{14}$ or a group —$TN(R_7)CO(CH_2)_qC(NR_{12}R_{13})$=N—$R_{14}$ or a group —$SO_2N(R_7)(CH_2)_qC(NR_{12}R_{13})$=$NR_{14}$ with $R_{14}$=H are obtained.

If the imidate is reacted with an excess of amine $NH_2R_{13}$, in which $R_{13}$ is other than hydrogen, the compounds of formula I in which $R_1$ represents:

a group —$TC(NHR_{13})$=$NR_{13}$ a group —$TCON(R_7)(CH_2)_qC(NHR_{13})$=N—$R_{13}$ or a group —$TN(R_7)CO(CH_2)_qC(NHR_{13})$=$NR_{13}$ or a group —$SO_2N(R_7)(CH_2)_qC(NHR_{13})$=$NR_{13}$ are obtained.

If the imidate is reacted with a diamine of formula $H_2N$—Z—$NHR_{12}$, the compounds of formula I in which $R_1$ represents:

a group —$TC(NR_{12}R_{13})$=$NR_{14}$ a group —$TCON(R_7)(CH_2)_qC(NR_{12}R_{13})$=N—$R_{14}$ or a group —$TN(R_7)CO(CH_2)_qC(NR_{12}R_{13})$=$NR_{14}$ or a group —$SO_2N(R_7)(CH_2)_qC(NR_{12}R_{13})$=$NR_{14}$, in which $R_{13}$ and $R_{14}$ together constitute a $C_2$–$C_6$ alkylene group and $R_{12}$ represents a hydrogen or a ($C_{1–C4}$)alkyl, are obtained.

A compound of formula (I) in which $R_1$ contains an optionally substituted amidino radical may also be prepared according to the methods described in The chemistry of amidines and imidates, Saul Patai, 1975, John Wiley and Sons.

From the compounds of formula I, or respectively of formula II or IIa, in which $R_1$ represents a group —$TCONR_7(CH_2)_qCN$, compounds of formula I, or respectively II or IIa, in which $R_1$ represents a group —$TCONR_7(CH_2)_qCONH_2$ or a group —$TCONR_7(CH_2)_qCO_2R_7$ are prepared by known reactions.

When $R'_1$=$SO_3H$, a compound II'a in which $R'_1$=$SO_2Cl$ is prepared and then converted to another compound IIa in which $R_1$ is an aminosulphonyl group, optionally substituted, by the action of a suitable amine $HNR_aR_b$.

The compounds of formula I comprising a quaternary ammonium group are obtained from the corresponding amino compounds by the action of a compound of formula $QR_{24}$ in which Q can form an anion, for example iodide.

The amino acids of formula III include, for example, glycine, alanine, leucine, norleucine, isoleucine, valine, 1-adamantylglycine, 2-adamantylglycine, cyclopropylglycine, cyclopentylglycine, cyclohexylglycine, cycloheptylglycine, 1-aminocyclopropanecarboxylic acid, 1-aminocyclobutanecarboxylic acid, 1-aminocyclopentanecarboxylic acid, 1-aminocyclohexanecarboxylic acid, 1-aminocycloheptanecarboxylic acid, 1-amino-4-methylcyclohexanecarboxylic acid, 2-amino-2-adamantanecarboxylic acid, 2-aminobicyclo[3.2.1]octane-2-carboxylic acid, 9-aminobicyclo[3.3.1]nonane-9-carboxylic acid and 2-aminobicyclo[2.2.1]heptane-2-carboxylic or 2-amino-2-norbornanecarboxylic acid.

The amino acids of formula III are commercial products or may be very readily prepared according to standard methods. In particular, the non-commercial amino acids (III) are prepared according to the Strecker synthesis, Ann, 1850, 75, 27 or according to the synthesis of H. T. Bucherer et al., J. Pract. Chem., 1934, 141, 5, followed by a hydrolysis to yield the amino acids; for example, 2-amino-2-adamantanecarboxylic acid and 9-aminobicyclo[3.3.1] nonane-9-carboxylic acid are prepared according to H. T. Nagasawa et al., J. Med. Chem., 1973, 16, (7), 823.

α-Amino-1-adamantylacetic and α-amino-2-adamantylacetic acids are prepared according to B. Gaspert et al., Croatica Chemica Acta, 1976, 48 (2), 169–178.

2-Amino-2-norbornanecarboxylic acid is prepared according to H. S. Tager et al., J. Am. Chem. Soc., 1972, 94, 968.

α-Aminocycloalkylcarboxylic acids are prepared according to J. W. Tsang et al., J. Med. Chem., 1984, 27, 1663.

(R)- and (S)-cyclopentylglycines are prepared according to European Patent Application EP 477,049.

(R)- and (S)-cyclohexylglycines are prepared according to Rudman et al., J. Am. Chem. Soc., 1952, 74, 551.

(R)- and (S)-cyclohexylglycines may also be prepared by catalytic hydrogenation of (R)- and (S)-phenylglycines.

α-Aminocycloalkylcarboxylic acids of R or S configuration may also be prepared by stereospecific enzymatic hydrolysis of the corresponding racemic N-acetyl derivatives according to J. Hill et al., J. Org. Chem., 1965, 1321.

The compounds of formula (I) and their salts possess a very great affinity for human neurotensin receptors in the tests described by D. Gully et al. in Proc. Natl. Acad. Sci. U.S.A., 1993, 90, 65–69.

The compounds of formula I and their salts were studied in vivo. Working according to the technique described by M. Poncelet et al. in Naunyn Schmiedberg's Arch. Pharmacol., 1994, 60, 349–357, it is observed that a compound according to the invention, administered orally, antagonizes the contralateral pivoting induced by unilateral intrastriatal injection of neurotensin in mice.

Moreover, working according to the technique described by D. Nisato et al. in Life Sciences, 1994, 54, 7, 95–100, it is found that a compound according to the invention, administered intravenously, inhibits the increase in blood pressure induced by intravenous injection of neurotensin in guinea pigs.

The compounds described in Patent EP 0,477,049 exhibit a lower activity in these tests than that of the compounds according to the present invention.

The compounds of the present invention are of low toxicity; in particular, their acute toxicity is compatible with their use as a medicinal product. For such a use, an effective amount of a compound of formula I, or of one of its pharmaceutically acceptable salts, is administered to mammals for the treatment of neurotensin-dependent pathologies. Thus, the compounds of the present invention may be used for the treatment of neuropsychiatric disorders, especially those associated with a dysfunction of the dopaminergic systems, for example psychoses, more especially schizophrenia, and diseases of movement such as Parkinson's disease (D. R. Handrich et al., Brain Research, 1982, 231, 216–221 and C. B. Nemeroff, Biological Psychiatry, 1980, 15 (2), 283–302). They may be used to diagnose and/or treat malignant neoplastic diseases, for example human meningiomas which are not surgically accessible (P. Mailleux, Peptides, 1990, 11, 1245–1253), cancers of the prostate (I. Sehgal et al., Proc. Nat. Acad. Sci., 1994, 91, 4673–4677) and small cell cancers of the lung (T. Sethi et al., Cancer Res., 1991, 51, 3621–3623). They may be used in the treatment of motor, secretory, ulcerous and/or tumoral gastro-intestinal disorders (review by A. Shulkes in "Gut Peptides: Biochemistry and Physiology, Ed. J. Waish and G. J. Dockray, 1994"). Thus, the compounds I according to the invention may be used in the treatment of complaints such as: irritable bowel syndrome, diarrhoea, colitis, ulcers, tumours of the gastrointestinal tract, dyspepsia, pancreatitis and oesophagitis. They may also be of value as modulators of food intake (Beck, B. Metabolism, 1995, 44, 972–975). The compounds according to the invention may be indicated as diuretics, as well in the case of cardiovascular disorders, and also in the case of pathologies associated with a histamine release such as inflammatory processes (D. E. Cochrane et al., Faseb J., 1994, 8, 7, 1195). These compounds may also be useful for treating certain disorders caused by stress, such as migraines, neurogenic pruritus and interstitial cystitis (Theoharides T. C. et al., Endocrinol., 1995, 136, 5745–5750). The compounds of the present invention may also be of value in analgesia, by acting on the effects of morphine (M. O. Urban, J. Pharm. Exp. Ther., 1993, 265, 2, 580–586).

Thus, the subject of the present invention, according to another of its aspects, is pharmaceutical compositions containing as active principles the compounds of formula I or their possible pharmaceutially acceptable salts.

In the pharmaceutical compositions of the present invention for oral, sublingual, subcutaneous, intramuscular, intravenous, transdermal or rectal administration, the active principles may be adminisered, in single-dose administration forms, as a mixture or with standard pharmaceutical vehicles, to animals and human beings. Suitable single-dose administration forms comprise forms for oral administration, such as tablets, gelatin capsules, powders, granules and oral solutions or suspensions, forms for administration by inhalation, forms for sublingual and buccal administration, forms for subcutaneous, transcutaneous, intramuscular or intravenous administration and forms for rectal administration.

In order to obtain the desired effect, the dose of active principle can vary between 0.5 and 1000 mg per day, and preferably between 2 and 500 mg.

Each single dose can contain from 0.5 to 250 mg of active principle, and preferably from 1 to 125 mg, in combination with a pharmaceutical vehicle. This single dose can be administered 1 to 4 times daily.

When a solid composition is prepared in the form of tablets, the active principle is mixed with a pharmaceutical vehicle such as gelatin, starch, lactose, magnesium stearate, talc, gum arabic or the like. It is possible to coat the tablets with sucrose or with other suitable substances, or they may alternatively be treated in such a way as to have a sustained or delayed activity and to release continuously a predetermined amount of active principle.

A gelatin capsule preparation is obtained by mixing the active principle with a diluent and pouring the mixture obtained into soft or hard gelatin capsules.

A preparation in syrup or elixir form can contain the active principle together with a sweetener, preferably a zero-calorie sweetener, and methylparaben and propylparaben as antiseptic, as well as an agent imparting flavour and a suitable colorant.

The water-dispersible powders or granules can contain the active principle mixed with dispersing agents or wetting agents, or suspending agents such as polyvinylpyrrolidone and the like, as well as with sweeteners or flavour correctors.

For rectal administration, suppositories are employed, which are prepared with binding agents melting at rectal temperature, for example cocoa butter or polyethylene glycols.

For parenteral administration, aqueous suspenions, isotonic saline solutions or sterile and injectable solutions are used, which contain pharmacologically compatible dispersing and/or wetting agents, for example propylene glycol or butylene glycol.

The active principle may also be formulated in the form of microcapsules, optionally with one or more vehicles or additives.

To improve the solubility of the products of the invention, the compounds of formula I or their pharmaceutically acceptable salts may also be presented in the form of complexes with cyclodextrins.

In the description and in the examples, the following abbreviations are used:
MeOH: methanol
EtOH: ethanol
Ether: ethyl ether
Ethereal hydrogen chloride=a saturated solution of hydrochloric acid in ether
Ethanolic hydrogen chloride=a saturated solution of hydrochloric acid in ethanol
Iso ether: isopropyl ether
AcOEt: ethyl acetate
MeCN: acetonitrile
DCM: dichloromethane
DMF: dimethylformamide
DMSO: dimethyl sulphoxide
THF: tetrahydrofuran
HCl: hydrochloric acid
$H_2SO_4$: sulphuric acid
AcOH: acetic acid
TFA: trifluoroacetic acid
NaOH: sodium hydroxide
KOH: potassium hydroxide
LiOH: lithium hydroxide
$NH_4OH$: ammonium hydroxide
$Na_2SO_4$: sodium sulphate
$NaHCO_3$: sodium hydrogen carbonate
$NaHSO_3$: sodium hydrogen sulphite
$Na_2CO_3$: sodium carbonate
$K_2CO_3$: potassium carbonate
$P_2O_5$: phosphorus pentoxide
NBS: N-bromosuccinimide
$POCl_3$: phosphorus oxychloride
$NaNO_2$: sodium nitrite
$SOCl_2$: thionyl chloride
$SnCl_2$: stannous chloride
CuCN: suprous cyanide
Me, MeO: methyl, methoxy
Et: ethyl
iPr: isopropyl
iBu: isobutyl
n-Bu: n-butyl
t-Bu: tert-butyl
Bz: benzyl
m.p.: melting point
RT: room temperature
Silica H: silica gel 60 H marketed by MERCK (DARMSTADT)
NMR: nuclear magnetic resonance Except where otherwise stated, NMR spectra are recorded at 200 MHz in DMSO-$d_6$. Chemical shifts δ are expressed in parts per million (ppm) relative to tetramethylsilane as internal reference.
s: singlet
bs: broad singlet
ss: split singlet d: doublet
dd: doublet of doublet
t: triplet
qr: quartet
qt: quintet
sp: septet
u.c.: unresolved complex
mt: multiplet Preparation 1.1

Methyl 4-(2,6-dimethoxyphenyl)-4-oxido-2-oxo-3-butenoate sodium salt: Compound A.

A solution of 100 g of 2,6-dimethoxyacetophenone and 7.5 ml of ethyl oxalate in 520 ml of anhydrous MeOH is added slowly to a solution of sodium methylate prepared from 12.7 g of sodium and 285 ml of anhydrous MeOH. The reaction mixture is heated to reflux for 7 hours and left overnight at RT. It is poured into 2 liters of isopropyl ether and left stirring for 15 minutes. The expected product is obtained by filtration, washing with isopropyl ether and drying under vacuum, m=120 g, m.p.=178° C.

Ethyl 4-(2,6-dimethoxyphenyl)-4-oxido-2-oxo-3-butenoate potassium salt: Compound $A_1$.

A solution of 13.4 g of 95% potassium tert-butylate in 72 ml of ethanol is added over 6 minutes to a solution, stirred and heated to 50° C., of 18 g of 2,6-dimethoxyacetophenone in 54 ml of ethanol. The mixture is heated to reflux, 16.3 ml of ethyl oxalate are added over 9 minutes and refluxing is continued for 1 hour. 40 ml of ethanol are then distilled off and the mixture is allowed to cool with stirring for two and a half hours. The mixture is filtered, and the precipitate is washed with 40 ml of ethanol and dried under vacuum at 60° C. for 17 hours to obtain 31 g of expected product.

NMR: 1.2:t:3H; 3.6:s:6H; 4:mt:2H; 5.5:s:1H; 6.55:d:2H; 7.1:t:1H.

Preparation 1.2

Ethyl 4-[2-(cyclopropylmethyloxy)-6-methoxyphenyl]-4-oxido-2-oxo-3-butenoate sodium salt.

A) 2-(Cyclopropylmethyloxy)-6-methoxyacetophenone.

32.7 ml of a 50% solution of caesium hydroxide in water are added at RT to a solution of 26 g of 2-hydroxy-6-methoxyacetophenone in 400 ml of 2-propanol, and the mixture is left stirring for 15 minutes at RT. It is concentrated under vacuum, the residue is taken up with 2-propanol, the mixture is concentrated under vacuum, toluene is then added and the resulting mixture is concentrated under vacuum. The residue is dissolved in 200 ml of DMF, 25.3 g of cyclopropylmethyl bromide are added and the mixture is heated to 80° C. for 2 hours 30 minutes. It is concentrated under vacuum, the residue is taken up with water, the mixture is extracted with AcOEt, the organic phase is washed with a saturated NaCl solution and dried over $Na_2SO_4$ and the solvent is evaporated off under vacuum. 32.7 g of the expected product are obtained.

B) Ethyl 4-[2-(cyclopropylmethyloxy)-6-methoxyphenyl]-4-oxido-2-oxo-3-butenoate sodium salt.

A solution of 32.6 g of the compound obtained in the preceding step and 20.1 ml of diethyl oxalate in 100 ml of EtOH is added slowly to a solution of sodium ethylate prepared from 3.4 g of sodium and 60 ml of EtOH. The mixture is heated overnight at 60° C., allowed to cool to RT and concentrated under vacuum. The residue is taken up with pentane, and the precipitate formed is drained, washed with pentane and dried under vacuum. 41.2 g of the expected product are obtained.

PREPARATIONS OF THE HYDRAZINES 3

Preparation 2.1

3-Isopropyl-4-hydrazinobenzoic acid hydrochloride.

A) 2-Isopropylacetanilide.

This compound is described in Bull. Soc. Chim., France, 1949, 144.

A mixture containing 300 ml of toluene and 31 ml of 2-isopropylaniline is cooled in ice, and 22 ml of acetic anhydride are added slowly. After 40 minutes with stirring at RT, the reaction medium is evaporated and the residue is then taken up with petroleum ether. The precipitate formed is drained. 35.9 g of the expected product are obtained after crystallization in petroleum ether, m.p.=81° C.

B) 4-Bromo-2-isopropylacetanilide.

This compound is described in J. Med. Chem., 1974, 17(2), 221.

A few drops of a solution of 10.1 ml of bromine in 180 ml of acetic acid are added slowly to a mixture containing 34.8 g of the compound obtained in the preceding step in 250 ml of acetic acid, and the mixture is then heated to 50° C.; after cooling, a few drops of the solution are added again and the mixture is heated to 50° C., this being continued until the addition is complete. The reaction medium is gradually heated to reflux and then allowed to return to RT overnight. The precipitate formed is filtered off and then added to a dilute solution of $NaHSO_3$. The product is filtered off again, rinsed with water and then dried over $P_2O_5$. 27.4 g of the expected product are obtained, m.p.=134° C.

The compound of step B) may also be prepared according to the procedure described below.

B') 4-Bromo-2-isopropylacetanilide.

A mixture is prepared containing 117.6 g of 2-isopropylacetanilide in 330 ml of DMF, and 117.6 g of NBS in 330 ml of DMF are added over 25 minutes. The mixture is left stirring at RT for 5 hours and then poured into 1.5 liters of water while cooling the reaction medium with ice. The precipitate formed is filtered off, rinsed with water and then dried at 50° C. under vacuum. The filtrate is extracted with DCM (twice), washed with water and then dried over $Na_2SO_4$ to obtain a second fraction of the expected product. By combining the different purified fractions, 158 g of the expected product are obtained, m.p.=134° C.

C) 4-cyano-2-isopropylacetanilide.

A mixture containing 26.48 g of the product obtained in the preceding step, 60 ml of DMF, 1 ml of water and 10.25 g of cuprous cyanide is stirred under reflux for 10 hours. After cooling, the mixture is poured into a solution of 50 g of sodium cyanide in 150 ml of water at 40° C. The precipitate formed is filtered off and rinsed several times with water. 16.7 g of the expected product are obtained, m.p.=134° C.

D) 4–Cyano-2-isopropylaniline hydrochloride.

16.13 g of the compound obtained in the preceding step, 65 ml of 100% ethanol and 40 ml of 1N HCl are mixed, and the mixture is stirred under reflux for 19 hours. After one night at RT, 10% NaOH solution is added until a pH of 10 is obtained. The reaction medium is extracted twice with DCM, and the organic phase is dried over $Na_2SO_4$ and concentrated under vacuum. The residue is dissolved in ether and ethereal hydrogen chloride is added. The precipitate formed is filtered off and rinsed with ether. 15.32 g of the expected product are obtained, which product crystallizes in the $Et_2O/HCl$ mixture, m.p.=188° C.

E) 4-Amino-3-isopropylbenzoic acid hydrochloride.

This compound is described in J. Med. Chem., 1974, 17(2), 221.

A mixture containing 1 g of the compound obtained in the preceding step, 2.86 g of ground potassium hydroxide, 6 ml of water and 0.5 ml of dimethoxyethane is heated to reflux for 12 hours. After cooling, concentrated HCl is added until a pH of 1 is obtained, and the mixture is then extracted twice with DCM; the organic phase is dried over $Na_2SO_4$ and concentrated. 0.96 g of the expected product is obtained, m.p.=128° C.

F) 3-Isopropyl-4-hydrazinobenzoic acid hydrochloride.

A mixture containing 0.96 g of the product obtained in the preceding step, 22 ml of concentrated HCl and 20 ml of acetic acid is cooled to −5° C., 0.36 g of $NaNO_2$ in 4 ml of water is added and the mixture is then left stirring at 0° C. for 1 hour 15 minutes. It is cooled to −10° C., and 3.73 g of stannous chloride dihydrate in 4 ml of concentrated HCl are added. The temperature is allowed to rise to 18° C., and the precipitate formed is then filtered off and rinsed with 1 ml of dilute HCl. 0.96 g of the expected product is obtained after drying over $P_2O_5$.

Preparation 2.1

3-Isopropyl-4-hydrazinobenzoic acid hydrochloride may also be prepared according to the procedure described below.

A) 4-Bromo-2-isopropylacetanilide.

200 ml of acetic anhydride are added over 10 minutes to 300 ml of 2-isopropylaniline while the temperature is maintained below 60° C. After 45 minutes of stirring at RT, a solution of one equivalent of NBS in 720 ml of DMF is added. After 2 hours of stirring, the mixture is poured into 5.7 l of water/AcOEt (2:1; v/v) mixture, settling is allowed to take place, and the organic phase is separated, dried over $Na_2SO_4$ and evaporated under vacuum. The residue is solidified in isopropyl ether and filtered off to obtain 367 g of the expected product.

B) 4-Cyano-2-isopropylacetanilide.

10.25 g of the product of step A and 1.2 equivalents of cuprous cyanide in 20 ml of DMF are heated to reflux for 6 hours. The mixture is cooled to 20° C. and poured into a mixture of 200 ml of AcOEt and 200 ml of 20% ammonium hydroxide. The organic phase is washed again with 50 ml of 20% ammonium hydroxide and then twice with saturated NaCl solution. After drying over $Na_2SO_4$, it is evaporated under vacuum, and the residue is treated with isopropyl ether, filtered off and dried at 40° C. under vacuum to obtain 6.15 g of the expected product.

The compound of step B may also be prepared according to the procedure below:

B') Argon is bubbled through a stirred mixture of 22.16 g of product of step A and 0.6 equivalent of zinc cyanide in 67 ml of anhydrous DMF. The mixture is heated to 80° C. and 2 g of tetrakis(triphenylphosphine)palladium(0) are added while the mixture is protected from light. After 3 hours of stirring at 80° C., the mixture is allowed to cool to RT and 120 ml of 4% ammonium hydroxide and 200 ml of AcOEt are added, and the combined organic phases are washed again with 4% ammonium hydroxide. They are dried over $Na_2SO_4$ and evaporated under vacuum, and the residue is treated with isopropyl ether, filtered off and dried under vacuum to obtain 15 g of the expected nitrile.

C) 4-Amino-3-isopropylbenzoic acid hydrochloride.

A mixture of 100 g of the product of step B with 500 ml of concentrated HCl and 500 ml of AcOH is heated to reflux for 10 hours. It is concentrated under vacuum, and the precipitate is filtered off and dried under vacuum to obtain 103.8 g of expected product.

D) 3-Isopropyl-4-hydrazinobenzoic acid hydrochloride.

A solution of 27.7 g of $NaNO_2$ in 250 ml of water is added slowly to a mixture, cooled to −50° C., of 59 g of the product of step C with 1050 ml of AcOH and 1420 ml of concentrated HCl. After 1 hour 20 minutes of stirring at 0° C., the mixture is cooled to −10° C. and a solution of 236 g of $SnCl_2.2H_2O$ in 250 ml of concentrated HCl is added. The temperature is allowed to rise to RT, and the precipitate is filtered off, washed with concentrated HCl and dried under vacuum to obtain 56.36 g of expected product.

Preparation 2.2

3-Isopropyl-4-hydrazinobenzenesulphonic acid hydrochloride.

A) 4-Amino-3-isopropylbenzenesulphonic acid.

5.7 ml of $H_2SO_4$ are added to 10 ml of water, the mixture is heated to 80° C. and 13.5 g of 2-isopropylaniline are then added. The water is evaporated off by heating under vacuum, and the temperature is then gradually raised over one and a half hours to reach 260° C. After 3 hours with stirring and under vacuum at 260° C., the reaction medium is allowed to return to RT and to atmospheric pressure, and is then heated for 30 minutes in the presence of 15 ml of NaOH and 100 ml of water in order to dissolve the reaction medium. The insoluble matter is filtered off, and the mixture is cooled to 5° C. and then acidified to pH 1 by adding concentrated $H_2SO_4$. The precipitate formed is filtered off, washed with 5 ml of cold water and dried to obtain 20 g of the expected product.

NMR: 1.1:d:6H; 2.95:mt: 1H; 6.85:d:1H; 7.45:dd:1H; 7.6:d:1H.

B) 3-Isopropyl-4-hydrazinobenzenesulphonic acid hydrochloride.

10 ml of ice and 3.2 g of $NaNO_2$ are added to a solution of 10 g of the product prepared in the preceding step in 10 ml of 30% NaOH and 20 ml of water. This solution is poured slowly into a solution of 30 ml of concentrated HCl in 20 ml of water at a temperature of between −5° C. and −15° C. The mixture is left stirring for one hour at this temperature, and 26 g of stannous chloride dihydrate in 40 ml of concentrated HCl are then added at a temperature of between 0° C. and −5° C. After two and a half hours with stirring at RT, the product obtained is filtered off and then dried under vacuum in the presence of $P_2O_5$. 9.7 g of the expected product are thereby obtained.

NMR: 1.2:d:6H; 3.15:mt:1H; 6.8:d:1H:7.45:d:1H; 7.55:s:1H; 7.9:bs:1H; 10:bs:3H.

Preparation 2.3

4-Hydrazino-5,6,7,8-tetrahydro-1-naphthalenecarboxylic acid hydrochloride.

A) 4-Amino-5,6,7,8-tetrahydro-1-naphthalenecarboxylic acid.

4-Nitro-5,6,7,8-tetrahydro-1-naphthalenecarboxylic acid is described in Chem. Pharm. Bull., 1984, 32, 3968. The hydrogenation of 1.48 g of this nitro derivative is performed in methanol in the presence of Raney® nickel. After 4 hours with stirring, the catalyst is filtered off, the mixture is evaporated to dryness and the residue is taken up with ether and filtered off to obtain 1 g of the expected product. m.p.=180° C. (dec.).

B) 4-Hydrazino-5,6,7,8-tetrahydro-1-naphthalenecarboxylic acid hydrochloride.

A solution of 0.26 g of $NaNO_2$ in 1 ml of water is added to a solution, cooled to −5° C., of 0.73 g of 4-amino-5,6,7, 8-tetrahydro-1-naphthalenecarboxylic acid in 10 ml of concentrated HCl. After one and a half hours of stirring at −5° C., a solution of 3.4 g of $SnCl_2.2H_2O$ in 34 ml of concentrated HCl is added at −5° C. The mixture is stirred for 1 hour at RT and filtered, and the product is washed with concentrated HCl and dried under a stream of dry nitrogen to obtain 0.67 g of the expected hydrazine.

Preparation 2.4

4-Hydrazino-5,6,7,8-tetrahydro-1-naphthalenesulphonic acid hydrochloride.

A) 4-Amino-5,6,7,8-tetrahydro-1-naphthalenesulphonic acid.

A hot suspension of 20 g of sulphamic acid in 40 ml of N-methylpyrrolidone is added to a solution of 10 g of 5,6,7,8-tetrahydronaphthylamine in 100 ml of 1,2-dichlorobenzene. The mixture is heated with stirring for 7 hours at 150° C. The product is filtered off and washed with dichlorobenzene and then with toluene. The precipitate is resuspended in 70 ml of water and neutralized to pH 7 with 5.5 ml of 30% sodium hydroxide. The insoluble matter is filtered off and the aqueous phase is extracted with ether. The aqueous phase is adjusted to pH 5 by adding HCl, at 5° C.; the mixture is filtered, and the residue is washed with water and dried to obtain 7.5 g of the expected product.

B) 4-Hydrazino-5,6,7,8-tetrahydro-1-naphthalenesulphonic acid hydrochloride.

1 g of $NaNO_2$ is added to a solution of 3 g of the acid obtained in step A in 10 ml of water and 2 ml of 30% sodium hydroxide. This solution is poured over 1 hour into 10 ml of concentrated HCl cooled to 5° C. After stirring for 3 hours at 5° C., a solution of 7.5 g of $SnCl_2.2H_2O$ in 15 ml of concentrated HCl is added slowly while the temperature is maintained at 5° C. The mixture is left stirring for one and a half hours at RT and filtered, and the residue is dried under vacuum to obtain 2.86 g of the expected product.

NMR ($D_2O$—NaOD): 1.6:mt:4H; 2.25:mt:2H; 2.9:mt:2H; 6.75:d:1H; 7.6:d:1H.

Preparation 2.5

4-Hydrazino-3-methylbenzamide hydrochloride.

A) 4-Amino-3-methylbenzamide.

This product is prepared by catalytic hydrogenation of 3-methyl-4-nitrobenzamide, m.p.=124° C.

B) 4-Hydrazino-3-methylbenzamide hydrochloride.

0.5 g of the compound of step A is dissolved in 10 ml of 1N HCl and 5 ml of concentrated HCl. The mixture is cooled to 0° C. and a solution of 230 mg of $NaNO_2$ in 3 ml of water is added. After 15 minutes at −10° C., a solution of 1.5 g of $SnCl_2.2H_2O$ in 5 ml of concentrated HCl is added. After 1 hour the precipitate is filtered off and dried under vacuum over $P_2O_5$ to obtain 390 mg of the expected product.

Preparation 2.6

2,3-Dimethyl-4-hydrazinobenzoic acid hydrochloride.

A solution of 1.87 g of $NaNO_2$ in 7 ml of water is added slowly to a solution, cooled to −5° C., of 4.5 g of 4-amino-2,3-dimethylbenzoic acid in 135 ml of concentrated HCl. After 2 hours of stirring at −5° C., a solution of 25 g of $SnCl_2.2H_2O$ in 250 ml of concentrated HCl is added at −10° C., and the mixture is stirred for 30 minutes at −5° C. and then 2 hours at RT. The mixture is filtered, and the precipitate is washed with 5 ml of concentrated HCl and dried under a stream of dry nitrogen and then under vacuum to obtain 5.5 g of expected product.

NMR: 2.1:s:3H; 2.4:s:3H; 6.8:d:2H; 7.6:d:2H; 8.2:s:1H; 10:bs:2H.

Preparation 2.7

4-Hydrazino-3-methoxybenzoic acid hydrochloride.

A solution of 2.17 g of $NaNO_2$ in 40 ml of $H_2O$ is added slowly to a solution, cooled to 0° C., of 5 g of 4-amino-3-methoxybenzoic acid in 50 ml of concentrated HCl. After 1 hour 15 minutes of stirring at 0° C., the mixture is cooled to −10° C., and a solution of 23.6 g of $SnCl_2.2H_2O$ in 20 ml of concentrated HCl and 20 ml of water is added over 30 min. After one and a half hours of stirring at −10° C., the mixture is filtered, and the precipitate is washed with 50 ml of pentane to obtain, after drying, 6 g of expected product.

NMR: 3.8:s:3H; 7:d:1H; 7.4:s:1H; 7.5:dd:1H; 8:bs:1H; 10.6:bs:2H.

Preparation 2.8

2-Chloro-4-hydrazinobenzonitrile hydrochloride.

5 g of 4-amino-2-chlorobenzonitrile and 40 ml of concentrated HCl in 30 ml of THF are mixed at −5° C.; 2.26 g of $NaNO_2$ in 30 ml of water are added and the mixture is left stirring for 2 hours, 30 g of $SnCl_2.2H_2O$ in 30 ml of concentrated HCl are then added and stirring is maintained at −5° C. for 30 minutes.

After a return to RT, the insoluble matter is filtered off, NaCl is added and the mixture is stirred again. The expected product crystallizes with NaCl; it is is taken up in ethanol while the NaCl is filtered off. After evaporation of the solvents, 4.25 g of the expected product are obtained.

Preparation 2.9

3-Cyclopropyl-4-hydrazinobenzoic acid hydrochloride.

A) 4-Acetamido-3-cyclopropylbenzonitrile.

1.67 g of CuCN are added to a solution of 4.3 g of 4-bromo-2-cyclopropylacetanilide (prepared according to J. Am. Chem. Soc., 1968, 90 3404) in 100 ml of DMF, and the mixture is heated to reflux for 24 hours. It is poured into 30 ml of water, the resulting mixture is filtered, and the precipitate is washed with water and then stirred for 30 minutes in a mixture of 59 ml of water and 25 ml of ethylenediamine. After extraction with 100 ml of AcOEt, drying over $Na_2SO_4$ and evaporation under vacuum, 2.39 g of the expected product are obtained.

NMR: 0.6:u.c.:2H; 0.9:u.c.:2H; 1.9:u.c.:1H; 2.1:s:3H; 7.3:d:1H; 7.5:dd:1H; 7.8:d:1H; 9.5:bs:1H.

B) 4-Amino-3-cyclopropylbenzonitrile hydrochloride.

A mixture of 2.39 g of the product of step A dissolved in 45 ml of ethanol with 36 ml of water and 5 ml of concentrated HCl is stirred for 12 hours under reflux. The ethanol is evaporated off under vacuum, and the precipitate is filtered off, washed with 1 ml of water and dried under vacuum to obtain 1.5 g of the expected product.

NMR: 0.5:u.c.:2H; 0.9:u.c.:2H; 1.6:u.c.:1H; 6.7:d:1H; 7.1–7.3:mt:2H; 8:bs:2H.

C) 4-Amino-3-cyclopropylbenzoic acid hydrochloride.

1.3 g of the product of step B in 21 ml of 50% KOH are stirred for 29 hours under reflux. After acidification to pH 1 with concentrated HCl, the mixture is filtered and the residue is dried under vacuum to obtain 0.96 g of the expected product.

NMR: 0.5:u.c.:2H; 0.9:u.c.:2H; 1.7:u.c.:1H; 5.9:bs:2H; 6.6:d:1H; 7.4:s:1H; 7.5:mt:1H; 12:bs:1H.

D) 3-cyclopropyl-4-hydrazinobenzoic acid hydrochloride.

A solution of 0.38 g of $NaNO_2$ in 4.5 ml of water is added slowly to a solution, cooled to −5° C., of 0.95 g of the product obtained in step C in 22 ml of concentrated HCl and 21 ml of AcOH, and the mixture is stirred for 1 h 15 min at 0° C. It is cooled to −10° C., and a solution of 3.76 g of $SnCl_2.2H_2O$ in 8 ml of concentrated HCl is added slowly. After 4 hours of stirring at RT, the mixture is filtered, and the residue is washed with 2 ml of concentrated HCl and dried under vacuum to obtain 1 g of expected product.

NMR: 0.6:u.c.:2H; 1:u.c.:2H; 1.9:u.c.:1H; 7.1:d:1H; 7.6:s:1H; 7.8:d:1H; 8.4:s:1H; 10.7:bs:2H.

Preparation 2.10

5-Hydrazino-2-chlorobenzoic acid hydrochloride.

A solution of 2.11 g of NaNO$_2$ in 40 ml of water is added over 30 minutes to a suspension, cooled to −2° C., of 5 g of 5-amino-2-chlorobenzoic acid in 50 ml of concentrated HCl. The solution is stirred for 2 hours at −3° C. and cooled to −10° C., and a solution of 23 g of SnCl$_2$.2H$_2$O in 20 ml of concentrated HCl and 20 ml of water is added over 30 minutes. The mixture is stirred for one and a half hours at 0° C. and filtered, and the precipitate is dried to obtain 4 g of expected product.

NMR: 7.6:bs:2H; 7.7:bs:1H; 8.4:bs:1H; 11.0:bs:3H.

Preparation 2.11

3-Hydrazino-4-methylbenzoic acid hydrochloride.

A solution of 2.74 g of NaNO$_2$ in 28 ml of water is added over 30 minutes to a solution, cooled to −5° C., of 5 g of 3-amino-4-methylbenzoic acid in 120 ml of concentrated HCl and 40 ml AcOH, and the mixture is left stirring for 1 hour 20 minutes at 0° C. After cooling to −10° C., a solution of 27.6 g of SnCl$_2$.2H$_2$O in 28 ml of concentrated HCl is added slowly. After stirring for 1 hour at RT, filtration, washing of the precipitate with 5 ml of 1N HCl and drying over P$_2$O$_5$ under vacuum, 6.15 g of the expected product are obtained.

By working according to the above procedures, starting from correctly substituted aniline derivatives, the hydrazines described in Table 1 below are prepared.

TABLE 1

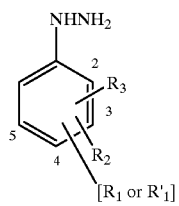

[R$_1$ or R'$_1$]

| Preparation | R$_1$ or R'$_1$ | R$_2$ | R$_3$ | M.p. or NMR (Salt) |
|---|---|---|---|---|
| 2.12 | -4-SO$_3$H | 2-CH$_3$ | 3-CH$_3$ | NMR (H$_2$SO$_4$) |
| 2.13 | 5-CO$_2$H | 2-Cl | H | NMR (HCl) |
| 2.14 | 3-CO$_2$H | 4-F | H | NMR |
| 2.15 | 4-CN | 2-CF$_3$ | H | 125 |
| 2.16 | 4-CO$_2$H | 2-CF$_3$ | H | 170 (dec.) (HCl) |
| 2.17 | 5-CO$_2$H | 2-OCH$_3$ | H | NMR (HCl) |

NMR:

Preparation 2.12:2:s:3H; 2.4:s:3H; 6.5:d:1H; 7.5:d:1H; 9.9:bs:3H.

Preparation 2.13:7.6:bs:2H; 7.7:bs:1H; 8.4:bs:1H; 11.0:bs:3H.

Preparation 2.14:7.3:u.c.:2H; 7.4:u.c.:1H; 8.4:bs:1H; 10.8:bs:3H.

Preparation 2.17:3.8:s:3H; 4.4:bs:1H; 7.0:d:1H; 3.6:d:1H; 10.0:bs:3H.

Preparation 2.18

N-(4-Hydrazino-3-isopropylphenyl)-4-methylbenzenesulphonamide oxalate.

A) N-(2-Bromo-5-isopropyl-4-nitrophenyl)-4-methylbenzenesulphonamide.

A solution of 23.47 g of N-(4-nitrophenyl)-4-methylbenzenesulphonamide in 230 ml of THF is cooled to −30° C., 100 ml of a 2M solution of isopropylmagnesium chloride in ether is added and the mixture is left stirring for 30 minutes at −30° C. 10.3 ml of bromine are then added at −30° C., the mixture is left stirring for 15 minutes at this temperature and the temperature is then allowed to rise to 20° C. 55 ml of triethylamine are then added and the mixture is left stirring for 1 hour at RT. Water is added, the mixture is acidified to pH 3–4 by adding 10% HCl solution, the organic phase is separated after settling has taken place, the aqueous phase is extracted with ether and the combined organic phases are dried over Na$_2$SO$_4$. The organic phase is stirred in the presence of animal charcoal, filtered and concentrated under vacuum. The residue is taken up in EtOH and the crystallized product formed is drained. 11.6 g of the expected product are obtained, m.p.=132° C.

NMR 1.0:d:6H; 2.32:s:3H; 3.12:s:1H; 7.14:s:1H; 7.36:d:2H; 7.65:d:2H; 8.08:s:1H; 10.25:bs:1H.

B) N-(4-Amino-3-isopropylphenyl)-4-methylbenzenesulphonamide.

A mixture of 11.5 g of the compound obtained in the preceding step and 1 g of palladium on charcoal (5% Pd) in 200 ml of MeOH and 30 ml of DMF is hydrogenated for 7 hours at RT and at a pressure of 1 bar. The catalyst is filtered off and the filtrate is concentrated under vacuum. The residue is taken up with water, the mixture is neutralized to pH 7 by adding 10% NaOH solution and extracted with AcOEt, the organic phase is dried over Na$_2$SO$_4$ and the solvent is evaporated off under vacuum. 8 g of the expected product are obtained.

NMR: 1.01:d:6H; 2.4:s:3H; 2.89:mt:1H; 4.91:bs:2H; 6.42–6.68:u.c.:3H; 7.35:d:2H; 7.56:d:2H; 9.38:s:1H.

C) N-(4-Hydrazino-3-isopropylphenyl)-4-methylbenzenesulphonamide oxalate.

A mixture of 6.68 g of the compound obtained in the preceding step and 70 ml of concentrated HCl solution is stirred at 0° C., a solution of 1.48 g of NaNO$_2$ in 5 ml of water is added and the resulting mixture is left stirring for 1 hour at 0° C. A solution of 11.35 g of sodium dithionite in 60 ml of water is then added and stirring is continued for 1 hour at 0° C. 120 g of powdered sodium acetate and 300 ml of water are then added and the reaction mixture is left stirring for 30 minutes at 0° C. It is extracted with AcOEt, the organic phase is dried over Na$_2$SO$_4$ and filtered, a solution of 1.98 g of oxalic acid in a minimum amount of EtOH is added to the filtrate and the mixture is concentrated under vacuum. The residue is taken up in isopropyl ether, the mixture is left stirring for 12 hours and the precipitate formed is drained. 4.84 g of the expected product are obtained, which product is used without further treatment.

Preparation 2.19

1-Hydrazino-2-methyl-4-nitrobenzene hydrofluoride.

A mixture of 4.6 g of 1-fluoro-2-methyl-4-nitrobenzene and 3 ml of hydrazine hydrate in 45 ml of 2-propanol is heated to reflux for 2 hours. 3 ml of hydrazine hydrate are added, refluxing is continued for 2 hours and the mixture is left overnight with stirring at RT. The precipitate formed is drained. 3.53 g of the expected product are obtained, m.p.= 182° C.

Preparation 2.20

N-(4-Hydrazino-3-isobutylphenyl)-4-methylbenzenesulphonamide hydrobromide.

A) N-(2-Bromo-5-isobutyl-4-nitrophenyl)-4-methylbenzenesulphonamide.

This compound is prepared according to the procedure described in step A of Preparation 2.18, from 10 g of N-(4-nitrophenyl)-4-methylbenzenesulphonamide in 100 ml of THF and 42.6 ml of a 2M solution of isobutylmagnesium chloride in ether, followed by 4.4 ml of bromine and 23.4 ml of triethylamine. 5.9 g of the expected product are obtained, m.p.=170° C.

NMR: 0.8:d:6H; 1.7:mt:1H; 2.35:s:3H; 2.6:d:2H; 7.2:s:1H; 7.3:d:2H; 7.4:d:2H; 8.2:s:1H; 10.25:s:1H.

B) N-(4-Amino-3-isobutylphenyl)-4-methylbenzenesulphonamide.

This compound is prepared according to the procedure described in step B of Preparation 2.18, from 4.7 g of the compound obtained in the preceding step. 2.8 g of the expected product are obtained.

NMR: 0.8:d:6H; 1.75:mt:1H; 2.2:d:2H; 2.4:s:3H; 4.8:s:2H; 6.45:d:1H; 6.5:d:1H; 6.65:dd:1H; 7.35:d:2H; 7.55:d:2H; 9.4:s:1H.

C) N-(4-Hydrazino-3-isobutylphenyl)-4-methylbenzenesulphonamide hydrobromide.

This compound is prepared according to the procedure described in step C of Preparation 2.18, from 2.5 g of the compound obtained in the preceding step, 35 ml of concentrated HC1, 50 ml of acetic acid and 0.53 g of NaNO$_2$, followed by 4.78 g of sodium dithionite in 50 ml of water, 140 g of sodium acetate and 70 ml of water. After 30 minutes of stirring at 0° C., hydrobromic acid is added at 0° C. and the crystallized product is drained and dried. 1.9 g of the expected product are obtained.

NMR: 0.65:d:6H; 1.6:mt:1H; 2.05:d:2H; 2.2:s:3H; 6.05:bs:1H; 6.4:bs:1H; 6.6–6.8:u.c.:2H; 7.2:d:2H; 7.4:d:2H.

Preparation 2.21

N-(4-Hydrazino-3-cyclopentylphenyl)-4-methylbenzenesulphonamide oxalate.

A) N-(2-Bromo-5-cyclopentyl-4-nitrophenyl)-4-methylbenzenesulphonamide.

This compound is prepared according to the procedure described in step A of Preparation 2.18, from 15 g of N-(4-nitrophenyl)-4-methylbenzenesulphonamide in 100 ml of THF and 64 ml of a 2M solution of cyclopentylmagnesium chloride in ether, followed by 6.8 ml of bromine and 35 ml of triethylamine. 6.1 g of the expected product are obtained, m.p.=122° C.

NMR (DMSO+TFA): 1.25:mt:2H; 1.5–1.7:u.c.:4H; 1.95:mt:2H; 2.36:s:3H; 3.2:qt:1H; 7.12:s:2H; 7.4:d:2H; 7.7:d:2H; 8.08:s:1H.

B) N-(4-Amino-3-cyclopentylphenyl)-4-methylbenzenesulphonamide.

This compound is prepared according to the procedure described in step B of Preparation 2.18, from 6 g of the compound obtained in the preceding step. 4.25 g of the expected product are obtained, m.p.=128° C.

NMR (DMSO+TFA): 1.25:mt:2H; 1.5–1.75:u.c.:4H; 1.95:mt:2H; 2.3:s:3H; 3.0:qt:1H; 7.0:dd:1H; 7.12:d:1H; 7.2:d:1H; 7.34:d:2H; 7.65:d:2H.

C) N-(4-Hydrazino-3-cyclopentylphenyl)-4-methylbenzenesulphonamide oxalate.

This compound is prepared according to the procedure described in step C of Preparation 2.18, from 3.35 g of the compound obtained in the preceding step, 20 ml of H$_2$SO$_4$, 50 ml of acetic acid, 10 ml of water and 0.69 g of NaNO$_2$, followed by 5.5 g of sodium dithionite in 50 ml of water and 200 g of sodium acetate and 300 ml of water. 2.42 g of the expected product are obtained.

Preparation 2.22

4-Hydrazino-2-isopropylbenzoic acid hydrochloride.

A) 4-Iodo-3-isopropylacetanilide.

This compound is prepared according to the process described in Bull. Soc. Chim. Jap., 1989, 62, 1349.

5.7 g of zinc chloride and 10.8 g of benzyltrimethylammonium dichloroiodate are added at RT to a solution of 5 g of 3-isopropylacetanilide in 150 ml of acetic acid, and the mixture is left stirring for 2 days. It is concentrated under vacuum, the residue is taken up with 100 ml of a 5% solution of sodium hydrogen sulphite, the mixture is brought to pH 5–6 by adding 10% Na$_2$CO$_3$ solution and extracted 4 times with 200 ml of chloroform and the organic phase is dried over Na$_2$SO$_4$. After filtration, the filtrate is chromatographed on 100 g of alumina, eluting with chloroform. 5.2 g of the expected product are obtained.

NMR: 1.1:d:6H; 2.0:s:3H; 3.06:u.c.:1H; 7.28:dd:1H; 7.5:d:1H; 7.72:d:1H; 10.0:bs:1H.

B) 4-Iodo-3-isopropylaniline.

A mixture of 5.1 g of the compound obtained in the preceding step in 40 ml of 96% EtOH and 25 ml of concentrated NaOH is heated to reflux for 6 hours. It is concentrated under vacuum and extracted with ether, the organic phase is dried over Na$_2$SO$_4$ and the solvent is evaporated off under vacuum. 5 g of the expected product are obtained in the form of an oil.

NMR: 1.16:d:6H; 2.94:u.c.:1H; 5.2:bs:2H; 6.2:dd:1H; 6.6:d:1H; 7.4:d:1H.

C) 4-Amino-2-isopropylbenzoic acid.

40 ml of water and 11 g of K$_2$CO$_3$ are added to a solution of 5 g of the compound obtained in the preceding step in 60 ml of DMF, and the solution is then degassed for 10 minutes by bubbling nitrogen through it. 0.5 g of palladium(II) acetate are then added and the reaction mixture is thereafter degassed for 10 minutes by bubbling nitrogen through it. It is placed under a pressure of 1 bar of carbon monoxide for 10 hours and with stirring. The solution is filtered, the filter is washed 4 times with 20 ml of water and the filtrate is concentrated under vacuum. The residue is taken up with 50 ml of water and 10 ml of saturated NaCl solution, the aqueous phase is washed with ether and acidified to pH 3.5–4 by adding concentrated HCl and extracted with AcOEt, the organic phase is washed with saturated NaCl solution and dried over Na$_2$SO$_4$ and the solvent is evaporated off under vacuum. 2 g of a crude product are obtained, which product is taken up in 20 ml of a saturated solution of HCl gas in methanol, and the mixture is heated to reflux overnight. It is concentrated under vacuum, the residue is taken up in 20 ml of water, and the mixture is alkalinized to pH 8 by adding concentrated NaOH and extracted with 30 ml of DCM. 0.8 ml of acetic anhydride, NaHCO$_3$ and Na$_2$SO$_4$ are added to the organic phase, which is left stirring. After filtration, the filtrate is concentrated under vacuum and the residue is chromatographed on silica, eluting with a DCM/ether (50:50; v/v) mixture. 0.8 g of 4-acetamido-2-isopropylbenzoic acid methyl ester is obtained in the form of an oil. A mixture of 0.8 g of the product obtained and 3 g of KOH in 10 ml of water and 2 ml of 1,2-dimethoxyethane is heated to reflux overnight. After cooling to RT, the reaction mixture is washed with ether, the aqueous phase is acidified to pH 3–4 by adding concentrated HCl and extracted with AcOEt, the organic phase is dried over Na$_2$SO$_4$ and the solvent is evaporated off under vacuum. 0.6 g of the expected product is obtained.

NMR: 1.17:d:6H; 4.0:sp:1H; 5.7:bs:2H; 6.36:dd:1H; 6.80:d:1H; 7.6:d:1H; 11.80:bs:1H.

D) 4-Hydrazino-2-isopropylbenzoic acid hydrochloride.

A mixture of 0.5 g of the compound obtained in the preceding step in 7 ml of concentrated HCl is cooled to 0° C., a solution of 0.23 g of $NaNO_2$ in 4 ml of water is added and the resulting mixture is left stirring for 1 hour 30 minutes at 0° C. It is cooled to −10° C. and a solution of 2.6 g of $SnCl_2.2H_2O$ in 5 ml of concentrated HCl and 3 ml of water is added, and the resulting mixture is left stirring for 2 hours at 0° C. The precipitate formed is drained, washed with concentrated HCl and dried at 50° C. under vacuum. 0.36 g of the expected product is obtained.

NMR: 1.15:d:6H; 3.98:u.c.:1H; 6.7:dd:1H; 6.96:d:1H; 7.8:d:1H; 8.2:bs:1H; 13:bs:4H.

Preparation 2.23

1-Hydrazino-4-nitro-5,6,7,8-tetrahydronaphthalene hydrochloride.

A) 1-Acetamido-5,6,7,8-tetrahydronaphthalene.

A mixture of 24.39 g of 1-amino-5,6,7,8-tetrahydronaphthalene and 18.6 ml of acetic anhydride in 230 ml of DCM is left stirring for 1 hour at RT. It is concentrated under vacuum, the residue is taken up with ether and the precipitate formed is drained. 26.8 g of the expected product are obtained, m.p.=158° C.

B) 1-Amino-4-nitro-5,6,7,8-tetrahydronaphthalene.

A mixture of 13 g of the compound obtained in the preceding step in 72 ml of concentrated sulphuric acid is cooled to 0° C., a mixture of 4.55 ml of nitric acid (d=1.4) and 22 ml of concentrated sulphuric acid is added and the resulting mixture is left stirring for 45 minutes at 0° C. The reaction mixture is poured onto ice and the precipitate formed is drained. The precipitate is taken up in 145 ml of EtOH, 30 ml of concentrated HCl and 30 ml of water and the mixture is heated to reflux for 1 hour 30 minutes. 70 ml of the reaction mixture are evaporated, 220 ml of water are added to the remaining solution, the pH is brought to 7 by adding concentrated ammonium hydroxide solution and the precipitate formed is drained and dried. The precipitate is taken up with 210 ml of nitrobenzene, the mixture is cooled to 0° C. and a stream of HCl gas is bubbled through it for 50 minutes. The precipitate formed is drained and washed with ether. The precipitate is taken up with MeOH, the mixture is neutralized by adding concentrated ammonium hydroxide solution, water is added and the precipitate is drained. 5.15 g of the expected product are obtained after drying, m.p.=114° C.

C) 1-Hydrazino-4-nitro-5,6,7,8-tetrahydronaphthalene hydrochloride.

A mixture of 3.8 g of the compound obtained in the preceding step in 70 ml of concentrated HCl is cooled to 3° C., a solution of 1.34 g of $NaNO_2$ in 2 ml of water is added and the resulting mixture is left stirring for 2 hours at 3° C. A solution of 18.2 g of $SnCl_2.2H_2O$ in 90 ml of concentrated HCl is then added, the mixture is left stirring for 30 minutes at 3° C. and the temperature is then allowed to rise to RT. The precipitate formed is drained and dried. 6.3 g of the expected product are obtained, mixed with tin salts.

NMR (DMSO+TFA): 1.7:mt:4H; 2.55:mt:2H; 2.85:mt:2H; 6.88:d:1H; 7.85:d:1H.

Preparation 2.24

3-Diethylamino-N-(4-isopropyl-3-hydrazinophenyl) propionamide.

A) 3-Diethylamino-N-(4-isopropyl-3-nitrophenyl) propionamide oxalate.

4 g of 4-isopropyl-3-nitroaniline (prepared according to J. Org. Chem., 1954, 19, 1067) are treated by heating to reflux for 1 hour with 8.14 ml of bis(trimethylsilyl)acetamide in 20 ml of acetonitrile, and the acid chloride prepared from 4 g of 3-(N,N-diethylamino)propanoic acid hydrochloride in DCM is added, followed by 8.9 ml of triethylamine. After 1 hour of stirring at RT, the mixture is evaporated to dryness, the residue is extracted with DCM, and the mixture is washed with water and then with 5% NaOH. After drying over $Na_2SO_4$, the mixture is evaporated under vacuum, the oil obtained is redissolved in the minimum amount of ethanol, and 1.2 g of oxalic acid are added. After 2 hours of stirring, the mixture is filtered to obtain 4.5 g of the expected oxalate, m.p.=165° C.

B) 3-Diethylamino-N-(4-isopropyl-3-aminophenyl) propionamide oxalate.

A solution of 4.5 g of nitro derivative obtained in the preceding step in 100 ml of MeOH and 10 ml of DMF is hydrogenated for 5 hours with Raney® nickel. After the catalyst has been filtered off, the mixture is concentrated under vacuum, precipitation is induced by adding isopropyl ether and the mixture is left stirring for 1 hour at RT. After filtration, 3 g of the expected aniline oxalate are obtained, m.p.=127° C.

C) 3-Diethylamino-N-(4-isopropyl-3-hydrazinophenyl) propionamide.

0.67 g of $NaNO_2$ dissolved in the minimum amount of water is added to a mixture, cooled to 0° C., of 2.7 g of amine obtained in the preceding step and 30 ml of concentrated HCl, and the resulting mixture is left stirring for 1 hour at 0° C. 5 g of sodium dithionite dissolved in the minimum amount of water are then added and the mixture is stirred for a further 30 minutes at 0° C. 50 g of powdered sodium acetate are added and the mixture is stirred for 30 minutes at 0° C. 50 g of water are added and a few impurities are extracted with AcOEt. The aqueous phase is saturated with NaCl, the pH is raised to 9 with 20% $NH_4OH$ and extracted with DCM, and the organic phase is dried over $Na_2SO_4$ and evaporated under vacuum. The residue is allowed to crystallize in pentane overnight and is filtered off to obtain 3.26 g of expected hydrazine, m.p.=77–80° C.

PREPARATIONS OF THE ESTERS IIa, II'a

Preparation 3.1

1-(4-Carboxy-2-isopropylphenyl)-5-(2,6-dimethoxyphenyl)-3-pyrazolecarboxylic acid methyl ester.

(II'a: $R'_1$=4-$CO_2H$; $R_2$=2-iPr; $R_3$=H; $R_4$=$CH_3$).

A mixture containing 0.96 g of the product obtained in Preparation 2.1 and 1.2 g of compound A obtained in Preparation 1.1 in 15 ml of acetic acid is brought to reflux for 5 hours. After 3 days at RT, it is poured into a mixture of water and ice. The precipitate formed is filtered off, rinsed with water and then dried over $P_2O_5$. 1.34 g of the expected product are obtained, m.p.=228–230° C.

NMR: 0.85:d:6H; 2.55:sp:1H; 3.5:s:6H; 3.75:s:3H; 6.5:d:2H; 6.75:s:1H; 7.05–7.3:u.c.:2H; 7.7:d:1H; 13.05:bs:1H.

Preparation 3.1a 1-(4-Carboxy-2-isopropylphenyl)-5-(2,6-dimethoxyphenyl)-3-pyrazolecarboxylic acid ethyl ester.

By reacting the product of Preparation 2.1 or 2.1a with compound A1 according to the procedure of Preparation 3.1, and after recrystallization in AcOEt, the expected ethyl ester is obtained, m.p.=231° C.

Preparation 3.2

1-[4-[N-Methyl-N-(3-(N',N'-dimethylamino)propyl) carbamoyl]-2-isopropylphenyl]-5-(2,6-dimethoxyphenyl)-3-pyrazolecarboxylic acid methyl ester.

(IIa: $R_1$=4—CON(CH$_3$)(CH$_2$)$_3$NMe$_2$; $R_2$=2-iPr; $R_3$=H; $R_4$=CH$_3$).

A) 1-(4-Chloroformyl-2-isopropylphenyl)-5-(2,6-dimethoxyphenyl)-3-pyrazolecarboxylic acid methyl ester.

A mixture is prepared containing 26 g of the product obtained in Preparation 3.1 and 170 ml of thionyl chloride. It is left stirring at RT for 1 day. It is evaporated under vacuum, the residue is taken up with DCM, the mixture is evaporated and the operation is repeated 3 times.

B) 1-[4-[N-Methyl-N-(3-(N',N'-dimethylamino)propyl) carbamoyl]-2-isopropylphenyl]-5-(2,6-dimethoxyphenyl)-3-pyrazolecarboxylic acid methyl ester.

9.3 ml of triethylamine and 9.9 ml of N,N,N'-trimethyl-1,3-propanediamine are added to 50 ml of DCM. The product obtained in the preceding step in 280 ml of DCM is added under nitrogen, and the mixture is left stirring at RT for three and a half hours. After washing with water (twice), the mixture is dried over MgSO$_4$ and evaporated under vacuum. The residue is taken up with ether. After the insoluble matter has been filtered off, and evaporation, the residue is chromatographed on silica, eluting with DCM/MeOH/H$_2$O (95:5:0.5; v/v/v, to 88:12:0.8; v/v/v). 24.5 g of the expected product are obtained.

NMR: 0.95:d:6H; 1.7:u.c.:2H; 1.9–2.4:u.c.:8H; 2.95:ss:3H; 3.5:u.c.:2H; 3.7:s: 6H; 3.9:s:9H; 6.7:d:2H; 6.9:s:1H; 7.1–7.5:u.c.:4H.

Preparation 3.2a

1-[4-[N-Methyl-N-(3-(N',N'-dimethylamino)propyl) carbamoyl]-2-isopropylphenyl]-5-(2,6-dimethoxyphenyl)-3-pyrazolecarboxylic acid ethyl ester.

A) 1-(4-Chloroformyl-2-isopropylphenyl)-5-(2,6-dimethoxyphenyl)-3-pyrazolecarboxylic acid ethyl ester.

26 g of the product of Preparation 3.1 or 3.1a are added to 50 ml of SOCl$_2$ cooled to 5°, and the mixture is stirred for 5 hours at RT while nitrogen is bubbled through in the dry state. After evaporation under vacuum, the residue is taken up with DCM and evaporated under vacuum; the operation is repeated twice.

The acid chloride may also be prepared according to the procedure A' below:

A') 2.5 ml of SOCl$_2$ is added to a solution of 5 g of the product of Preparation 3.1 or 3.1a in 50 ml of DCM, and the mixture is heated to reflux for 3 hours and evaporated under vacuum, the residue is taken up with DCM and the mixture is evaporated under vacuum; the operation is carried out twice.

B) 1-[4-[N-Methyl-N-(3-(N',N'-dimethylamino)propyl) carbamoyl]-2-isopropylphenyl]-5-(2,6-dimethoxyphenyl)-3-pyrazolecarboxylic acid ethyl ester.

A solution of acid chloride obtained in step A in 220 ml of DCM is added under dry nitrogen to a solution of 9 ml of triethylamine and 9.5 ml of N,N,N'-trimethyl-1,3-propanediamine in 50 ml of DCM, and the mixture is stirred overnight. It is washed twice with water and the aqueous phases are extracted twice with DCM. The combined organic phases are dried over MgSO$_4$ and evaporated under vacuum. The residue is stirred with 300 ml of ether, some insoluble matter is filtered off, and the filtrate is decolorized on animal charcoal and evaporated to obtain 28.8 g of the expected product in the form of an oil.

NMR (DMSO+TFA): 1:d:6H; 1.3:t:3H; 1.8–2.1:u.c.:2H; 2.65:qt:1H; 2.7–3.05:u.c.:9H; 3.15:mt: 2H; 3.5:mt:2H; 3.65:s:6H; 4.35:qr:2H; 6.6:d:2H; 6.85:s:1H; 7.2–7.4:u.c.:4H.

The product of step B may also be obtained according to the procedure described below:

B') A solution of the acid chloride obtained in step A' in 37.5 ml of DCM is added to a solution of 1.32 g of N,N,N'-trimethyl-1,3-propanediamine in 37.5 ml of 3N sodium hydroxide. After 1 hour of stirring, 25 ml of chloroform and 25 ml of water are added, settling is allowed to take place, and the organic phase is separated, dried over Na$_2$SO$_4$ and evaporated under vacuum to obtain 6.1 g of the expected product.

Preparation 3.3

1-[4-[N-(2-Cyanoethyl)carbamoyl]-2-isopropylphenyl]-5-(2,6-dimethoxyphenyl)-3-pyrazolecarboxylic acid methyl ester.

(IIa: $R_1$=4-CONHCH$_2$CH$_2$CN; $R_2$=2-iPr; $R_3$=H; $R_4$=CH$_3$).

0.935 g of 3-aminopropionitrile hemifumarate is mixed with 3.7 ml of 1.3N NaOH, the mixture is extracted with DCM, the organic phase is dried over Na$_2$SO$_4$ and the solvent is evaporated off under vacuum. The residue is taken up in 6 ml of DCM, 0.96 ml of triethylamine is added, and a solution of 2.45 g of the compound obtained in step A of Preparation 3.2 in 30 ml of DCM is then added slowly. The mixture is left stirring overnight at RT and under a nitrogen atmosphere. Some insoluble matter is filtered off, the filtrate is washed with water, with saturated NaHCO$_3$ solution and with water and dried over Na$_2$SO$_4$, and the solvent is evaporated off under vacuum. 2.24 g of the expected product are obtained, m.p.=114–116° C. (dec.).

NMR: 1:d:6H; 2.7:mt:1H; 2.8:t:2H; 3.5:q:2H; 3.65:s:6H; 3.9:s:3H; 6.7:d:2H; 6.9:s:1H; 7.3–7.4:u.c.:2H; 7.75:d:1H; 7.9:s:1H; 9:t:1H.

By reacting the appropriate primary amine with the compound obtained in Preparation 3.2, step A, and working according to the procedure described for Preparation 3.2, step B, the esters described in Table 2 below are prepared.

TABLE 2

(IIa)

[Structure: pyrazole with CO$_2$CH$_3$ group, OCH$_3$ and CH$_3$O substituted phenyl, and iPr/R$_1$ substituted phenyl]

| Preparation | R$_1$ | M.p. ° C. or NMR |
|---|---|---|
| 3.4 | —CONH(CH$_2$)$_3$NMe$_2$ | NMR |
| 3.5 | —CONH(CH$_2$)$_2$NMe$_2$ | NMR |
| 3.6 (IIa. HCl) | —CONH(CH$_2$)$_3$NEt$_2$ | NMR |
| 3.7 | —CONH(CH$_2$)$_2$N[pyrrolidine] | NMR |
| 3.8 | —CONH—[pyridyl] | NMR |

TABLE 2-continued

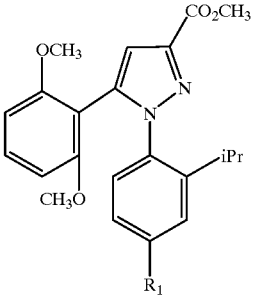

| Preparation | $R_1$ | M.p. °C. or NMR |
|---|---|---|
| 3.9 | —CONH—CH$_2$—C(Me)(Me)—CH$_2$—NMe$_2$ | NMR |
| 3.10 | —CONH—[4-(N-CH$_2$C$_6$H$_5$)piperidinyl] | NMR |
| 3.11 | —CONH—[quinuclidinyl] | NMR |

NMR:

Preparation 3.4:1:d:6H; 1.65:mt:2H; 2.1:s:6H; 2.25:t:2H; 2.6:mt:1H; 3.25:u.c.:2H; 3.6:s:6H; 3.85:s:3H; 6.6:d:2H; 6.85:s:1H; 7.2–7.3:u.c.:2H; 7.6:dd:1H; 7.8:d:1H; 8.6:t:1H.

Preparation 3.5: (DMSO+TFA) 1:d:6H; 2.6:mt:2H; 2.8:s:6H; 3.25:mt:2H; 3.6:u.c.+s:8H; 3.85:s:3H; 6.6:d:2H; 6.8:s:1H; 7.2–7.4:u.c.:2H; 7.7:d:1H; 7.8:d:1H.

Preparation 3.6: (DMSO+TFA): 0.9:d:6H; 1.15:t:6H; 1.8–2:u.c.:2H; 2.6:mt:1H; 3.1:mt:4H; 3.3:t:2H; 3.55:u.c.+ s:8H; 3.8:s:3H; 6.5:d:2H; 6.8:s:1H; 7.15–7.3:u.c.:2H; 7.6:dd:1H; 7.8:bs:1H.

Preparation 3.7: 1.05:d:6H; 1.7:mt:4H; 2.45–2.75:u.c.:7H; 3.4:mt:2H; 3.7:s:6H; 3.9:s:3H; 6.65:d:2H; 6.9:s:1H; 7.3–7.4:u.c.:2H; 7.7–7.9:u.c.:2H; 8.6:t:1H.

Preparation 3.8: 1.05:d:6H; 2.7:mt:1H; 3.7:s:6H; 3.9:s:3H; 6.7:d:2H; 6.9:s:1H; 7.2–7.4:u.c.:3H; 7.85–8.5:u.c.:5H; 11:s:1H.

Preparation 3.9: 0.9:s:6H; 1.05:d:6H; 2.25:s:2H; 2.3:s:6H; 2.7:mt:1H; 3.2:d:2H; 3.7 s:6H; 3.9:s:3H; 6.65:d:2H; 6.9:bs:1H; 7.3–7.4:u.c.:2H; 7.6–7.8:u.c.:2H; 8.7:t:1H.

Preparation 3.10: 1:d:6H; 1.4–1.9:u.c.:4H; 2:t:2H; 2.6:mt:1H; 2.8:d:2H; 3.5:s:2H; 3.6:s:6H; 3.6–3.85:u.c.:1H; 3.85:s:3H; 6.6:d:2H; 6.85:s:1H; 7.1–7.4 u.c.:5H; 7.65:d:1H; 7.8:s:1H; 8.3:d:1H.

Preparation 3.11 (DMSO+TFA): 1.05:d:6H; 1.6–2.3:u.c.:5H; 2.7:mt:1H; 3.2–3.4:u.c.:5H; 3.5–3.8:u.c.+ s:7H; 3.9:s:3H; 4.3–4.4:u.c.:1H; 6.65:d:2H; 6.9:s:1H; 7.3–7.4:mt:2H; 7.8:d:1H; 7.9:s:1H.

Preparation 3.12

5-(2,6-Dimethoxyphenyl)-1-(2-isopropyl-4-sulphophenyl)-3-pyrazolecarboxylic acid methyl ester.

(II'a: R'$_1$=4-SO$_3$H; R$_2$=2-iPr; R$_3$=H; R$_4$=CH$_3$).

A mixture containing 0.82 g of 3-isopropyl-4-hydrazinobenzenesulphonic acid obtained in Preparation 2.2 and 1.26 g of compound A obtained in Preparation 1.1 in 15 ml of acetic acid is heated to reflux for 5 hours. After evaporation, the residue is dissolved in DCM, and the solution is washed with normal HCl and decolorized on activated charcoal. It is dried and evaporated, the residue is then stirred under reflux in isopropyl ether and the mixture is filtered while hot. 1.28 g of the expected product are obtained.

NMR: 1:d:6H; 2.6:mt:1H; 3.6:s:6H; 3.8:s:3H; 6.6:d:2H; 6.8:s:1H; 7.15:d:1H; 7.3:t:1H; 7.4:d:1H; 7.5:s:1H.

Preparation 3.13

5-(2,6-Dimethoxyphenyl-1-[2-isopropyl-4-(N-methyl-N-(3-(N',N'-dimethylamino)propyl)aminosulphonyl)phenyl]-3-pyrazolecarboxylic acid methyl ester.

(IIa: R$_1$=-4-SO$_2$NMe(CH$_2$)$_3$NMe$_2$; R$_2$=2-iPr; R$_3$=H; R$_4$=CH$_3$).

A) 5-(2,6-Dimethoxyphenyl)-1-(4-chlorosulphonyl-2-isopropylphenyl)-3-pyrazolecarboxylic acid methyl ester.

1.08 g of the product obtained in Preparation 3.12 and 4 ml of POCl$_3$ are left stirring at RT for 24 hours, and stirring is then continued at 70° C. for a further 24 hours. The reaction medium is evaporated twice with toluene and 1.6 g of the expected product are obtained.

B) 5-(2,6-Dimethoxyphenyl)-1-[2-isopropyl-4-(N-methyl-N-(3-(N',N'-dimethylamino)propyl)aminosulphonyl)phenyl]-3-pyrazolecarboxylic acid methyl ester.

1.8 ml of N,N,N'-trimethyl-1,3-propanediamine and then 2 ml of triethylamine are added to a suspension of 1.6 g of the product obtained in the preceding step in 10 ml of toluene and 5 ml of DCM. The mixture is left stirring for 3 hours at RT and then one and a half hours at 50° C. After filtration and evaporation to dryness, the residue is extracted with ether and then with AcOEt. The organic phase is washed with water, dried over Na$_2$SO$_4$ and evaporated under vacuum. 1.13 g of the expected product are obtained.

NMR: 0.85:d:6H; 1.45:mt:2H; 2:s:6H; 2.6:s+mt:4H; 2.85:t:2H; 3.5:s:6H; 3.8:s:3H; 6.5:d:2H; 6.8:s:1H; 7.2:t:1H; 7.4:d:1H; 7.5–7.6:u.c.:2H.

Preparation 3.14

5-(2,6-Dimethoxyphenyl)-1-(4-carboxy-5,6,7,8-tetrahydro-1-naphthyl)-3-pyrazolecarboxylic acid methyl ester.

(II'a: R'$_1$=4-CO$_2$H; R$_2$, R$_3$=—(CH$_2$)$_4$—; R$_4$=CH$_3$).

A mixture of 0.67 g of hydrazine obtained in Preparation 2.3 and 0.83 g of compound A in 6 ml of AcOH is stirred under reflux for 2 hours. It is extracted with DCM, and the organic phase is washed with water, dried over MgSO$_4$ and evaporated under vacuum. The residue is chromatographed on silica, eluting with a DCM/MeOH (100:2; v/v) mixture to obtain 0.7 g of expected product.

NMR: 1.4–2:u.c.:4H; 2.3–3.1:u.c.:4H; 3.4–4:u.c. 9H; 6.6:d:2H; 6.8–7.6:u.c.:4H; 12.95:bs:1H.

Preparation 3.15

5-(2,6-Dimethoxyphenyl)-1-{4-[N-(3-(N',N'-dimethylamino)propyl)carbamoyl]-5,6,7,8-tetrahydro-1-naphthyl)-3-pyrazolecarboxylic acid methyl ester.

(IIa: R$_1$=4-CONH(CH$_2$)$_3$NMe$_2$; R$_2$, R$_3$=—(CH$_2$)$_4$—; R$_4$=CH$_3$).

A solution of 0.7 g of product obtained in Preparation 3.14 in 6 ml of $SOCl_2$ and 30 ml of DCM is heated for one and a half hours at 40° C. It is evaporated under vacuum, the acid chloride is then redissolved in 5 ml of DCM, the mixture is cooled to 5° C. and 0.225 ml of N,N-dimethylpropylenediamine and 0.225 ml of triethylamine are added. After stirring for 2 hours at RT, the mixture is evaporated under vacuum, the residue is redissolved in DCM, and the mixture is washed with water, dried over $MgSO_4$ and evaporated under vacuum to obtain 0.79 g of expected product.

Preparation 3.16

5-(2,6-Dimethoxyphenyl)-1-(4-sulpho-5,6,7,8-tetrahydro-1-naphthyl)-3-pyrazolecarboxylic acid methyl ester.

(II'a: $R'_1$=4-$SO_3H$; $R_2$, $R_3$=—$(CH_2)_4$—; $R_4$=$CH_3$).

A mixture of 0.5 g of hydrazine obtained in Preparation 2.4 and 0.62 g of compound A in 4 ml of AcOH is heated to reflux for four and a half hours. It is evaporated under vacuum, the residue is redissolved in DCM, and the mixture is washed twice with 1N HCl dried over $MgSO_4$ and evaporated to obtain 1 g of expected product.

NMR: 1.7:bs:4H; 2.5:u.c.:2H; 3.2:u.c.:2H; 3.7:s:6H; 3.95:s:3H; 6.7:d:2H; 6.8–6.9:u.c.:2H; 7.35:t:1H; 7.55:d:1H.

Preparation 3.17

5-(2,6-Dimethoxyphenyl)-1-{4-[N-methyl-N-(2-(N',N'-dimethylamino)ethyl)aminosulphonyl]-5,6,7,8-tetrahydro-1-naphthyl}-3-pyrazolecarboxylic acid methyl ester.

(IIa: $R_1$=4-$SO_2NMe(CH_2)_2NMe_2$; $R_2$, $R_3$=$(CH_2)_4$; $R_4$=$CH_3$).

A mixture containing 1 g of acid obtained in Preparation 3.16 and 3 ml of $POCl_3$ is stirred for 5 hours at RT and then three and a half hours at 70° C. It is evaporated under vacuum, toluene is added and the mixture is evaporated under vacuum (twice). The solution of the sulphonyl chloride thereby obtained in 10 ml of DCM is added to a solution of 1.5 ml of N,N,N'-trimethylethylenediamine and 1.5 ml of triethylamine in 10 ml of DCM at 5° C. The mixture is left stirring for 4 days at 10° C., filtered and evaporated under vacuum. After redissolution in DCM, washing with water and extraction of the aqueous phase with DCM, the organic phase is dried over $MgSO_4$ and evaporated under vacuum to obtain 1.07 g of expected sulphonamide, m.p.=90° C.

NMR: 1.6–1.8:u.c.:4H; 2.1:s:6H; 2.35:t:2H; 2.4–2.6:u.c. 2H; 2.9:s:3H; 3.1:mt:2H; 3.2:t:2H; 3.6:s:6H; 3.9:s:3H; 6.7:d:2H; 6.9:s:1H; 7.1:d:1H; 7.4:t:1H; 7.7:d:1H.

Preparation 3.18

5-(2,6-Dimethoxyphenyl)-1-(4-carbamoyl-2-methylphenyl)-3-pyrazolecarboxylic acid methyl ester.

(IIa: $R_1$=4-$CONH_2$; $R_2$=2-$CH_3$; $R_3$=H; $R_4$$CH_3$).

A suspension of 0.39 g of the hydrazine obtained in Preparation 2.5 and 450 mg of compound A in 5 ml of AcOH is heated to reflux for 8 hours. 100 ml of water are added to the reaction medium; the precipitate formed is filtered off, then placed in 10 ml of isopropyl ether and heated to reflux for 30 minutes, and is filtered off. 300 mg of the expected product are obtained, m.p.=219° C. On filtration of the aqueous phase 24 hours later, a second crop of 70 mg of expected product are obtained in the form of needles.

NMR: 2.05:s:3H; 3.5:s:6H; 3.8:s:3H; 6.6:d:2H; 6.8:s:1H; 7:d:1H; 7.2:t:1H; 7.4:bs:1H; 7.6:d:1H; 7.7:s:1H; 7.9:bs:1H.

Preparation 3.19

5-(2,6-Dimethoxyphenyl)-1-(4-carboxy-2,3-dimethylphenyl)-3-pyrazolecarboxylic acid methyl ester.

(II'a: $R'_1$=4-$CO_2H$; $R_2$=2-$CH_3$; $R_3$=3-$CH_3$; $R_4$=$CH_3$).

A mixture of 4.5 g of the product of Preparation 2.6 and 12 g of compound A in 50 ml of AcOH is heated to reflux with stirring for 3 hours. Precipitation is induced by pouring the mixture into 300 ml of ice-cold water, and the precipitate is filtered off and washed with 50 ml of water. After stirring in 50 ml of ether, filtration and drying under vacuum over $P_2O_5$, 5 g of expected product are obtained, m.p.=240° C.

Preparation 3.20

5-(2,6-Dimethoxyphenyl)-1-{2,3-dimethyl-4-[N-(2-(N',N'-dimethylamino)ethyl)carbamoyl]phenyl}-3-pyrazolecarboxylic acid methyl ester.

(IIa: $R_1$=4-$CONH(CH_2)_2NMe_2$; $R_2$=2-$CH_3$; $R_3$=3-$CH_3$; $R_4$=$CH_3$).

After a solution of 2 g of the product of Preparation 3.19 in 10 ml of $SOCl_2$ and 40 ml of DCM has been heated for one and a half hours at 40° C., it is evaporated under vacuum, the acid chloride is redissolved in 10 ml of DCM and the mixture is poured into a solution of 0.54 ml of N,N-dimethylaminoethylenediamine in 10 ml of DCM. 0.68 ml of triethylamine is added and the mixture is stirred for 2 hours at RT. After evaporation under vacuum, extraction with 100 ml of DCM, washing with water, drying over $MgSO_4$ and evaporation under vacuum, 1.8 g of expected product are obtained.

NMR: 1.9:s:3H; 2.2:s+s:9H; 2.4:t:2H; 3.4:u.c.:2H; 3.6:s:6H; 3.8:s:3H; 6.6:d:2H; 6.8:s:1H; 6.9–7.1:dd:2H; 7.3:t:1H; 8.2:t:1H.

Preparation 3.21

5-(2,6-Dimethoxyphenyl)-1-(4-carboxy-2-methoxyphenyl)-3-pyrazolecarboxylic acid methyl ester.

(II'a: $R'_1$=4-$CO_2H$; $R_2$=2-$OCH_3$; $R_3$=H; $R_4$=$CH_3$).

A mixture of 4.8 g of the product of Preparation 2.7 and 5.6 g of compound A in 60 ml of AcOH is left stirring for 6 hours under reflux. After precipitation with 300 ml of ice-cold water, stirring for 30 minutes, filtration, washing with water and then with pentane and drying, 6 g of expected product are obtained, m.p.=210° C.

Preparation 3.22

5-(2,6-Dimethoxyphenyl)-1-{4-[N-methyl-N-(2-(N',N'-diethylamino)ethyl)carbamoyl]-2-methoxyphenyl}-3-pyrazolecarboxylic acid methyl ester.

(IIa: $R_1$=4-$CONMe(CH_2)_2NEt_2$; $R_2$=2-$OCH_3$; $R_3$=H; $R_4$=$CH_3$).

A solution of 2.5 g of the product of Preparation 3.21 in 30 ml of DCM and 5 ml of $SOCl_2$ is heated to reflux for three and a half hours. After evaporation under vacuum followed by 2 azeotropic evaporations with 20 ml of DCM, the acid chloride formed is redissolved in 40 ml of DCM, and the mixture is added to a solution of 1.1 ml of N,N-diethyl-N'-methylethylenediamine and 1 ml of triethylamine in 40 ml of DCM and left stirring for 15 hours at RT. After evaporation under vacuum, the residue is chromatographed on silica, eluting with a solvent gradient ranging from a DCM/ MeOH (90:10; v/v) mixture to a DCM/MeOH/$H_2O$ (80:20:0.7; v/v/v) mixture to obtain 1.73 g of the expected product.

NMR: 0.7–1.1:mt:6H; 2.2–3.7:mt:20H; 3.85:s:3H; 6.55:d:2H; 6.8:s:1H; 6.95:mt:2H; 7.3:mt:2H.

Preparation 3.23

1-(4-Carboxy-2-chlorophenyl)-5-(2,6-dimethoxyphenyl)-3-pyrazolecarboxylic acid ethyl ester.

(II'a: $R'_1$=4-$CO_2H$; $R_2$=2-Cl; $R_3$=H; $R_4$=$CH_3$).

3-Chloro-4-hydrazinobenzoic acid is described in U.S. Pat. No. 3,959,309. 5.6 g of this acid and 8.75 g of compound $A_1$ in 100 ml of AcOH are heated to reflux for 6 hours. The reaction mixture is poured into 500 ml of ice-cold water, and the precipitate formed is filtered off and then washed with water, pentane and then isopropyl ether. The product is dried under vacuum to obtain 2 g of the expected compound.

Preparation 3.24

5-(2,6-Dimethoxyphenyl)-1-(4-[N-methyl-N-(2-(N',N'-diethylamino)ethyl)carbamoyl]-2-chlorophenyl}-3-pyrazolecarboxylic acid ethyl ester.

(IIa: $R_1$=4-CONMe(CH$_2$)$_2$NEt$_2$; $R_2$=2-Cl; $R_3$=H; $R_4$=CH$_3$).

A solution of 2.63 g of the product of Preparation 3.23 in 30 ml of DCM and 4.5 ml of SOCl$_2$ is heated to reflux for 4 hours. After evaporation under vacuum followed by 2 azeotropic evaporations with 20 ml of DCM, the acid chloride formed is redissolved in 40 ml of DCM, and the mixture is then poured into a solution of 1.1 ml of N,N-diethyl-N'-methylethylenediamine and 1 ml of triethylamine in 4 ml of toluene and left stirring for 15 hours at RT. After evaporation under vacuum, extraction of the residue with 100 ml of DCM, 2 washes with water, drying over Na$_2$SO$_4$ and evaporation under vacuum, the residue is chromatographed on silica H, eluting with a DCM/MeOH (90:10; v/v) mixture and then DCM/MeOH/H$_2$O (90:10:0.5; v/v/v) to obtain 2.6 g of expected product.

NMR (DMSO+TFA): 2.8:s:3H; 3 to 3.7:u.c.:17H; 6.6:d:2H; 6.8:s:1H; 7.05:u.c.:2:H; 7.3:u.c. 2H.

Preparation 3.25

5-(2,6-Dimethoxyphenyl)-1-[4-(N-(2-morpholinoethyl)carbamoyl)-2-chlorophenyl]-3-pyrazolecarboxylic acid ethyl ester.

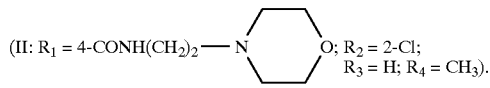

(II: $R_1$ = 4-CONH(CH$_2$)$_2$—N⟨O⟩; $R_2$ = 2-Cl; $R_3$ = H; $R_4$ = CH$_3$).

A solution of 2.63 g of the product of Preparation 3.23 in 4.5 ml of SOCl$_2$ and 30 ml of DCM is stirred under reflux for 4 hours. After evaporation under vacuum followed by 2 azeotropic evaporations with 30 ml of toluene, the acid chloride formed is redissolved in 40 ml of DCM, and the mixture is added to a solution of 0.9 ml of 4-(2-aminoethyl)morpholine and 1 ml of triethylamine in 4 ml of toluene. After stirring for 15 hours at RT, evaporation under vacuum, redissolution of the residue in 200 ml of DCM, washing with 100 ml of saturated NaCl solution, drying over Na$_2$SO$_4$ and evaporation under vacuum, 3 g of expected product are obtained.

NMR: 1.3:t:3H; 2.3–2.6:mt:6H; 3.3:mt:2H; 3.5:mt:10H; 4.3:qr:2H; 6.55:d:2H; 6.8:s: 1H; 7.1–7.4:mt:3H; 6.75:dd:1H; 6.9:dd:1H; 8.6:t:1H.

Preparation 3.26

5-(2,6-Dimethoxyphenyl)-1-(3-chloro-4-cyanophenyl)-3-pyrazolecarboxylic acid methyl ester.

(II'a: $R_1$=4-CN; $R_2$=3-Cl; $R_3$=H; $R_4$=CH$_3$).

A mixture containing 4.2 g of the compound obtained in Preparation 2.8 and 6 g of compound A in 10 ml of AcOH is heated on a water bath for 2 hours. It is poured into ice-cold water, and the precipitate formed is filtered off and then dried to obtain 3.78 g of the expected product.

Preparation 3.27

5-(2,6-Dimethoxyphenyl)-1-(4-carboxy-2-cyclopropylphenyl)-3-pyrazolecarboxylic acid methyl ester.

(II'a: $R'_1$=4-CO$_2$H; $R_2$=2-cyclopropyl; $R_3$=H; $R_4$=CH$_3$).

A mixture of 1.28 g of compound A and 1 g of the product of Preparation 2.9 in 12 ml of AcOH is stirred under reflux for 7 hours. Precipitation is induced with 120 ml of ice-cold water, and the precipitate is filtered off, washed with water and dried under vacuum over P$_2$O$_5$ to obtain 1.27 g of expected product.

NMR: 0.5:u.c.:2H; 0.8:u.c.:2H; 1.3:t:3H; 1.5:u.c.:1H; 3.6:s:6H; 4.3:qr:2H; 6.6:d:2H; 6.9:s:1H; 7.3:u.c.:3H; 7.7:d:1H; 13:bs:1H.

Preparation 3.28

5-(2,6-Dimethoxyphenyl)-1-{4-[N-methyl-N-(2-(N',N'-diethylamino)ethyl)carbamoyl]-2-cyclopropylphenyl}-3-pyrazolecarboxylic acid methyl ester.

(IIa: $R_1$=4-CON(Me)(CH$_2$)$_2$NEt$_2$; $R_2$=2-cyclopropyl; $R_3$=H; $R_4$=CH$_3$).

A solution of 1.27 g of the product of Preparation 3.27 in 28 ml of toluene and 2 ml of SOCl$_2$ is heated for 5 hours at 100° C. After evaporation under vacuum followed by 2 azeotropic evaporations with 30 ml of toluene, the acid chloride obtained is redissolved in 19 ml of DCM, and the mixture is poured slowly into a solution of 0.53 ml of N,N-diethyl-N'-methylethylenediamine and 0.61 ml of triethylamine in 1.9 ml of toluene. After stirring for 12 hours at RT, evaporation under vacuum, extraction with 100 ml of DCM, washing with water, drying over Na$_2$SO$_4$ and evaporation under vacuum, 1.29 g of the expected product are obtained.

NMR: 0.4–1:u.c.:10H; 1.2:t:3H; 1.4:mt:1H; 2.1–3:u.c.:9H; 3.5:u.c.:8H; 4.3:qr:2H; 6.5:d:2H; 6.6:s:1H; 6.8:s:1H; 6.9–7.2:mt:3H.

Preparation 3.29

5-(2,6-Dimethoxyphenyl)-1-(3-carboxy-4-chlorophenyl)-3-pyrazolecarboxylic acid methyl ester.

(II'a: $R'_1$=3-CO$_2$H; $R_2$=4-Cl; $R_3$=H; $R_4$=CH$_3$).

A mixture of 4 g of product of Preparation 2.10 and 4.6 g of compound A in 60 ml of AcOH is heated to reflux with stirring for 5 hours. It is poured into 100 ml of ice-cold water, and the precipitate is filtered off and washed with 5 ml of water and then 20 ml of ether. It is dried under vacuum to obtain 3 g of expected product, m.p.=206° C.

NMR: 3.55:s:6H; 3.85:s:3H; 6.7:d:2H; 6.9:s:1H; 7.35:dd:1H; 7.4:t:1H; 7.55:d:1H; 7.7:d:1H.

Preparation 3.30

5-(2,6-Dimethoxyphenyl)-1-(3-[N-methyl-N-(2-(N',N'-dimethylamino)ethyl)carbamoyl]-4-chlorophenyl)-3-pyrazolecarboxylic acid methyl ester.

(IIa: $R_1$=3-CON(Me)(CH$_2$)$_2$NMe$_2$; $R_2$=4-Cl; $R_3$=H; $R_4$=CH$_3$).

A solution of 1.5 g of the product of Preparation 3.29 in 20 ml of DCM and 2.6 ml of SOCl$_2$ is heated with stirring for three and a half hours at 60° C. After evaporation under vacuum, the acid chloride is redissolved in 10 ml of DCM, and the mixture is poured into a solution of 0.5 ml of N,N,N'-trimethylethylenediamine and 0.6 ml of triethylamine in 2.5 ml of toluene and then left stirring for 15 hours at RT. After evaporation under vacuum, dissolution of the residue in 100 ml of DCM, washing with 100 ml of water, drying over Na$_2$SO$_4$ and evaporation under vacuum, 0.8 g of expected product is obtained.

Preparation 3.31

5-(2,6-Dimethoxyphenyl)-1-(5-carboxy-2-methylphenyl)-3-pyrazolecarboxylic acid methyl ester.

(II'a: $R'_1$=5-CO$_2$H; $R_2$=2-CH$_3$; $R_3$=H; $R_4$=CH$_3$).

A mixture of 6.15 g of the product of Preparation 2.11 and 7.76 g of compound A in 100 ml of AcOH is heated to reflux with stirring for one and a half hours. After concentration under vacuum to 5 ml, precipitation with 20 ml of ice-cold water, filtration, washing of the precipitate with 5 ml of water and drying over $P_2O_5$ under vacuum at 80° C., 9.55 g of expected product are obtained, m.p.=189° C.

NMR: 1.20:t:3H; 3.55:s:6H; 4.26:qr:2H; 6.58:d:2H; 6.80:s:1H; 7.20:t:1H; 7.60:d:1H; 7.70:d:1H; 7.80:dd:1H.

Preparation 3.32

5-(2,6-Dimethoxyphenyl)-1-{5-[N-methyl-N-(3-(N',N'-dimethylamino)propyl)carbamoyl]-2-methylphenyl}-3-pyrazolecarboxylic acid methyl ester.

(IIa: $R_1$=5-CON(Me)(CH$_2$)$_3$NMe$_2$; $R_2$=2-CH$_3$; $R_3$=H; $R_4$=CH$_3$).

A solution of 2 g of the product of Preparation 3.31 in 10 ml of SOCl$_2$ is left stirring for 5 hours at RT. After evaporation under vacuum followed by 3 azeotropic distillations with 30 ml of DCM, the acid chloride formed is redissolved in 25 ml of DCM, and the mixture is poured into a solution of 0.81 ml of N,N,N'-trimethyl-1,3-propanediamine and 0.77 ml of triethylamine in 5 ml of DCM and left stirring for 2 hours at RT. After 2 washes with 20 ml of water and 2 extractions of the aqueous phases with 50 ml of DCM, the DCM phases are washed twice with 20 ml of 5% NaHCO$_3$ and then with 20 ml of water, then dried over MgSO$_4$ and evaporated under vacuum to obtain 2.3 g of expected product (oil).

NMR: 1.9:u.c.:2H; 2.1:s:3H; 2.6:s:3H; 2.8:s:6H; 2.9–3.2:u.c.:2H; 3.45:u.c.:2H; 3.6:s:6H; 3.8:s:3H; 6.6:d:2H; 6.85:s:1H; 7.05:bs:1H; 7.2–7.4:u.c.:3H.

By following the above procedures, the esters of formula IIa described in Table 3 below are prepared, either from an ester of formula II'a substituted with $R'_1$, or by the action of the appropriate hydrazine on compound A or compound $A_1$.

TABLE 3

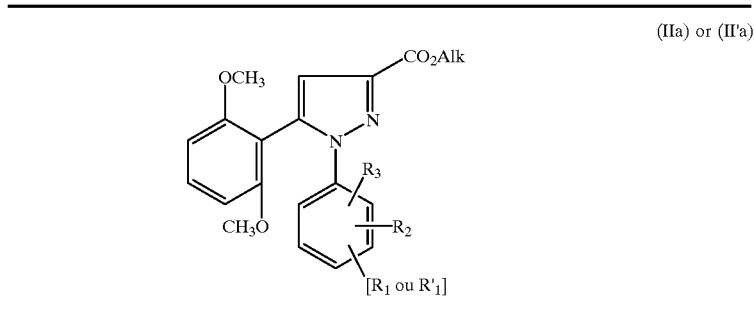

(IIa) or (II'a)

| Preparation (from) | [$R_1$ or $R'_1$] | $R_2$ | $R_3$ | Alk | M.p. ° C. or NMR (Salt) |
|---|---|---|---|---|---|
| 3.33 (3.21) | 4-CONMe(CH$_2$)$_2$NMe$_2$ | 2-OCH$_3$ | H | Me | NMR |
| 3.34 (3.21) | 4-CH—N⟨piperazine⟩NMe | 2-OCH$_3$ | H | Me | NMR |
| 3.35 (2.12) | 4-SO$_3$H | 2-CH$_3$ | 3-CH$_3$ | Me | 208 |
| 3.36 (3.35) | 4-SO$_2$NMe(CH$_2$)$_3$NMe$_2$ | 2-CH$_3$ | 3-CH$_3$ | Me | NMR |
| 3.37 (2.13) | 5-CO$_2$H | 2-Cl | H | Et | NMR |
| 3.38 (3.37) | 5-CONMe(CH$_2$)$_2$NMe$_2$ | 2-Cl | H | Et | NMR |
| 3.39 (2.16) | 4-CO$_2$H | 2-CF$_3$ | H | Et | 220 |
| 3.40 (3.39) | 4-CONMe(CH$_2$)$_2$NEt$_2$ | 2-CF$_3$ | H | Et | 70 (dec.) NMR |
| 3.41 (2.14) | 5-CO$_2$H | 2-OCH$_3$ | H | Et | NMR |
| 3.42 (3.41) | 5-CONMe(CH$_2$)$_2$NMe$_2$ | 2-OCH$_3$ | H | Et | NMR |
| 3.43 (3.1) | 4-CONH(CH$_2$)$_2$N(iPr)$_2$ | 2-iPr | H | Me | NMR |
| 3.44 (3.1 a) | 4-CO$_2$H | 2-iPr | H | Et | NMR |
| 3.45 (3.44) | 4-CONH(CH$_2$)$_3$N(nBu)$_2$ | 2-iPr | H | Et | NMR |
| 3.46 (3.44) | 4-CONH(CH$_2$)$_2$NEt$_2$ | 2-iPr | H | Et | NMR |

TABLE 3-continued

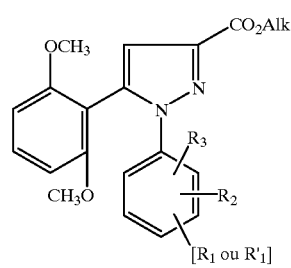

(IIa) or (II'a)

| Preparation (from) | [R₁ or R'₁] | R₂ | R₃ | Alk | M.p. °C. or NMR (Salt) |
|---|---|---|---|---|---|
| 3.47 (3.1) | 4-CONH-C(-CH₂-NMe₂)(cyclopentyl) | 2-iPr | H | Me | 100 |
| 3.48 (3.1) | 4-CON(CH₂CH₂NEt₂)₂ | 2-iPr | H | Me | 92 2HCl |
| 3.49 (3.1) | 4-CONHCH₂-(2-pyrrolidinyl-N-Et) | 2-iPr | H | Me | NMR |
| 3.50 (3.1) | 4-CONH-(2,2,6,6-tetramethylpiperidin-4-yl) | 2-iPr | H | Me | NMR |
| 3.51 (3.1) | 4-CO-N(pyrrolidin-3-yl-NEt₂) | 2-iPr | H | Me | NMR |
| 3.52 (3.1) | 4-CO-N(piperidin-4-yl-NMe₂) | 2-iPr | H | Me | NMR |
| 3.53 (3.1) | 4-CONMe(CH₂)₂CN | 2-iPr | H | Me | NMR |
| 3.54 (3.1) | 4-CONHCH₂CH=CH₂ | 2-iPr | H | Me | NMR |
| 3.55 (3.12) | 4-SO₂N(CH₂)NMe₂ \| Bz | 2-iPr | H | Me | NMR |
| 3.56 (2.19) | 4-NO₂ | 2-Me | H | Me | 162 |

NMR:

Preparation 3.33:2 to 3.8:mt:1H; 3.9:s:3H; 6.6:d:2H; 6.85:s:1H; 6.9 to 7.4:u.c.:4H.

Preparation 3.36 (DMSO+TFA): 1.9:u.c.+s:5H; 2.5:s:3H; 2.8:s:9H; 3–3.5:u.c.:2H; 3.25:t:2H; 3.6:s:6H; 3.85:s:3H; 6.6:d:2H; 6.9:s:1H; 7.05–7.15:u.c.:1H; 7.3:t:1H; 7.6:d:1H.

Preparation 3.37: 1.2:t:3H; 3.5:s:6H; 4.3:qr:2H; 6.5:d:2H; 6.8:s:1H; 7.2:t:1H; 7.6:d:1H; 7.7:s:1H; 7.85:d:1H.

Preparation 3.38: 1.4:t:3H; 1.8 to 3.3:u.c.:13H; 3.65:s:6H; 4.4:qr:2H; 6.6:d:2H; 6.95:s:1H; 7.2 to 7.6:u.c.:4H; 7.7:d:1H.

Preparation 3.40: 0.6 to 1:u.c. 6H; 1.3:t:3H; 2.2:u.c.:2H; 2.4 to 3.4:u.c.:7H; 3.6:s:6H; 4.1:u.c.:2H; 4.3:qd:2H; 6.6:d:2H; 6.8:s:1H; 7.15:u.c.:2H; 7.6:d:1H; 7.8:bs:1H.

Preparation 3.41: 1.4:t:3H; 3.6:s:9H; 4.4:qr:2H; 6.62:d:2H; 6.81:s:1H; 7.2:d:1H; 7.36:t:1H; 7.8:d:1H; 8.0:dd:1H; 12.6:bs:1H.

Preparation 3.42: 1.4:t:3H; 1.8 to 2.4:bs:8H; 2.8:bs:3H; 3.2 to 3.8:bs:2H; 3.6:s:9H; 4.4:qd:2H; 6.6:d:2H; 6.8:s:1H; 7.0 to 7.5:u.c. 4H.

Preparation 3.43: 1.0–1.1:u.c.:18H; 2.4–2.75:2mt:3H; 2.9–3.1:mt:2H; 3.1–3.35:mt:2H; 3.65:s:6H; 3.9:s:3H; 6.65:d:2H; 6.9:s: 1H; 7.3–7.4:mt:2H; 7.7:d:1H; 7.8:s:1H; 8.55:t:1H.

Preparation 3.45: 0.75:t:6H; 0.9:d:6H; 1.05–1.15:u.c.:8H; 1.5:t:2H; 2.5–2.4:u.c.:6H; 2.55:sp:1H; 3.15:mt:2H; 3.55:s:6H; 4.2:s:3H; 6.5:d:2H; 6.72:s:1H; 7.1–7.25:u.c.:2H; 7.55:dd:1H; 7.65:d:1H; 8.45:t:1H.

Preparation 3.46: 0.8–1.1:u.c.:12H; 1.25:t:3H; 2.4–2.8:u.c.:6H; 3.1–3.4:u.c.:3H; 3.5:s:6H; 4.2:qt:2H; 6.5:d:2H; 7.2:u.c.:2H; 7.6:d:1H; 7.8:bs:1H; 8.6:bs:1H.

Preparation 3.49: 0.9–1.15:2mt:9H; 1.5–1.9:u.c.:4H; 2.1–2.45:2mt:2H; 2.65:mt:1H; 2.75–3:mt:1H; 3–3.2:u.c.:2H; 3.2–3.55:u.c.:2H; 3.65:s:6H; 3.9:s:3H; 6.65:d:2H; 6.9:s:1H; 7.25–7.4:mt:2H; 7.7:d:1H; 7.85:s:1H; 8.6:t:1H.

Preparation 3.50:1.05:d:6H; 1.1–1.6:2s+m:14H; 1.8:dd:2H; 2.65:mt:1H; 3.7:s:6H; 3.9:s:3H; 4.2–4.5:u.c.:1H; 6.65:d:2H; 6.9:s:1H; 7.25–7.4:mt:2H; 7.7:d:1H; 7.85:s:1H; 8.3:d:1H.

Preparation 3.51 (DMSO+TFA): 1.0:d:6H; 1.1–1.4:u.c.:6H; 2.0–2.5:u.c.:2H; 2.7:2:u.c.:1H; 3.0–4.2:3u.c.+s:18H; 6.7:d:2H; 6.9:s:1H; 7.3–7.55:u.c.:4H.

Preparation 3.52 (DMSO+TFA): 0.95:d:6H; 1.5–1.8:u.c.:2H; 1.8–2.2:u.c.:2H; 2.6:mt: 1H; 2.75:s:6H; 2.9–3.8:2u.c.+s:10H; 3.85:s:3H; 4.5–4.7:u.c.:1H; 6.6:d:2H; 6.85:s:1H; 7.2–7.35:mt:4H.

Preparation 3.53 (DMSO+TFA): 0.98:d:6H; 2.6:mt:1H; 2.7–3.8:u.c.:13H; 3.82:s:3H; 6.58:d:2H; 6.85:s:1H; 7.15–7.37:u.c.:4H.

Preparation 3.54:1.05:d:6H; 2.7:mt:1H; 3.7:s:6H; 3.85–4.0:s+mt:5H; 5.1–5.3:u.c.:2H; 5.8–6.1:u.c.:1H; 6.55:d:2H; 6.9:s:1H; 7.3–7.4:u.c. 2H; 7.75:s:1H; 7.9:s:1H; 8.8:t:1H.

Preparation 3.55: 1.05:d:6H; 2:s:6H; 2.15:t:2H; 2.75:qt:1H; 3.2:t:2H; 3.7:s:6H; 3.9:s:3H; 4.45:s:2H; 6.7:d:2H; 7:s:1H; 7.3–7.5:u.c.:6H; 7.55:d:1H; 7.7–7.9:u.c.:2H.

Preparation 3.57

5-(2,6-Dimethoxyphenyl)-1-[4-[N-methyl-N-[3-[N'-methyl-N'-(tert-butoxycarbonyl)amino]propyl]carbamoyl]-2-isopropylphenyl]-3-pyrazolecarboxylic acid methyl ester.

(IIa: $R_1$=4-CONMe(CH$_2$)$_3$N(Me)COOt-Bu; $R_2$=2-iPr; $R_3$=H; $R_4$=CH$_3$).

A) N-Methyl-N-(3-methylaminopropyl)carbamic acid tert-butyl ester.

A solution of 4.19 g of N,N'-dimethyl-1,3-propanediamine in 80 ml of THF is cooled to 0° C., a solution of 2.68 g of di-tert-butyl dicarbonate in 25 ml of THF is added and the mixture is left stirring for 72 hours at RT. Some insoluble matter is filtered off and the filtrate is concentrated under vacuum. The residue is extracted with DCM, the organic phase is washed three times with water and dried over MgSO$_4$ and the solvent is evaporated off under vacuum. 1.6 g of the expected product are obtained in the form of a yellow oil.

B) 5-(2,6-Dimethoxyphenyl)-1-[4-[N-methyl-N-[3-[N'-methyl-N'-(tert-butoxycarbonyl)amino]propyl]carbamoyl]-2-isopropylphenyl]-3-pyrazolecarboxylic acid methyl ester.

A solution of 2.6 g of the compound obtained in step A of Preparation 3.2 is added at RT and under a nitrogen atmosphere to a solution of 1.31 g of the compound obtained in the preceding step and 0.9 ml of triethylamine in 4 ml of DCM, and the reaction mixture is left stirring overnight at RT. It is washed twice with water, the organic phase is dried over MgSO$_4$ and the solvent is evaporated off under vacuum. The residue is chromatographed on silica, eluting with a toluene/AcOEt mixture from (65:35; v/v) to (60:40; v/v). 2.85 g of the expected product are obtained.

NMR (DMSO+TFA): 1.0:d:6H; 1.4:d:9H; 1.6–1.9:u.c.:2H; 2.7:mt:1H; 2.7–3.55:d+bs+u.c.:10H; 3.65:s:6H; 3.9:s:3H; 6.65:d:2H; 6.9:s:1H; 7.3–7.45:u.c.:4H.

Preparation 3.58

5-(2,6-Dimethoxyphenyl)-1-[4-(4-methylphenylsulphonylamino)-2-isopropylphenyl]-3-pyrazolecarboxylic acid ethyl ester.

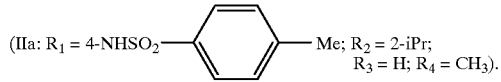

(IIa: $R_1$ = 4-NHSO$_2$—⟨ ⟩—Me; $R_2$ = 2-iPr; $R_3$ = H; $R_4$ = CH$_3$).

A mixture of 3.44 g of the compound obtained in Preparation 2.18 and 2.6 g of compound A$_1$ in 50 ml of acetic acid is heated for 1 hour at 70° C. The reaction mixture is poured into water, the resulting mixture is extracted with AcOEt, the organic phase is dried over Na$_2$SO$_4$ and the solvent is evaporated off under vacuum. The residue is chromatographed on silica H, eluting with a DCM/MeOH (100:0.5; v/v) mixture. 1.26 g of the expected product are obtained.

NMR: 0.7:d:6H; 1.22:t:3H; 2.2–2.5:u.c.:4H; 3.45:s:6H; 4.2:t:2H; 6.46:d:2H; 6.69:s:1H; 6.75–6.9:u.c.:2H; 7.0:d:1H; 7.15–7.3:u.c.:3H; 7.5:d:2H; 10.2:s:1H.

Preparation 3.59

5-(2,6-Dimethoxyphenyl)-1-[4-[4-methylphenylsulphonyl-N-(3-diethylaminopropyl)amino]-2-isopropylphenyl]-3-pyrazolecarboxylic acid ethyl ester.

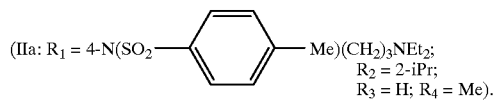

(IIa: $R_1$ = 4-N(SO$_2$—⟨ ⟩—Me)(CH$_2$)$_3$NEt$_2$; $R_2$ = 2-iPr; $R_3$ = H; $R_4$ = Me).

A mixture of 0.65 g of the compound obtained in Preparation 3.58, 0.338 g of (3-chloropropyl)diethylamine and 0.65 g of K$_2$CO$_3$ in 5 ml of DMF is heated at 80° C. for 2 hours. The reaction mixture is poured into water, the resulting mixture is extracted with AcOEt, the organic phase is dried over Na$_2$SO$_4$ and the solvent is evaporated off under vacuum. The residue is chromatographed on silica H, eluting with a DCM/MeOH (100:5; v/v) mixture. 0.57 g of the expected product is obtained.

NMR: 0.8:bs:6H; 0.95:t:6H; 1.4:t:3H; 1.5:qt:2H; 2.3–2.65:u.c.:10H; 3.5–3.8:u.c.:8H; 4.35:qr:2H; 6.7:d:2H; 6.75:d:1H; 6.9:s:1H; 7.05:dd:1H; 7.2–7.6:u.c.:6H.

Preparation 3.60

5-[2-(Cyclopropylmethyloxy)-6-methoxyphenyl]-1-(4-carboxy-2-isopropylphenyl)-3-pyrazolecarboxylic acid ethyl ester.

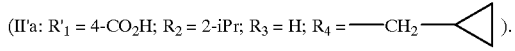
(II'a: R'$_1$ = 4-CO$_2$H; R$_2$ = 2-iPr; R$_3$ = H; R$_4$ = —CH$_2$—◁ ).

A mixture of 5.26 g of the compound obtained in Preparation 1.2 and 3.9 g of the compound obtained in Preparation 2.1 in 50 ml of acetic acid is heated at 80° C. for 8 hours. The reaction mixture is poured into a water/ice mixture, and the precipitate formed is drained and washed with water and then with pentane. The precipitate is taken up with toluene and the solvent is evaporated off under vacuum. 5.2 g of the expected product are obtained.

Preparation 3.61

5-[2-(Cyclopropylmethyloxy)-6-methoxyphenyl]-1-[4-[N-methyl-N-(3-dimethylaminopropyl)carbamoyl]-2-isopropylphenyl]-3-pyrazolecarboxylic acid ethyl ester.

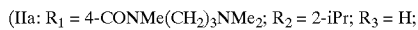
(IIa: R$_1$ = 4-CONMe(CH$_2$)$_3$NMe$_2$; R$_2$ = 2-iPr; R$_3$ = H;

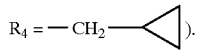
R$_4$ = —CH$_2$—◁ ).

This compound is prepared according to the procedures described in steps A and B of Preparation 3.2, from 5.2 g of the compound obtained in Preparation 3.60 and 2.4 ml of SOCl$_2$, followed by 1.39 g of N,N,N'-trimethyl-1,3-propanediamine and 1.5 ml of triethylamine in 10 ml of toluene. The product is purified by chromatography on silica, eluting with DCM and then with a DCM/MeOH (88:2; v/v) mixture. 3.8 g of the expected product are obtained.

Preparation 3.62

5-(2,6-Dimethoxyphenyl)-1-[4-(4-methylphenylsulphonylamino)-2-isobutylphenyl]-3-pyrazolecarboxylic acid methyl ester.

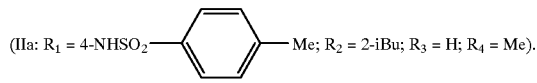
(IIa: R$_1$ = 4-NHSO$_2$—⬡—Me; R$_2$ = 2-iBu; R$_3$ = H; R$_4$ = Me).

A mixture of 1.9 g of the compound obtained in Preparation 2.20 and 1.6 g of the compound A in 30 ml of acetic acid is heated to reflux for 45 minutes. After cooling to RT, the reaction mixture is poured into water, and the precipitate formed is drained and dried. 1 g of the expected product are obtained after recrystallization in 2-propanol, m.p.=224° C.

NMR: 0.55:d:6H; 1.5:mt:1H; 1.9:d:2H; 2.3:s:3H; 3.45:s:6H; 3.8:s:3H; 6.5:d:2H; 6.75:s:1H; 6.8:d:1H; 6.9:dd:1H; 7.05:d:1H; 7.15–7.7:u.c.:5H; 10.25:s:1H.

Preparation 3.63

5-(2,6-Dimethoxyphenyl)-1-[4-(4-methylphenylsulphonylamino)-2-cyclopentylphenyl]-3-pyrazolecarboxylic acid methyl ester.

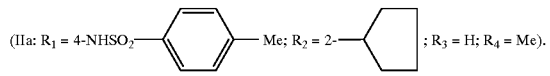
(IIa: R$_1$ = 4-NHSO$_2$—⬡—Me; R$_2$ = 2-—⬠ ; R$_3$ = H; R$_4$ = Me).

A mixture of 2.42 g of the compound obtained in Preparation 2.21 and 2.92 g of compound A in 50 ml of acetic acid is heated for 1 hour at 80° C. The reaction mixture is poured into water, the resulting mixture is extracted with AcOEt, the organic phase is dried over Na$_2$SO$_4$ and the solvent is evaporated off under vacuum. The residue is chromatographed on silica H, eluting with a DCM/MeOH (100:1; v/v) mixture. 0.95 g of the expected product are obtained after trituration in ether, m.p.=200–230° C.

NMR: 1.0–1.8:u.c.:8H; 2.37:s:3H; 3.1–3.7:u.c.:7H; 3.82:s:3H; 6.55:d:2H; 6.79:s:1H; 6.85–7.0:u.c.:2H; 7.05:d:1H; 7.21–7.42:u.c.:3H; 7.58:d:2H; 10.3:s:1H.

Preparation 3.64

5-(2,6-Dimethoxyphenyl)-1-(4-carboxy-3-isopropylphenyl)-3-pyrazolecarboxylic acid ethyl ester.

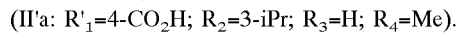
(II'a: R'$_1$=4-CO$_2$H; R$_2$=3-iPr; R$_3$=H; R$_4$=Me).

A mixture of 0.36 g of the compound obtained in Preparation 2.22 and 0.48 g of compound A$_1$ in 10 ml of acetic acid is heated to reflux for 5 hours. The reaction mixture is poured into 160 ml of ice-cold water, and the precipitate formed is drained, washed with water and dried. 0.52 g of the expected product is obtained, m.p.=180° C. (dec.).

Preparation 3.65

1-[4-[N-(2-Diethylaminoethyl)carbamoyl]-3-isopropylphenyl]-5-(2,6-dimethoxyphenyl)-3-pyrazolecarboxylic acid ethyl ester.

(IIa: R$_1$=4-CONH(CH$_2$)$_2$NEt$_2$; R$_2$=3-iPr; R$_3$=H; R$_4$=Me).

This compound is prepared according to the procedure described in steps A and B of Preparation 3.2, from 0.5 g of the compound obtained in Preparation 3.64 and 5 ml of SOCl$_2$ in 20 ml of chloroform, followed by 0.2 ml of N,N-diethylethylenediamine and 0.8 ml of triethylamine in 20 ml of chloroform. 0.37 g of the expected product is obtained after crystallization in AcOEt, m.p.=130° C. (dec.).

Preparation 3.66

5-(2,6-Dimethoxyphenyl)-1-(4-nitro-5,6,7,8-tetra-hydro-1-naphthyl)-3-pyrazolecarboxylic acid methyl ester.

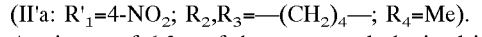
(II'a: R'$_1$=4-NO$_2$; R$_2$,R$_3$=—(CH$_2$)$_4$—; R$_4$=Me).

A mixture of 6.3 g of the compound obtained in Preparation 2.23 and 7.45 g of compound A in 150 ml of acetic acid is heated to reflux for 2 hours. After cooling to RT, 100 ml of water and 30 ml of MeOH are added and the crystallized product is drained. 4.6 g of the expected product are obtained, m.p.=212° C.

NMR: 1.7:mt:4H; 2.55:mt:2H; 2.82:mt:2H; 3.65:s:6H; 3.85:s:3H; 6.65:d:2H; 6.9:s:1H; 7.02:d:1H; 7.33:t:1H; 7.67:d:1H.

Preparation 3.67

5-(2,6-Dimethoxyphenyl)-1-(5-(3-(diethylamino)propanoylamino)-2-isopropylphenyl)-3-pyrazolecarboxylic acid methyl ester.

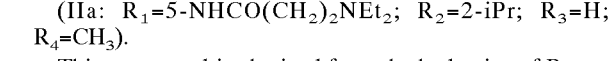
(IIa: R$_1$=5-NHCO(CH$_2$)$_2$NEt$_2$; R$_2$=2-iPr; R$_3$=H; R$_4$=CH$_3$).

This compound is obtained from the hydrazine of Preparation 2.24.

NMR (DMSO+TFA): 0.65–1.35:u.c.:12H; 2.5:qt:1H; 2.8:t:2H; 3.15:qr:4H; 3.36:t:2H; 3.57:s:6H; 3.8:s:3H; 6.5:d:2H; 6.78:s:1H; 7.1–7.4:u.c.:3H; 7.8:d:1H.

PREPARATIONS OF THE ACIDS II, II'

Preparation 4.1

1-[4-[N-Methyl-N-(3-(N',N'-dimethylamino)propyl)carbamoyl]-2-isopropylphenyl]-5-(2,6-dimethoxyphenyl)-3-pyrazolecarboxylic acid.

(II, $R_1$=4-CONMe(CH$_2$)$_3$NMe$_2$; $R_2$=2-iPr; $R_3$=H; $R_4$=CH$_3$).

23 g of the compound obtained in Preparation 3.2 in 230 ml of dioxane and 6.2 g of potassium hydroxide in 6 ml of water are mixed. The mixture is heated to reflux for three and a half hours. After cooling, it is evaporated, the residue is redissolved in the minimum amount of water and the mixture is washed three times with ether and then acidified to pH 4 by adding concentrated HCl; the aqueous phase is evaporated, the residue is then redissolved in the minimum amount of EtOH and the KCl is filtered off (twice). After evaporation, 23.93 g of the expected product are obtained in the form of a light yellow foam, m.p.=128° C. (dec.).

NMR: 0.95:d:6H; 1.95:mt:2H; 2.45–3.3:u.c.:12H; 3.35–3.8:u.c.:8H; 6.6:d:2H; 6.8:s:1H; 7–7.5:u.c.:4H.

Preparation 4.1a

1-[4-[N-Methyl-N-(3-(N',N'-dimethylamino)propyl)carbamoyl]-2-isopropylphenyl]-5-(2,6-dimethoxyphenyl)-3-pyrazolecarboxylic acid potassium salt.

A solution of 8.07 g of KOH in 133 ml of water is added to a solution of 26.6 g of the product of Preparation 3.2a in 133 ml of ethanol. The solution is stirred for 8 hours, then left stirring for 15 hours and evaporated under vacuum to obtain the expected potassium salt.

Preparation 4.2

1-[4-[N-(2-Cyanoethyl)carbamoyl]-2-isopropylphenyl]-5-(2,6-dimethoxyphenyl)-3-pyrazolecarboxylic acid.

(II: $R_1$=4-CONHCH$_2$CH$_2$CN; $R_2$=2-iPr; $R_3$=H; $R_4$=CH$_3$).

A solution of 0.9 g of KOH in 3 ml of water is added to a solution of 3.04 g of the compound obtained in Preparation 3.3 in 30 ml of 1,4-dioxane and a few drops of MeOH, and the mixture is left stirring overnight at RT. It is concentrated under vacuum, the residue is taken up with water, the aqueous phase is washed with ether, acidified to pH 2 by adding 10% HCl and extracted with DCM, the organic phase is dried over Na$_2$SO$_4$ and the solvent is evaporated off under vacuum. 2.93 g of the expected product are obtained, m.p.=128° C. (dec.).

NMR: 1:d:6H; 2.65:mt:1H; 2.8:t:2H; 3.5:t:2H; 3.6:s:6H; 6.6:d:2H; 6.8:s:1H; 7.2–7.4:u.c.:2H; 7.7:dd:1H; 7.8:d:1H.

From the esters of formula (IIa) described in Table 2, and by working according to the procedure described in Preparation 4.1 or Preparation 4.2, the acids of formula (II) described in Table 4 below are obtained.

TABLE 4

(II)

[Structure: pyrazole core with CO$_2$H at 3-position, N-1 linked to phenyl bearing iPr and $R_1$ (para), and C-5 linked to 2,6-dimethoxyphenyl (OCH$_3$ groups shown)]

| Preparation | $R_1$ | M.p. ° C. or NMR |
|---|---|---|
| 4.3 | —CONH(CH$_2$)$_3$NMe$_2$ | 188 NMR |
| 4.4 | —CONH(CH$_2$)$_2$NMe$_2$ | 178–180 (dec.) NMR |
| 4.5 | —CONH(CH$_2$)$_3$NEt$_2$ | NMR |
| 4.6 | —CONH(CH$_2$)$_2$N(pyrrolidinyl) | NMR |
| 4.7 | —CONH-(2-pyridyl) | NMR |
| 4.8 | —CONH—CH$_2$—C(Me)$_2$—CH$_2$NMe$_2$ | 135 (dec.) NMR |
| 4.9 | —CONH-(4-(N-benzyl)piperidinyl) (N—CH$_2$C$_6$H$_5$) | NMR |
| 4.10 | —CONH-(quinuclidinyl) | 266 (dec.) |

Preparation 4.3
NMR: 0.9:d:6H; 1.6:mt:2H; 2.15:s:6H; 2.35:t:2H; 2.6:mt:1H; 3.2:u.c.:2H; 3.55:s:6H; 6.5:d:2H; 6.6:s:1H; 7.1–7.2:u.c.:2H; 7.7:dd:1H; 7.9:bs:1H; 8.6:t:1H.

Preparation 4.4
NMR (DMSO+TFA): 1:d:6H; 2.65:mt:1H; 2.85:s:6H; 3.3:mt:2H; 3.6:mt+s:8H; 6.6:d:2H; 6.8:s:1H; 7.25–7.4:u.c.:2H; 7.7:dd:1H; 7.85:bs:1H.

Preparation 4.5
NMR: 0.95:d:6H; 1.15:t:6H; 1.8–2:u.c.:2H; 2.6:mt:1H; 3.1:mt:4H; 3.3:t:2H; 3.6:u.c.+s:8H; 6.5:d:2H; 6.75:s:1H; 7.2:t:2H; 7.6:dd:1H; 7.75:d:1H.

Preparation 4.6
NMR (DMSO+TFA): 1:d:6H; 1.8–2.2:u.c.:4H; 2.65:mt:1H; 3:mt:2H; 3.3:mt:2H; 3.6:bs:10H; 6.6:d:2H; 6.8:s:1H; 7.2–7.4:u.c.:2H; 7.6–7.9:u.c.:2H; 8.9:t:1H.

Preparation 4.7
1.1:d:6H; 2.7:mt:1H; 3.7:s:6H; 6.65:d:2H; 6.9:s:1H; 7.2–7.4:u.c.:3H; 7.8–8.5:m:5H.

Preparation 4.8

NMR: 1–1.2:m:12H; 2.6–2.9:u.c.:9H; 3.3:d:2H; 3.7:s:6H; 6.6:d:2H; 6.8:s:1H; 7.3–7.4:u.c.:2H; 7.7–7.9:u.c.:2H; 8.8:t:1H.

Preparation 4.9

NMR (DMSO+TFA): 1:d:6H; 1.8:mt:2H; 2.1:mt:2H; 2.7:mt:1H; 3–3.5:u.c.:4H; 3.6:s:6H; 4:mt 1H; 4.3:s:2H; 6.6:d:2H; 6.8:s:1H; 7.2–7.4:u.c.:2H; 7.4–7.6:u.c.:5H; 7.7:d:1H; 7.8:s:1H.

Preparation 4.11

5-(2,6-Dimethoxyphenyl)-1-[2-isopropyl-4-(N-methyl-N-(3-(N',N'-dimethylamino)propyl)aminosulphonyl)phenyl]-3-pyrazolecarboxylic acid.

(II: $R_1$=4-$SO_2$NMe$(CH_2)_3$NMe$_2$; $R_2$=2-iPr; $R_3$=H; $R_4$=$CH_3$).

A mixture containing 1.1 g of the ester obtained in Preparation 3.13 and 280 mg of potassium hydroxide in 10 ml of water is left stirring for 6 hours at RT. The reaction medium is concentrated under vacuum until 5 ml are obtained, and the residue is then stirred in the presence of 100 ml of ether and 3 ml of water. The aqueous phase is neutralized to pH 6 by adding 1N HCl; it is filtered, and the residue is then dried over $P_2O_5$ to obtain 860 mg of the expected product.

NMR: 0.85:d:6H; 1.5:mt:2H; 2.15:s:6H; 2.3:t:2H; 2.6:s+mt:4H; 2.9:t:2H; 3.5:s:6H; 6.5:d:2H; 6.7:s:1H; 7.2:t:1H; 7.4:d:1H; 7.5–7.6:u.c.:2H.

Preparation 4.12

5-(2,6-Dimethoxyphenyl)-1-[4-[N-[3-(N',N'-dimethylamino)propyl]carbamoyl]-5,6,7,8-tetrahydro-1-naphthyl]-3-pyrazolecarboxylic acid.

(II: $R_1$=4-CONH$(CH_2)_3$NMe$_2$; $R_2$, $R_3$=—$(CH_2)_4$—; $R_4$=$CH_3$).

A mixture of 0.98 g of the compound obtained in Preparation 3.15 and 0.16 g of LiOH in 5 ml of methanol and 1 ml of water is heated for 3 hours at 40° C. It is evaporated under vacuum, and the residue is neutralized to pH 6 with 1N HCl and then extracted with DCM. The organic phase is dried over MgSO$_4$ and evaporated under vacuum to obtain 0.47 g of expected product.

NMR: 1.5–2.1:u.c.:6H; 2.3–4:u.c.:20H; 6.5–7.6:u.c.:6H; 8.4:t:1H.

Preparation 4.13

5-(2,6-Dimethoxyphenyl)-1-f4-[N-methyl-N-(2-(N',N'-dimethylamino)ethyl)aminosulphonyl]-5,6,7,8-tetrahydro-1-naphthyl)-3-pyrazolecarboxylic acid potassium salt.

(II: $R_1$=4-$SO_2$NMe$(CH_2)_2$NMe$_2$; $R_2$, $R_3$=—$(CH_2)_4$—; $R_4$=Me).

A solution of 0.87 g of ester obtained in Preparation 3.17 in 5 ml of dioxane is left stirring for 8 hours at RT with 320 mg of KOH in 0.5 ml of water. The mixture is evaporated under vacuum and the residue is extracted with a mixture of 10 ml of water, 5 ml of ethanol and 100 ml of ether. After decantation, the gum obtained is triturated three times in ether; the product crystallizes. It is filtered off to obtain 0.9 g of the expected salt.

Preparation 4.14

5-(2,6-Dimethoxyphenyl)-1-(4-carbamoyl-2-methylphenyl)-3-pyrazolecarboxylic acid.

(II: $R_1$=4-CONH$_2$; $R_2$=2-$CH_3$; $R_3$=H; $R_4$=$CH_3$).

A solution containing 0.4 g of the compound obtained in Preparation 3.18 in 5 ml of dioxane and 220 mg of KOH in 1 ml of water is left stirring at RT for 2 hours. It is acidified to pH 1 by adding concentrated HCl and then concentrated under vacuum. 5 ml of water are added, the gum formed is then stirred with 50 ml of DCM and the precipitate formed is filtered off. 330 mg of the expected product are obtained, m.p.=275–276° C.

NMR: 2.05:s:3H; 3.55:s:6H; 6.55:d:2H; 6.7:s:1H; 7:d:1H; 7.2:t:1H; 7.4:bs:1H; 7.55:d:1H; 7.7:s:1H; 7.9:bs:1H.

Preparation 4.15

5-(2,6-Dimethoxyphenyl)-1-{2,3-dimethyl-4-[N-(2-(N',N'-dimethylamino)ethyl)carbamoyl]phenyl}-3-pyrazolecarboxylic acid.

(II: $R_1$=4-CONH$(CH_2)_2$NMe$_2$; $R_2$=2-$CH_3$; $R_3$=3-$CH_3$; $R_4$=$CH_3$).

A solution of 1.8 g of the product of Preparation 3.20 and 0.32 g of LiOH in 10 ml of MeOH and 2 ml of water is left stirring for 2 hours at 40° C. The pH is adjusted to 6 with 1N HCl and the mixture is evaporated under vacuum. After extraction of the residue with 50 ml of DCM and evaporation, 1.3 g of expected product are obtained.

NMR: 1.9:s:3H; 2.2:s+s:9H; 2.5:t:2H; 3.4:qd:2H; 3.7:s:6H; 6.6–6.7:u.c.:3H; 6.9–7.1:u.c.:2H; 7.3:t:1H; 8.3:t:1H.

Preparation 4.16

5-( 2,6-Dimethoxyphenyl)-1-{4-[N-methyl-N-(2-(N',N'-diethylamino)ethyl)carbamoyl]-2-methoxyphenyl}-3-pyrazolecarboxylic acid.

(II: $R_1$=4-CONMe$(CH_2)_2$NEt$_2$; $R_2$=2-OCH$_3$; $R_3$=H; $R_4$=$CH_3$).

A mixture of 1.73 g of the product of Preparation 3.22 and 0.3 g of LiOH in 400 ml of MeOH and 6 ml of water is left stirring under reflux for 6 hours, and then acidified to pH 2 with concentrated HCl. After evaporation under vacuum and stirring of the residual oil for 30 minutes at RT with 400 ml of chloroform, and after settling has taken place, separation and drying of the organic phase over Na$_2$SO$_4$ and evaporation, 1.2 g of expected product are obtained.

NMR: 1.05–1.4:mt:6H; 3:bs:3H; 3.1–3.9:mt:13H; 6.6:d:2H; 6.8:s:1H; 7–7.4:mt:4H.

Preparation 4.17

5-(2,6-Dimethoxyphenyl)-1-(4-[N-methyl-N-(2-(N',N'-diethylamino)ethyl)carbamoyl]-2-chlorophenyl)-3-pyrazolecarboxylic acid.

(II: $R_1$=4-CONMe$(CH_2)_2$NEt$_2$; $R_2$=2-Cl; $R_3$=H; $R_4$=$CH_3$).

A mixture of 2.6 g of the product of Preparation 3.24 dissolved in 100 ml of ethanol and 0.53 g of KOH in 15 ml of water is left stirring for 3 days at RT. After acidification to pH 3 with concentrated HCl, evaporation under vacuum, trituration of the residue in 10 ml of water, filtration and drying under vacuum over $P_2O_5$, 1.55 g of expected product are obtained.

Preparation 4.18

5-(2,6-Dimethoxyphenyl)-1-[4-(N-(2-morpholinoethyl)carbamoyl)-2-chlorophenyl]-3-pyrazolecarboxylic acid.

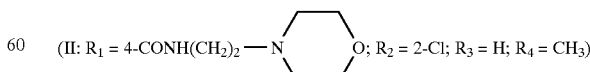

(II: $R_1$ = 4-CONH$(CH_2)_2$—N◯O; $R_2$ = 2-Cl; $R_3$ = H; $R_4$ = $CH_3$)

A solution of 1.5 g of the product of Preparation 3.25 in 75 ml of ethanol is heated with stirring for 1 hour at 60° C. with a solution of 0.38 g of KOH in 10 ml of water. After acidification to pH 4.5 with concentrated HCl and evaporation under vacuum, 4 g of mixture of the expected product and KCl are obtained.

NMR (DMSO+TFA): 2.9–4:mt:H; 6.5:d:2H; 6.8:s:1H; 7.1–7.4:mt:2H; 7.8:dd:1H; 8:d:1H; 9.1:bs:1H.

Preparation 4.19

5-(2,6-Dimethoxyphenyl)-1-(3-chloro-4-cyanophenyl)-3-pyrazolecarboxylic acid.

(II': $R_1$=4-CN; $R_2$=3-Cl; $R_3$=H; $R_4$=$CH_3$).

A mixture containing 0.5 g of the compound obtained in Preparation 3.26 and 60 mg of LiOH in 5 ml of aqueous methanol is heated on a water bath for 3 hours. After cooling, the pH is lowered to 5 by adding 1N HCl. The precipitate formed is filtered off and dried to obtain 0.36 g of the expected compound.

Preparation 4.20

5-(2,6-Dimethoxyphenyl)-1-(4-carbamoyl-3-chlorophenyl)-3-pyrazolecarboxylic acid.

(II: $R_1$=4-$CONH_2$; $R_2$=3-Cl; $R_3$=H; $R_4$=$CH_3$).

A mixture containing 0.87 g of the compound obtained in Preparation 4.19, 390 mg of $K_2CO_3$ and 0.4 ml of 30% hydrogen peroxide in 5 ml of DMSO is left stirring at RT for 24 hours. It is acidified to pH 3 by adding 1N HCl, water is then added, and the precipitate formed is filtered off and dried to obtain 0.73 g of the expected product.

Preparation 4.21

5-(2,6-Dimethoxyphenyl)-1-{4-[N-methyl-N-(2-(N',N'-diethylamino)ethyl)carbamoyl]-2-cyclopropylphenyl)-3-pyrazolecarboxylic acid.

(II: $R_1$=4-CONMe$(CH_2)_2$NEt$_2$; $R_2$=2-cyclopropyl; $R_3$=H; $R_4$=$CH_3$).

A solution of 1.29 g of the product of Preparation 3.28 in 26 ml of ethanol is left stirring for 22 hours at RT with a solution of 0.33 g of KOH in 4 ml of water. After acidification to pH 3 with concentrated HCl, evaporation and azeotropic distillation with 100 ml of toluene and then with 100 ml of pentane, the residue is triturated in pentane, filtered off and dried to obtain 1.4 g of mixture of the expected product with KCl.

NMR: 0.4–1.2:mt:14H; 1.5:u.c.:1H; 2.1–3.8:mt:13H; 6.5:d:2H; 6.7:bs:2H; 7:s:2H; 7.2:t:1H.

Preparation 4.22

5-(2,6-Dimethoxyphenyl)-1-}3-[N-methyl-N-(2-(N',N'-dimethylamino)ethyl)carbamoyl]-4-chlorophenyl)-3-pyrazolecarboxylic acid.

(II: $R_1$=3-CONMe$(CH_2)_2$NMe$_2$; $R_2$=4-Cl; $R_3$=H; $R_4$=$CH_3$).

A solution of 0.8 g of the product of Preparation 3.30 in 10 ml of dioxane is left stirring for 6 hours at RT with 0.22 g of KOH in 2 ml of $H_2O$. After evaporation under vacuum, the residue is dissolved in 5 ml of water, and the mixture is neutralized to pH 5 with concentrated HCl and then saturated with NaCl. It is extracted twice with 100 ml of DCM, and the organic phase is dried over $Na_2SO_4$ and evaporated under vacuum to obtain 0.43 g of expected product.

NMR: 1.9–3.15:u.c.:13H; 3.6:s:6H; 6.75:d:2H; 6.85:ss:1H; 7.1–7.35:u.c.:2H; 7.45:t:1H; 7.57:d:1H.

Preparation 4.23

5-(2,6-Dimethoxyphenyl)-1-(5-[N-methyl-N-(3-(N',N'-dimethylamino)propyl)carbamoyl]-2-methylphenyl)-3-pyrazolecarboxylic acid.

(II: $R_1$=5-CONMe$(CH_2)_3$NMe$_2$; $R_2$=2-$CH_3$; $R_3$=H; $R_4$=$CH_3$).

A solution of 2.28 g of the product of Preparation 3.32 in 10 ml of dioxane is left stirring for 15 hours at RT with a solution of 0.65 g of KOH in 1.5 ml of water; the mixture is evaporated under vacuum, and the residue is then dissolved in 20 ml of water and extracted 3 times with 50 ml of ether. After acidification of the aqueous phase to pH 4 by adding 1N HCl, and azeotropic distillation with ethanol, the residue is triturated with 20 ml of ethanol, KCl is filtered off and the filtrate is then evaporated under vacuum. This removal of KCl is repeated, and the mixture is evaporated under vacuum to obtain 2 g of the expected product.

NMR: 1.9:u.c.:2H; 2.2:s:3H; 2.4–3:u.c.:11H; 3.5:mt:2H; 3.65:s:6H; 6.65:d:2H; 6.85:s:1H; 7.1:bs:1H; 7.3–7.5:u.c.:3H.

By following the above procedures, the acids of formula II described in Table 5 below are prepared.

TABLE 5

II

| Preparation (from) | $R_1$ | $R_2$ | $R_3$ | M.p. °C. or NMR |
|---|---|---|---|---|
| 4.24 (3.33) | 4-CONMe$(CH_2)_2$NMe$_2$ | 2-OCH$_3$ | H | NMR |
| 4.25 (3.34) | 4-CO—N(piperazine)N—CH$_3$ | 2-OCH$_3$ | H | NMR |
| 4.26 (3.36) | 4-SO$_2$NMe$(CH_2)_3$NMe$_2$ | 2-CH$_3$ | 3-CH$_3$ | NMR |
| a) 4.27 (3.38) | 5-CONMe$(CH_2)_2$NMe$_2$ | 2-Cl | H | NMR |
| 4.28 (3.40) | 4-CONMe$(CH_2)_2$NEt$_2$ | 2-CF$_3$ | H | NMR |
| a) 4.29 (3.42) | 5-CONMe$(CH_2)_2$NMe$_2$ | 2-OCH$_3$ | H | NMR |
| 4.30 (3.43) | 4-CONH$(CH_2)_2$N(iPr)$_2$ | 2-iPr | H | NMR |
| a) 4.31 (3.45) | 4-CONH$(CH_2)_3$N(nBu)$_2$ | 2-iPr | H | NMR |
| a) 4.32 (3.46) | 4-CONH$(CH_2)_2$NEt$_2$ | 2-iPr | H | NMR |
| 4.33 (3.47) | 4-CONH—C(cyclopentyl)—CH$_2$NMe$_2$ | 2-iPr | H | NMR |
| 4.34 (3.48) | 4-CON(CH$_2$CH$_2$NEt$_2$)$_2$ | 2-iPr | H | NMR |
| 4.35 (3.49) | 4-CONHCH$_2$—(N-Et pyrrolidine) | 2-iPr | H | NMR |

TABLE 5-continued

Structure II: pyrazole with CO₂H, substituted with 2,6-dimethoxyphenyl and phenyl bearing R₁, R₂, R₃

| Preparation (from) | R₁ | R₂ | R₃ | M.p. °C. or NMR |
|---|---|---|---|---|
| 4.36 (3.50) | 4-CONH-(2,2,6,6-tetramethylpiperidin-4-yl) | 2-iPr | H | NMR |
| 4.37 (3.52) | 4-CO-N(piperidinyl-4-NMe₂) | 2-iPr | H | 196 |
| 4.38 (3.53) | 4-CONMe(CH₂)₂CN | 2-iPr | H | 178–180 NMR |
| 4.39 (3.55) | 4-SO₂N(CH₂)NMe₂ with Bz | 2-iPr | H | 140 |

The letter a) indicates that the potassium salt of the acid of the formula II was obtained.

NMR:

Preparation 4.24 (DMSO): 2:u.c.:2H; 2.5:u.c.:6H; 2.8–3.5:u.c.:5H; 3.5:s:3H; 3.6:s:6H; 6.6:d:2H; 6.8:s:1H; 7.05:u.c.:2H; 7.15:u.c.:2H.

Preparation 4.25: 2.1:s:3H; 2.3:u.c.:4H; 3.1 to 3.7:u.c.:13H; 6.5:d:2H; 6.7:s:1H; 6.9:u.c.:2H; 7.25:u.c.:2H.

Preparation 4.27: 1.6–3.2:u.c.:13H; 3.6:s:6H; 6.4:s:1H; 6.6.:d:2H; 7–8:u.c.:4H.

Preparation 4.28: 0.9:u.c.:6H; 2–3.4:u.c.:11H; 3.5:s:6H; 6.4:s:1H; 6.6:d:2H; 7.15:u.c.:2H; 7.75:d:14H; 7.85:bs:1H.

Preparation 4.29: 1.8–2.6:u.c.:8H; 2.8:bs:3H; 3.4–3.8:bs:2H; 3.6:s:6H; 3.64:s:3H; 6.50:s:1H; 6.60:d:2H; 7–7.50:u.c.:4H.

Preparation 4.30 (DMSO+TFA): 1:d:6H; 1.3:d:12H; 2.65:mt:1H; 3.2:t:2H; 3.5–3.75:u.c.+s:10H; 6.55:d:2H; 6.8:s:1H; 7.2–7.35:mt: 2H; 7.7:d:1H; 7.8:s:1H.

Preparation 4.31: 0.8:t:6H; 0.95:d:6H; 1.1–1.4:u.c.:8H; 1.58:t:2H; 2.15–2.4:u.c.:6H; 2.55:sp:1H; 3.2:mt:2H; 3.57:s:6H; 6.3:s:1H; 6.5:d:2H; 7.1–7.3:u.c.:2H; 7.74:dd:1H; 7.75:d:1H; 8.45:t:1H.

Preparation 4.32: 0.9–1.1:u.c.:12H; 2.6:u.c.:6H; 2.7:u.c.:1H; 3.2–3.4:u.c.:2H; 3.6:u.c.:6H; 6.3:s:1H; 6.6:d:2H; 7.1–7.3:u.c.:2H; 7.6–7.8:u.c.:2H.

Preparation 4.33: 1:d:6H; 1.5–1.9:u.c.:6H; 2–2.2:u.c.:2H; 2.2:s:6H; 2.7:s:2H; 2.8:qt:1H; 3.6:s:6H; 6.45:s:1H; 6.6:d:2H; 7.2–7.35:u.c.:2H; 7.6:d:1H; 7.7:s:1H; 7.9:s:1H.

Preparation 4.34: 1:m:12H; 1.3:mt:6H; 2.5–3.9:u.c.+s:23H; 6.6:d:2H; 6.8:s:1H; 7.2–7.4:u.c.:3H; 7.55:s:1H.

Preparation 4.35 (DMSO+TFA): 1:u.c.:6H; 1.2:t:3H; 1.75–2.2:2u.c.:4H; 2.65:mt:1H; 3:u.c.:2H; 3.4–3.7:u.c.+s:11H; 6.5:d:2H; 6.75:s:1H; 7.2:t:1H; 7.3:d:1H; 7.65:d:1H; 7.8:s:1H.

Preparation 4.36: 1.05:d:6H; 1.5:s:12H; 1.7:t:2H; 2.0:d:2H; 2.7:mt:1H; 3.7:s:6H; 4.3–4.5u.c.:1H; 6.7:d:2H; 6.85:s:1H; 7.25–7.4:mt:2H; 7.75:d:1H; 7.9:s:1H; 8.3–8.5:u.c.:1H; 8.7:d:1H; 12.8:u.c.:1H.

Preparation 4.38: 0.95:d:6H; 2.6:mt:1H; 2.7–3.8:u.c.:13H; 6.57:d:2H; 6.75:s:1H; 7.12–7.35:u.c.:4H; 12.7:bs:1H.

Preparation 4.40

1-[4-[N-Ethyl-N-(2-N',N'-diethylaminoethyl)carbamoyl]-2-isopropylphenyl]-5-(2,6-dimethoxyphenyl)-3-pyrazolecarboxylic acid.

(II: R₁=4-CONEt(CH₂)₂NEt₂; R₂=2-iPr; R₃=H; R₄=CH₃).

A solution of 0.48 g of the compound obtained in Preparation 4.32 and 0.28 ml of ethyl iodide in 3 ml of THF is cooled to 5° C., 0.063 g of 60% sodium hydride in oil is then added portionwise and the mixture is left stirring for 24 hours at RT. 0.48 ml of a THF/water (50:50; v/v) mixture is added and the reaction mixture is concentrated under vacuum. The residue is taken up with water, the aqueous phase is washed twice with pentane, acidified to pH 1 by adding 1N HCl solution and extracted with AcOEt and then with DCM, the organic phases are dried over Na₂SO₄ and the solvents are evaporated off under vacuum. 0.14 g of the expected product is obtained.

NMR (DMSO+TFA): 0.8–1.3:u.c.:15H; 2.6:u.c.:1H; 3.0–3.8:u.c.:16H; 6.5:d:2H; 6.75:s:1H; 7.2:u.c.:4H.

Preparation 4.41

1-[4-[[3-(Diethylamino)-1-pyrrolidinyl]carbonyl]-2-isopropylphenyl]-5-(2,6-dimethoxyphenyl)-3-pyrazolecarboxylic acid hydrochloride.

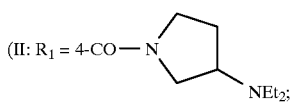

(II: R₁ = 4-CO—N(pyrrolidinyl-NEt₂);

A solution of 0.11 g of KOH in 0.5 ml of water is added at RT to a solution of 0.44 g of the compound obtained in Preparation 3.51 in 4 ml of dioxane, and the mixture is left stirring overnight at RT. It is concentrated under vacuum, the residue is taken up with water, the aqueous phase is washed twice with ether and acidified to pH 2 by adding 1.2 N HCl, EtOH is added and the mixture is concentrated under vacuum. The residue is taken up with EtOH, the KCl is filtered off and the filtrate is concentrated under vacuum. 0.39 g of the expected product is obtained.

NMR (DMSO+TFA): 1.0:d:6H; 1.15–1.35:u.c.:6H; 2.1–2.45:u.c.:2H; 2.65:mt:1H; 2.9–4.1:3u.c.+s:15H; 6.6:d:2H; 6.8:s:1H; 7.2–7.5:mt:3H; 7.55:s:1H.

Preparation 4.42

1-[4-[N-(2-Propenyl)carbamoyl]-2-isopropylphenyl]-5-(2,6-dimethoxyphenyl)-3-pyrazolecarboxylic acid.

(II: R₁=4-CONHCH₂CH=CH₂; R₂=2-iPr; R₃=H; R₄=CH₃).

A mixture of 1.72 g of the compound obtained in Preparation 3.54 and 0.78 g of LiOH.H₂O in 10 ml of MeOH and 1 ml of water is left stirring for 7 hours at RT. It is concentrated under vacuum, the residue is taken up with water, the aqueous phase is washed twice with ether, acidified to pH 2–3 by adding 1.2 N HCl and extracted with DCM, the organic phase is dried over MgSO$_4$ and the solvent is evaporated off under vacuum. 1.64 g of the expected product are obtained.

NMR: 1.0:d:6H; 2.7:qt:1H; 3.7:s:6H; 3.95:t:2H; 5.1–5.3:u.c.:2H; 5.8–6.1:u.c.:1H; 6.65:d:2H; 6.85:s:1H; 7.25–7.4:u.c.:2H; 7.75:d:1H; 7.9:s:1H; 8.8:t:1H.

Preparation 4.43

1-[4-[N-Methyl-N-[3-[N'-methyl-N'-(tert-butoxycarbonyl)amino]propyl]carbamoyl]-2-isopropylphenyl]-5-(2,6-dimethoxyphenyl)-3-pyrazolecarboxylic acid.

(II: R$_1$=4-CONMe(CH$_2$)$_3$N(Me)COOt-Bu; R$_2$=2-iPr; R$_3$=H; R$_4$=CH$_3$).

A mixture of 2.85 g of the compound obtained in Preparation 3.57 and 0.98 g of LiOH.H$_2$O in 20 ml of MeOH and 1 ml of water is left stirring for 3 hours 30 minutes at RT. It is concentrated under vacuum, the residue is taken up with water and acidified to pH 2 by adding a pH 2 buffer solution, and the precipitate formed is drained and washed with water. 2.47 g of the expected product are obtained after drying over P$_2$O$_5$, m.p.=112–114° C.

Preparation 4.44

1-[4-(4-Methylphenylsulphonylamino)-2-isopropylphenyl]-5-(2,6-dimethoxyphenyl]-3-pyrazolecarboxylic acid.

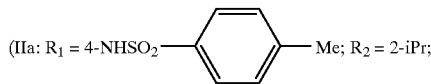

(IIa: R$_1$ = 4-NHSO$_2$—⟨⟩—Me; R$_2$ = 2-iPr;

A mixture of 1.05 g of the compound obtained in Preparation 3.58 and 0.33 g of LiOH.H$_2$O in 5 ml of MeOH and 0.5 ml of water is heated for 3 hours at 60° C. The reaction mixture is poured into water, the resulting mixture is acidified to pH 2–3 by adding 10% HCl solution, and the precipitate formed is drained and dried. 0.92 g of the expected product is obtained.

NMR: 0.7:d:6H; 2.3–2.6:u.c.:4H; 3.55:s:6H; 6.6:d:2H; 6.75:s:1H; 6.85–7.01:u.c.:2H; 7.11:d:1H; 7.25–7.42:u.c.:3H; 7.6:d:2H; 10.3:s:1H; 12.75:bs:1H.

Preparation 4.45

1-(4-Amino-2-isopropylphenyl)-5-(2,6-dimethoxyphenyl)-3-pyrazolecarboxylic acid.

(II': R'$_1$=4-NH$_2$; R$_2$=2-iPr; R$_3$=H; R$_4$=Me).

A mixture of 0.9 g of the compound obtained in Preparation 3.58, 11 ml of acetic acid and 25 ml of 70% perchloric acid is heated to reflux for 10 minutes. The reaction mixture is poured into a water/ice mixture, some insoluble matter is filtered off, the filtrate is taken to pH 5 by adding 10% NaOH and filtered, the filtrate is extracted with AcOEt, the organic phase is dried over Na$_2$SO$_4$ and the solvent is evaporated off under vacuum. The residue is taken up with ether and the precipitate formed is drained. 0.54 g of the expected product is obtained, m.p.=190° C. (dec.).

NMR: 0.92:d:6H; 2.42:mt:1H; 3.65:s:6H; 5.42:bs:2H; 6.3:dd:1H; 6.4:d:1H; 6.6:d:2H; 6.67:s:1H; 6.85:d:1H; 7.3:t:1H.

Preparation 4.46

1-[4-[3-(Diethylamino)propanoylamino]-2-isopropylphenyl]-5-(2,6-dimethoxyphenyl)-3-pyrazolecarboxylic acid.

(II: R$_1$=4-NHCO(CH$_2$)$_2$NEt$_2$; R$_2$=2-iPr; R$_3$=H; R$_4$=Me).

A mixture of 0.22 g of 3-diethylaminopropanoic acid hydrochloride and 2 ml of SOCl$_2$ in 2 ml of DCM is heated to reflux for 1 hour and then concentrated under vacuum. The acid chloride thereby obtained is used without further treatment. Separately, a mixture of 0.47 g of the compound obtained in Preparation 4.45 and 0.95 ml of bis(trimethylsilyl)acetamide in 5 ml of acetonitrile is heated at 70° C. for 1 hour. After cooling to RT, the acid chloride prepared above, in solution in DCM, is added, followed by 0.17 ml of triethylamine, and the mixture is left stirring for 1 hour at RT. It is concentrated under vacuum, the residue is taken up with water, the pH is taken to 5 by adding 10% NaOH, the mixture is extracted with DCM, the organic phase is dried over Na$_2$SO$_4$ and the solvent is evaporated off under vacuum. The residue is taken up with ether and the precipitate formed is drained. 0.27 g of the expected product is obtained.

NMR (DMSO+TFA): 0.91:d:6H; 1.2:mt:6H; 2.55:mt:1H; 2.8:t:2H; 3.1–3.22:u.c.:4H; 3.35:t:2H; 3.6:s:6H; 6.58:d:2H; 6.75:s:1H; 7.1–7.3:u.c.:2H; 7.4–7.55:u.c.:2H.

Preparation 4.47

1-[4-[(3-Diethylaminopropyl)amino]-2-isopropylphenyl]-5-(2,6-dimethoxyphenyl)-3-pyrazolecarboxylic acid.

(II: R$_1$=4-NH(CH$_2$)$_3$NEt$_2$; R$_2$=2-iPr; R$_3$=H; R$_4$=Me).

A mixture of 0.55 g of the compound obtained in Preparation 3.59, 6.5 ml of acetic acid and 14 ml of 70% perchloric acid is heated to reflux for 10 minutes. The reaction mixture is poured into water, the resulting mixture is taken to pH 5 by adding 10% NaOH and extracted with AcOEt, the organic phase is dried over Na$_2$SO$_4$ and the solvent is evaporated off under vacuum. 0.5 g of the expected product is obtained.

NMR: 1.0:mt:6H; 1.25:t:6H; 1.9:mt:2H; 2.55:s:1H; 3.0–3.3:u.c.:8H; 3.7:s:6H; 5.9:s:1H; 6.3–6.55:u.c.:2H; 6.65:d:2H; 6.75:s:1H; 7.0:d:1H; 7.3:t:1H.

Preparation 4.48

1-[4-[N-Acetyl-N-(3-diethylaminopropyl)amino]-2-isopropylphenyl]-5-(2,6-dimethoxyphenyl)-3-pyrazolecarboxylic acid.

(II: R$_1$=4-N(COMe)(CH$_2$)$_3$NEt$_2$; R$_2$=2-iPr; R$_3$=H; R$_4$=Me).

0.38 g of the compound obtained in Preparation 4.47 and 0.36 ml of bis(trimethylsilyl)acetamide in 10 ml of toluene is heated for 1 hour at 60° C. 0.052 ml of acetyl chloride is added, followed by 0.1 ml of triethylamine, and the mixture is left stirring for 2 hours at RT. It is concentrated under vacuum, the residue is taken up with saturated NaCl solution, the mixture is extracted with AcOEt, the organic phase is dried over Na$_2$SO$_4$ and the solvent is evaporated off under vacuum. 0.39 g of the expected product is obtained.

NMR: 0.95:d:6H; 1.25:t:6H; 1.6–2.0:u.c.:5H; 2.65:sp:1H; 3.0–3.3:u.c.:6H; 3.65:s:6H; 3.75:t:2H; 6.65:d:2H; 6.85:s:1H; 7.2–7.6:u.c.:4H.

Preparation 4.49

1-[4-[N-methyl-N-(3-dimethylaminopropyl)carbamoyl]-2-isopropylphenyl]-5-[2-(cyclopropylmethyloxy)-6-methoxyphenyl]-3-pyrazolecarboxylic acid potassium salt.

(II: R$_1$ = 4-CONMe(CH$_2$)$_3$NMe$_2$; R$_2$ = 2-iPr; R$_3$ = H; R$_4$ = —CH$_2$—◁).

A mixture of 3.8 g of the compound obtained in Preparation 3.61 and 0.92 g of KOH in 76 ml of EtOH and 12 ml of water is left stirring for 20 hours at RT. It is concentrated under vacuum, the residue is taken up with toluene and the solvent is evaporated off under vacuum. 3.9 g of the expected product are obtained.

Preparation 4.50

1-(2-Methyl-4-nitrophenyl)-5-(2,6-dimethoxyphenyl)-3-pyrazolecarboxylic acid.

(II': R'$_1$=4-NO$_2$; R$_2$=2-Me; R$_3$=H; R$_4$=Me).

A mixture of 3.5 g of the compound obtained in Preparation 3.56 and 0.44 g of LiOH.H$_2$O in 20 ml of MeOH and 4 ml of water is left stirring overnight. It is concentrated under vacuum, the residue is taken up with water, the mixture is acidified to pH 3 by adding 10% HCl, and the precipitate formed is drained and dried. 3.2 g of the expected product are obtained.

NMR: 2.9:s:3H; 3.58:s:6H; 6.6:d:2H; 6.88:s:1H; 7.2–7.38:u.c.:2H; 7.95:dd:1H; 8.22:d:1H.

Preparation 4.51

1-(4-Amino-2-isobutylphenyl)-5-(2,6-dimethoxyphenyl)-3-pyrazolecarboxylic acid.

(II': R'$_1$=4-NH$_2$; R$_2$=2-iBu; R$_3$=H; R$_4$=Me).

This compound is prepared according to the procedure described in Preparation 4.45, from 0.5 g of the compound obtained in Preparation 3.62, 6 ml of acetic acid and 14 ml of 70% perchloric acid. 0.3 g of the expected product is obtained.

NMR: 0.65:d:6H; 1.55:mt:1H; 1.9:d:2H; 3.5:s:6H; 5.05:s:2H; 6.0–7.3:u.c.:7H.

Preparation 4.52

1-[4-[3-(Diethylamino)propanoylamino]-2-isobutylphenyl]-5-(2,6-dimethoxyphenyl)-3-pyrazolecarboxylic acid.

(II: R$_1$=4-NHCO(CH$_2$)$_2$NEt$_2$; R$_2$=2-iBu; R$_3$=H; R$_4$=Me).

This compound is prepared according to the procedure described in Preparation 4.46, from 0.133 g of 3-diethylaminopropanoic acid hydrochloride and 1 ml of SOCl$_2$ in 1 ml of DCM and 0.29 g of the compound obtained in Preparation 4.51 and 4 ml of bis(trimethylsilyl)acetamide in 2 ml of acetonitrile. 0.15 g of the expected product is obtained.

NMR: 0.7:d:6H; 1.1:t:6H; 1.65:mt:1H; 2.0:d:2H; 2.75:t:2H; 3.1:qr:4H; 3.3:t:2H; 3.6:s:6H; 6.5:d:2H; 6.7:s:1H; 7.1:d:1H; 7.2:t:1H; 7.3–7.5:u.c.:2H; 10.3:s:1H; 15:s:1H.

Preparation 4.53

1-[4-Amino-2-cyclopentylphenyl)-5-(2,6-dimethoxyphenyl)-3-pyrazolecarboxylic acid.

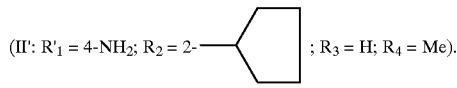

(II': R'$_1$ = 4-NH$_2$; R$_2$ = 2- ; R$_3$ = H; R$_4$ = Me).

This compound is prepared according to the procedure described in Preparation 4.45, from 0.9 g of the compound obtained in Preparation 3.63, 11 ml of acetic acid and 27 ml of 70% perchloric acid. 0.52 g of the expected product is obtained.

NMR (DMSO+TFA): 1.18–1.9:u.c.:8H; 2.6:mt:1H; 3.6:s:6H; 6.6:d:2H; 6.75:s:1H; 7.1–7.4:u.c.:4H.

Preparation 4.54

1-[4-[3-(Diethylamino)propanoylamino]-2-cyclopentylphenyl]-5-(2,6-dimethoxyphenyl)-3-pyrazolecarboxylic acid.

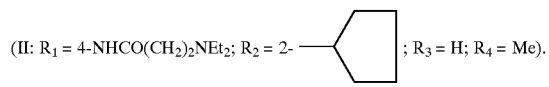

(II: R$_1$ = 4-NHCO(CH$_2$)$_2$NEt$_2$; R$_2$ = 2- ; R$_3$ = H; R$_4$ = Me).

This compound is prepared according to the procedure described in Preparation 4.46, from 0.22 g of 3-diethylaminopropanoic acid hydrochloride, 2 ml of SOCl$_2$ in 5 ml of DCM, 0.5 g of the compound obtained in Preparation 4.53 and 0.73 ml of bis(trimethylsilyl)acetamide in 2 ml of acetonitrile. 0.32 g of the expected product is obtained.

NMR (DMSO+TFA): 1.1–1.8:u.c.:14H; 2.5:mt:1H; 2.72:t:2H; 3.02:u.c.:4H; 3.22:mt:2H; 3.58:s:6H; 6.5:d:2H; 6.65:s:1H; 7.03:d:1H; 7.2:t:1H; 7.35:dd:1H; 7.5:d:1H.

Preparation 4.55

1-[4-[N-(2-Diethylaminoethyl)carbamoyl]-3-isopropylphenyl]-5-(2,6-dimethoxyphenyl)-3-pyrazolecarboxylic acid potassium salt.

(II: R$_1$=4-CONH(CH$_2$)$_2$NEt$_2$; R$_2$=3-iPr; R$_3$=H; R$_4$=Me).

0.34 g of the compound obtained in Preparation 3.65 and 0.073 g of KOH in 6 ml of dioxane and 2 ml of water is left stirring for 2 days at RT. It is concentrated under vacuum, the residue is taken up with toluene and the mixture is concentrated under vacuum. 0.37 g of the expected product is obtained, m.p.>260° C.

Preparation 4.56

5-(2,6-Dimethoxyphenyl)-1-(4-nitro-5,6,7,8-tetra-hydro-1-naphthyl)-3-pyrazolecarboxylic acid.

(II': R'$_1$=4-NO$_2$; R$_2$, R$_3$=—(CH$_2$)$_4$—; R$_4$=Me).

A mixture of 4.2 g of the compound obtained in Preparation 3.66 is heated at 70° C. for 2 hours with 0.8 g of LiOH.H$_2$O in 95 ml of EtOH and 5 ml of water. After cooling to RT, water is added, the mixture is acidified to pH 3 by adding 10% HCl, and the precipitate formed is drained and dried. 4.16 g of the expected product are obtained, m.p.=130° C.

NMR: 1.7:mt:4H; 2.55:mt:2H; 2.82:mt:2H; 3.65:s:6H; 6.65:d:2H; 6.85:s:1H; 7.05:d:1H; 7.35:t:1H; 7.7:d:1H; 12.95:bs:1H.

Preparation 4.57

5-(2,6-Dimethoxyphenyl)-1-(5-(3-diethylaminopropanoylamino)-2-isopropylphenyl)-3-pyrazolecarboxylic acid.

(II: R$_1$=5-NHCO(CH$_2$)$_2$NEt$_2$; R$_2$=2-iPr; R$_3$=H; R$_4$=CH$_3$).

This compound is obtained from the methyl ester of Preparation 3.67. After recrystallization in methanol, m.p.=195–198° C.

NMR (DMSO+TFA): 0.65–1.35:u.c.:12H; 2.5:qt:1H; 2.82:t:2H; 3.15:mt:4H; 3.36:t:2H; 3.6:s:6H; 6.55:d:2H; 6.76:s:1H; 7.15–7.4:u.c.:3H; 7.8:d:1H.

EXAMPLE 1

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid hydrochloride.

(I: R$_1$=4-CONMe(CH$_2$)$_3$NMe$_2$; R$_2$=2-iPr; R$_3$=H; R$_4$=CH$_3$; AA(OH)=2-carboxy-2-adamantyl).

A) 1-[4-[N-Methyl-N-(3-dimethylaminopropyl)carbamoyl]-2-isopropylphenyl]-5-(2,6-dimethoxyphenyl)3-pyrazolylcarbonyl chloride hydrochloride.

1.07 g of the acid obtained in Preparation 4.1 in 2 ml of thionyl chloride is left stirring under nitrogen at RT for 5 hours. The mixture is evaporated, and the residue is then taken up with DCM (3 times) to obtain the expected product, which is used in the next step without further treatment.

The acid chloride may also be prepared according to the procedure below:

A') 1-[4-[N-Methyl-N-(3-dimethylaminopropyl) carbamoyl]-2-isopropylphenyl]-5-(2,6-dimethoxyphenyl)3-pyrazolylcarbonyl chloride hydrochloride.

The potassium salt of Preparation 4.1a is redissolved in 130 ml of ethanol, 50 ml of ethanolic hydrogen chloride are added, the inorganic matter is filtered off and the filtrate is evaporated under vacuum. The residue is redissolved in 100 ml of DCM, 11 ml of $SOCl_2$ are added slowly and the mixture is heated to reflux for 4 hours. It is evaporated under vacuum, the residue is redissolved in 30 ml of DCM and the mixture is evaporated under vacuum; the operation is repeated 3 times.

B) 2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid hydrochloride.

A mixture containing 0.37 g of 2-amino-2-adamantanecarboxylic acid (compound B), 5 ml of acetonitrile and 0.82 ml of bis(trimethylsilyl)acetamide is heated to reflux under nitrogen for 40 minutes. After a return to RT, 0.3 ml of triethylamine and the product obtained in the preceding step, dissolved in 15 ml of acetonitrile, are added. The mixture is left stirring at RT for 1 week and the solvents are concentrated. On adding ether, a crystallization is obtained. The crystals are stirred in a mixture of 1.5 ml of toluene and 1.5 ml of acetonitrile. The insoluble matter is filtered off and rinsed and the solvents are evaporated off. The residue is stirred in aqueous methanol, the mixture is then evaporated again and the residue is taken up with ethanol. The mixture is extracted with DCM, and the organic phase is washed with saturated NaCl solution and then chromatographed on silica, eluting with a $DCM/MeOH/H_2O$ (92:8:0.7; v/v/v) mixture. 0.18 g of the expected product is obtained after trituration in ether, m.p.=185° C. (dec.).

NMR (DMSO+TFA): 0.95:d:6H; 1.6–2.2:u.c.:14H; 2.4–3:u.c.:12H; 3.1:mt:2H; 3.5:mt:2H; 3.65:s:6H; 6.6:d:2H; 6.7:s:1H; 7.1–7.5:u.c.:4H.

Alternatively, step B may be performed in the following manner:

A mixture of 8.79 g of compound B and 22 ml of bis(trimethylsilyl)acetamide in 120 ml of dry acetonitrile is heated to reflux under nitrogen for 40 minutes and cooled to RT. A solution of the acid chloride obtained according to A, starting from 23.83 g of the acid obtained in Preparation 4.1 and 140 ml of thionyl chloride, in 300 ml of dry acetonitrile is then added. After stirring for 15 hours at RT and evaporation under vacuum, the residue is redissolved in 180 ml of MeOH, 180 ml of water are added slowly, the mixture is stirred for one hour, the insoluble matter is filtered off and the filtrate is evaporated under vacuum after adding ethanol. After stirring in 200 ml of 1N HCl, the mixture is filtered, and the precipitate is washed with 1N HCl and dried under vacuum over $P_2O_5$ to obtain 29.8 g of the product of EXAMPLE 1, m.p.=211° C. (dec.) after recrystallization in 2-propanol. EXAMPLE 1'

Internal salt of 2-[5-(2,6-dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid.

From the hydrochloride of the compound obtained in EXAMPLE 1, the internal salt is liberated in the following manner:

0.97 g of the product of EXAMPLE 1 is dissolved in 10 ml of water and the pH is raised to 7 by adding 1.3N sodium hydroxide. The product is filtered off, washed with water and dried under vacuum over $P_2O_5$ to obtain 0.86 g of internal salt, which is recrystallized in 3 ml of acetonitrile to obtain 0.5 g of the expected internal salt.

NMR (DMSO+TFA): 1:mt:6H; 1.4–2.3:u.c.:14H; 2.3–3.4:u.c.:14H; 3.5:u.c.:2H; 3.65:s:6H; 6.6:d:2H; 6.7:s:1H; 7.1–7.5:u.c.:4H.

After recrystallization in 2-propanol, m.p.=238° C.

NMR (DMSO+TFA): 1.05:d:6H; 1.5–2.2:u.c.:14H; 2.5:bs:2H; 2.6–3:u.c.:10H; 3.1:mt:2H; 3.5:mt:2H; 3.6:s:6H; 6.6:d:2H; 6.75:s:1H; 7.1–7.5:u.c.:4H.

The product of EXAMPLE 1' may also be prepared without isolating the product of EXAMPLE 1, according to the following procedure:

A mixture of 9.7 g of compound B and 27 ml of bistrimethylsilylacetamide in 100 ml of anhydrous DCM is heated to reflux under nitrogen for 2 hours. After cooling, the solution thereby obtained is poured into the solution of the product of step A' of EXAMPLE 1 in 100 ml of DCM, and the mixture is stirred overnight at RT. It is evaporated under vacuum, the residue is treated by stirring for 3 hours with 100 ml of MeOH and 100 ml of water and the pH is raised to 7–7.5 by adding saturated $NaHCO_3$ solution. After 1 hour of stirring, the mixture is filtered to obtain 22.1 g of the expected product (HPLC purity 98.5%).

The internal salt may also be converted to its hydrochloride (product of EXAMPLE 1) according to the following procedure:

6.85 g of internal salt in a mixture of 3.5 ml of concentrated HCl and 40 ml of water are heated while stirring. After dissolution, the mixture is allowed to cool with stirring, and the product is filtered off and dried under vacuum to obtain 6.5 g of hydrochloride.

From the internal salt, its hydrochloride may be obtained in the following manner:

0.3 g of internal salt in 3 ml of MeOH and 2 ml of DCM are dissolved while heating, the mixture is cooled to RT, 0.5 ml of 1.2N HCl is added, the mixture is concentrated under vacuum to 0.5 ml and cooled to −20° C. and the product is filtered off to obtain 0.2 g of the product of EXAMPLE 1.

EXAMPLE 2

2-{1-[4-[N-(2-Cyanoethyl)carbamoyl]-2-isopropylphenyl]-5-(2,6-dimethoxyphenyl)-3-pyrazolylcarbonylamino}-2-adamantanecarboxylic acid.

(I: $R_1$=4-$CONHCH_2CH_2CN$; $R_2$=2-iPr; $R_3$=H; $R_4$=$CH_3$; AA(OH)=2-carboxy-2-adamantyl).

A mixture of 2.6 g of the compound obtained in Preparation 4.2 and 20 ml of thionyl chloride is left stirring for 5 hours at RT. It is concentrated under vacuum, the residue is taken up with DCM and the solvent is evaporated off under vacuum. The acid chloride thereby obtained is used without further treatment. Separately, a mixture of 1.09 g of 2-amino-2-adamantanecarboxylic acid and 4.2 ml of bis(trimethylsilyl)acetamide in 20 ml of acetonitrile is heated to reflux under a nitrogen atmosphere for 30 minutes. After cooling, a solution of the acid chloride prepared above in 40 ml of acetonitrile is added slowly, and the mixture is left stirring overnight at RT. It is concentrated under vacuum, the residue is taken up with MeOH, a few drops of water are added and the mixture is left stirring for 2 hours at RT. The precipitate is drained, washed with MeOH and dried. The precipitate is chromatographed on silica H, eluting with a DCM/MeOH (100:3; v/v) mixture and then with a DCM/MeOH/AcOH (100:3:0.5; v/v/v) mixture. 1.96 g of the expected product are obtained after crystallization in ether, m.p.=269° C.

NMR: 1:d:6H; 1.4–2.1:u.c.:12H; 2.4–2.8:u.c:5H; 3.4:mt:2H; 3.5:s:6H; 6.5:d:2H; 6.6:s:1H; 7.1–7.4:u.c.:2H; 7.5:d:1H; 7.8:s: 1H; 8.9:t:1H.

EXAMPLE 3

2-{1-[4-[N-(3-Aminopropyl)carbamoyl]-2-isopropylphenyl]-5-(2,6-dimethoxyphenyl)-3-pyrazolylcarbonylamino}-2-adamantanecarboxylic acid.

(I: $R_1$=4-CONH(CH$_2$)$_3$NH$_2$; $R_2$=2-iPr; $R_3$=H; $R_4$=CH$_3$; AA(OH)=2-carboxy-2-adamantyl).

A mixture of 0.3 g of the compound obtained in EXAMPLE 2 and 0.03 g of Raney® nickel in 10 ml of MeOH is hydrogenated overnight at RT and at atmospheric pressure, the catalyst is filtered off and washed with MeOH and the filtrate is partially concentrated under vacuum. The crystals formed are filtered off and washed with EtOH to obtain a first crop of the expected product. The filtrate is partially concentrated under vacuum and left stirring at RT. The crystals formed are drained and washed with EtOH to obtain a second crop. By combining both crops, 0.045 g of the expected product are obtained, m.p.=280° C. (dec.).

NMR: 1.1:d:6H; 1.5–2.2:u.c.:14H; 2.4–3:u.c.:5H; 3.3:mt:2H; 3.6:s:6H; 6.6:d:2H; 6.7:s:1H; 7.2–7.4:u.c.:2H; 7.6:d:1H; 7.7:s:1H.

EXAMPLE 4

2-{1-[4-[N-(2-Amidinoethyl)carbamoyl]-2-isopropylphenyl]-5-(2,6-dimethoxyphenyl)-3-pyrazolylcarbonylamino}-2-adamantanecarboxylic acid.

(I: $R_1$=4-COHN(CH$_2$)$_2$C(=NH)NH$_2$; $R_2$=2-iPr; $R_3$=H; $R_4$=CH$_3$; AA(OH)=2-carboxy-2-adamantyl)

Step A. A solution of 0.37 g of the compound obtained in EXAMPLE 2 in 10 ml of EtOH and 10 ml of anhydrous ether is cooled in an ice bath, and HCl gas is then bubbled through it for 50 minutes. The mixture is left for 3 days at +5° C. and then concentrated under vacuum to obtain the hydrochloride of the intermediate imidate (R$_1$=4-CONH (CH$_2$)$_2$C(=NH)OEt).

Step B. The residue is taken up in 20 ml of anhydrous EtOH, the mixture is cooled in an ice bath and ammonia is bubbled through it for 35 minutes. The mixture is left stirring for 30 minutes at RT and concentrated under vacuum, the residue is taken up in water and crystallization is allowed to take place. After draining and then drying the crystals, the product is recrystallized in EtOH in the heated state. 0.3 g of the expected product is obtained, m.p.=257° C. (dec.).

NMR (DMSO+TFA): 1.1:d:6H; 1.5–2.2:u.c.:14H; 2.4–2.8:u.c.:3H; 3.4–3.7:u.c.+s:8H; 6.6:d:2H; 6.7:s:1H; 7.2–7.4:u.c.:2H; 7.6:dd:1H; 7.8:bs:1H.

EXAMPLE 5

2-[5-(2,6-Dimethoxyphenyl)-1-[4-[N-(2-dihydroimidazol-2-yl-ethyl)carbamoyl]-2-isopropylphenyl]-3-pyrazolylcarbonylamino]-2-adamantanecarboxylic acid dihydrochloride.

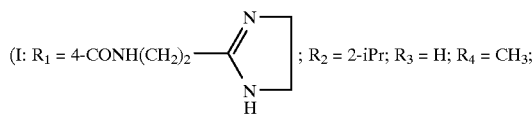

(I: $R_1$ = 4-CONH(CH$_2$)$_2$— ; $R_2$ = 2-iPr; $R_3$ = H; $R_4$ = CH$_3$;

AA(OH)=2-carboxy-2-adamantyl)

A mixture containing 0.49 g of the intermediate imidate described in EXAMPLE 4, step A and 5 ml of 1,2-diaminoethane is stirred for 30 minutes. The reaction medium is evaporated. On adding water, a precipitate forms which is filtered off and then rinsed with water. This product is suspended in ethanol and ethereal hydrogen chloride is added. After evaporation of the solvent, the product is triturated in ether, filtered off, rinsed with ether and then dried at 60° C over P$_2$O$_5$. 0.3 g of the expected product is obtained, m.p.=220° C. (dec.).

NMR: 1.05:d:6H; 1.5–2.2:u.c.:12H; 2.5:bs:2H; 2.6–2.8:u.c.:3H; 3.55:mt:2H; 3.65:s:6H; 3.8:s:1H; 6.6:d:2H; 6.7:s:1H; 7.2–7.4:dd:1H; 7.8:d:1H.

EXAMPLE 6

2-[5-(2,6-Dimethoxyphenyl)-1-[4-[N-(3-(N',N'-dimethylaminopropyl)carbamoyl]-2-isopropylphenyl]-3-pyrazolylcarbonylamino]-2-adamantanecarboxylic acid hydrochloride.

(I: $R_1$=4-CONH(CH$_2$)$_3$NMe$_2$; $R_2$=2-iPr; $R_3$=H; $R_4$=Me; AA(OH)=2-carboxy-2-adamantyl).

A mixture is prepared containing 1.45 g of the compound of Preparation 4.3, 30 ml of DCM, 0.38 ml of isobutyl chloroformate, 0.82 ml of triethylamine and 17 ml of acetonitrile. The mixture is left stirring at RT for five and a half hours. Separately, 0.57 g of 2-amino-2-adamantanecarboxylic acid, 10 ml of acetonitrile and 2.2 ml of bis(trimethylsilyl)acetamide are mixed, and the mixture is heated to reflux under nitrogen for 30 minutes. After cooling, the mixed anhydride formed above is added and the resulting mixture is left stirring at RT for 1 day. The insoluble matter is filtered off and removed; the solvents are evaporated off, water is then added, the mixture is stirred for 30 minutes and the precipitate formed is filtered off. A second fraction is obtained from the filtrate after adding ethanol, extraction with DCM (twice), drying over MgSO$_4$ and evaporation of the solvents. The 2 fractions combined are chromatographed on silica, eluting with a DCM/MeOH/H$_2$O (90:10:0.8, then 88:12:1; v/v/v) mixture. 40 mg of the expected product are obtained after trituration in isopropyl ether and filtration, m.p.=220° C. (dec.).

NMR (DMSO+TFA): 1.1:d:6H; 1.5 2.2:u.c.:14H; 2.5:bs:2H; 2.75:s+mt:7H; 3.1:u.c.:2H; 3.3:u.c.:2H; 3.65:s:6H; 6.6:d:2H; 6.7:s:1H; 7.2–7.4:u.c.:2H; 7.6:dd:1H; 7.8:d:2H.

From the acids of formula (II) described in Table 4, and by working according to the procedure described in EXAMPLE 1, the compounds according to the invention of formula (I) described in Table 6 below are obtained.

TABLE 6

(I)

| EXAMPLE | R₁ | M.p. °C. or NMR |
|---|---|---|
| 7 | —CONH(CH₂)₂NMe₂ | 210 NMR |
| 8 | —CONH(CH₂)₃NEt₂ | 185 NMR |
| 9 | 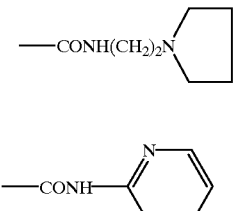 | 205 NMR |
| 10 | 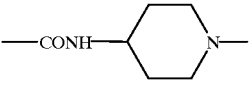 | 240 NMR |
| 11 | —CONHCH₂—C(Me)(Me)—CH₂NMe₂ | >260 NMR |
| 12 (a) | —CONH—(piperidinyl)—N—CH₂C₆H₅ | 228 NMR |
| 13 (a) | 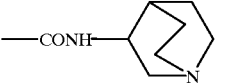 | 250 NMR |

(a) unsalified compounds.

NMR:

EXAMPLE 7

(DMSO+TFA): 1.1:d:6H; 1.5–2.2:u.c.:12H; 2.4–2.8:u.c.:3H; 2.8:s:6H; 3.25:mt:2H; 3.5–3.7:u.c.:8H; 6.6:d:2H; 6.7:s: 1H; 7.2–7.5:u.c.:2H; 7.7:dd:1H; 7.9:d:1H.

EXAMPLE 8

0.8–1.2:u.c.:12H; 1.4–2.2:u.c.:14H; 2.45:bs:2H; 2.6.:mt:1H; 2.8:mt:6H; 3.3:mt:2H; 3.5:s:6H; 6.5:d:2H; 6.65:s:1H; 7.1–7.4:u.c.:3H; 7.6:dd:1H; 7.8:bs:1H; 8.7:t:1H.

EXAMPLE 9

(DMSO+TFA): 0.8–1.3:u.c.:8H; 1.6–2.2:u.c.:14H; 2.3–2.8:u.c.:3H; 3:mt:2H; 3.2–3.8:u.c.:12H; 6.6:d:2H; 6.7:s:1H; 7.2–7.4:u.c.:2H; 7.65:d:1H; 7.9:bs:1H.

EXAMPLE 10

1.05:d:6H; 1.6–2.2:u.c.:12H; 2.5:bs:2H; 2.7:mt:1H; 3.6:s:6H; 6.6:d:2H; 6.7:s:1H; 7.05–7.25:u.c.:4H; 7.8–8.2:s:1H; 11:s:1H.

EXAMPLE 11

(DMSO+TFA): 1.1–1.3:u.c.:12H; 1.6–2.2:u.c.:12H; 2.6:bs:2H; 2.7:mt:1H; 2.9:s:6H; 3.05:bs:2H; 3.3:bs:2H; 3.7:s:6H; 6.65:d:2H; 6.75:s:1H; 7.25–7.45:u.c.:3H; 7.75:d:1H; 7.95:bs:1H.

EXAMPLE 12

1:d:6H; 1.3–2.1:u.c.:16H; 2.6:mt:1H; 2.75:mt:2H; 3.1–3.8:u.c.:5H; 3.4:s:2H; 3.6:s:6H; 6.5:d:2H; 6.6:s:1H; 7.1–7.3:u.c.:8H; 7.5:d:1H; 7.7:s:1H; 8.2:d:1H.

EXAMPLE 13

(DMSO+TFA): 1.05:d:6H; 1.3–2.3:u.c.:17H; 2.3–2.6:u.c.:2H; 2.65:mt:1H; 2.9–3.7:u.c.+s:12H; 4.2:u.c.:1H; 6.4:u.c.:2H; 6.7:bs:1H; 7.0–7.3:u.c.:2H; 7.4–7.6:u.c.:1H; 7.7:bs:1H.

EXAMPLE 14

2-[5-(2,6-Dimethoxyphenyl)-1-[4-[N-methyl-N-(3-N',N'-dimethylamino)propyl)aminosulphonyl]-2-isopropylphenyl]-3-pyrazolylcarbonylamino]-2-adamantanecarboxylic acid hydrochloride.

(I: R₁=4-SO₂NMe(CH₂)₃NMe₂; R₂=2-iPr; R₃=H; R₄=CH₃; AA(OH)=2-carboxy-2-adamantyl).

850 mg of the acid obtained in Preparation 4.11 and 3 ml of thionyl chloride are left stirring at RT for five and a half hours. 10 ml of toluene are added and the reaction medium is then evaporated under vacuum (twice). 1 g of chloride of the acid obtained in Preparation 4.11 is thereby obtained. A mixture containing 0.41 g of 2-amino-2-adamantanecarboxylic acid and 3.5 ml of bis(trimethylsilyl)acetamide in 5 ml of acetonitrile is left stirring for four and a half hours. A solution of the acid chloride prepared above in 5 ml of acetonitrile and 1 ml of triethylamine is added to this reaction medium, and the mixture is left stirring for 4 days at RT. 3 ml of water and 5 ml of methanol are added, the mixture is left stirring for 4 hours at RT and then filtered and the filtrate is evaporated under vacuum. The residue is triturated in 6 ml of 1N HCl, ethanol is then added and the mixture is evaporated under vacuum. The residue is stirred with 200 ml of DCM and 5 ml of water, settling is allowed to take place, and the organic phase is separated, dried over Na₂SO₄ and evaporated under vacuum to obtain 1.26 g of crude product. The latter is recrystallized in 5 ml of MeCN, the solution is cooled to –20° C. and 0.6 g of expected product is filtered off, m.p.=211° C.

NMR: 1:d:6H; 1.4–2.1:u.c.:14H; 2.4–2.5:mt:2H; 2.5–2.65:mt:1H; 2.6:s:3H; 2.65:s:6H; 2.9:mt:4H; 3.5:s:6H; 6.5:d:2H; 6.7:s:1H; 7.15–7.4:u.c.:3H; 7.45–7.6:u.c.:2H.

EXAMPLE 15

2-{5-(2,6-Dimethoxyphenyl)-1-[4-[N-[3-(N',N'-dimethylamino)propyl]carbamoyl]-5,6,7,8-tetrahydro-1-naphthyl]-3-pyrazolylcarbonylamino}-2-adamantanecarboxylic acid.

(I: R₁=4-CONH(CH₂)₃NMe₂; R₂, R₃=—(CH₂)₄—; R₄=Me; AA(OH)=2-carboxy-2-adamantyl).

0.47 g of the compound obtained in Preparation 4.12 in solution in 5 ml of SOCl₂ and 30 ml of DCM is heated for one and a half hours at 40° C. The mixture is evaporated under vacuum to obtain the acid chloride, which is redissolved in 5 ml of acetonitrile and added to the solution obtained by refluxing for 2 hours a mixture of 0.28 g of compound B, 0.69 ml of bis(trimethylsilyl)acetamide and 3 ml of acetonitrile. 0.26 ml of triethylamine is added and the mixture is left stirring for 2 hours ac RT. It is evaporated under vacuum, the residue is triturated in 2 ml of saturated NaCl solution, and the product is filtered and dried under vacuum to obtain 0.77 g. The product is chromatographed on silica H, eluting with a DCM/MeOH/water (80:20:2.5; v/v/v) mixture. The eluate is evaporated, and the residue is triturated in ether and filtered off to obtain 0.11 g of expected product, m.p.=200° C. (gum).

NMR: 1.4–2.05:u.c.:18H; 2.1:s:6H; 2.2:t:3H; 2.4–2.8:u.c.:6H; 3.2:qr:2H; 3.6:s:6H; 6.6:d:2H; 6.65:s:1H; 6.8–7:dd:2H; 7.2–7.3:u.c.:2H; 8.2:t:1H.

EXAMPLE 16

2-{5-(2,6-Dimethoxyphenyl)-1-[4-[N-methyl-N-(2-(N',N'-dimethylamino)ethyl)aminosulphonyl]-5,6,7,8-tetrahydro-1-naphthyl]-3-pyrazolylcarbonylamino}-2-adamantanecarboxylic acid hydrochloride.

(I: $R_1$=4-$SO_2$NMe$(CH_2)_2$NMe$_2$; $R_2$, $R_3$=—$(CH_2)_4$—; $R_4$=$CH_3$; AA(OH)=2-carboxy-2-adamantyl).

0.5 g of the salt obtained in Preparation 4.13 in 10 ml of $SOCl_2$ is left stirring for 15 hours at RT, and the mixture is then evaporated with toluene to obtain the acid chloride, into which a solution of the silylated compound B, obtained by stirring a mixture of 0.279 g of compound B, 2 ml of bis(trimethylsilyl)acetamide and 8 ml of acetonitrile for 6 hours at RT, is poured. After stirring for 20 days at RT, the mixture is evaporated under vacuum, and the residue is then stirred for 1 hour at RT with 5 ml of water and 5 ml of methanol; the mixture is filtered and the filtrate is evaporated under vacuum and then chromatographed on silica H, eluting with a DCM/MeOH/ACOH mixture. The residue is triturated in ether and filtered off to obtain 0.31 g of the expected product, m.p.>260° C.

NMR (DMSO+TFA): 1.6–2.3:u.c.:16H; 2.6:u.c.:2H; 2.9:bs:9H; 3.1:mt:2H; 3.4:mt:2H; 3.6:mt:2H; 3.7:s:6H; 6.7:d:2H; 6.85:s:1H; 7.15:d:1H; 7.4:t:1H; 7.5:bs:1H; 7.6:d:1H.

EXAMPLE 17

2-[5-(2,6-Dimethoxyphenyl)-1-(2-methyl-4-carbamoylphenyl)-3-pyrazolylcarbonylamino]-2-adamantanecarboxylic acid.

(I: $R_1$=4-$CONH_2$; $R_2$=2-$CH_3$; $R_3$=H; $R_4$=$CH_3$; AA(OH)=2-carboxy-2-adamantyl).

A suspension of 220 mg of compound B and 0.4 mg of bis(trimethylsilyl)acetamide in 10 ml of acetonitrile is heated to reflux for 1 hour.

Separately, a solution is prepared containing 330 mg of the compound obtained in Preparation 4.14 and 0.15 ml of triethylamine in 10 ml of acetonitrile and is cooled to –5° C., 0.13 ml of isobutyl chloroformate is added, the mixture is left stirring for 1 hour at RT, and the mixed anhydride obtained is added to the solution of the silylated compound B prepared above. The mixture is left for 8 days at RT, the insoluble matter is then filtered off, the filtrate is evaporated to dryness and the residue is then dissolved in 5 ml of DCM. The mixture is washed with 1.2 N HCl solution, dried over $Na_2SO_4$ and evaporated; 5 ml of DCM are added, and the precipitate formed is filtered off and then dissolved in 1 ml of MeOH. The crystals formed are filtered off to obtain 100 mg of the expected product, m.p.=290° C. (dec.).

NMR: 1.4–2.3:u.c.:15H; 2.55:u.c.:2H; 3.6:s:6H; 6.6:d:2H; 6.7:s:1H; 7.05:d:1H; 7.3:t:1H; 7.4:s:2H; 7.6:dd:1H; 7.75:s:1H; 7.9:s:1H.

EXAMPLE 18

2-{5-(2,6-Dimethoxyphenyl)-1-[2,3-dimethyl-4-[N-(2-(N',N'-dimethylamino)ethyl)carbamoyl]phenyl]-3-pyrazolylcarbonylamino}-2-adamantanecarboxylic acid.

(I: $R_1$=4-$CONH(CH_2)_2NMe_2$; $R_2$=2-$CH_3$; $R_3$=$CH_3$; $R_4$=$CH_3$; AA(OH)=2-carboxy-2-adamantyl).

A solution of 1.3 g of the product of Preparation 4.15 in 10 ml of $SOCl_2$ and 50 ml of DCM is heated to reflux for one and a half hours. It is evaporated under vacuum to obtain the acid chloride, which is redissolved in 10 ml of acetonitrile and added to the solution obtained after 2 hours of heating to reflux a mixture of 0.82 g of compound B and 2 ml of bis(trimethylsilyl)acetamide in 10 ml of acetonitrile. 0.77 ml of triethylamine is added and the mixture is left stirring for 15 hours at RT. After evaporation under vacuum, trituration in 10 ml of saturated NaCl solution, filtration and drying under vacuum, the product is chromatographed on silica H, eluting with a DCM/MeOH/water (100:10:1; v/v/v) mixture. After evaporation of the solvents and trituration in ether, the residue is filtered off to obtain 0.7 g of expected product, m.p.=210° C.

NMR: 1.6–2.2:u.c.:12H; 2:s:3H; 2.25 s:3H; 2.35:s:6H; 2.5–2.7:u.c.:2H+2H; 3.4:qr:2H; 3.7:s:6H; 6.65:d:2H; 6.8:s:1H; 7.0–7.2:u.c.:2H; 7.3–7.45:u.c.:2H; 8.4:t:1H.

EXAMPLE 19

2-{5-(2,6-Dimethoxyphenyl)-1-[4-[N-methyl-N-(2(N',N'-diethylamino)ethyl)carbamoyl]-2-methoxyphenyl]-3-pyrazolylcarbonylamino}-2-adamantanecarboxylic acid hydrochloride.

(I: $R_1$=4-$CONMe(CH_2)_2NEt_2$; $R_2$=2-$OCH_3$; $R_3$=H; $R_4$=$CH_3$; AA(OH)=2-carboxy-2-adamantyl).

1.2 g of the product of Preparation 4.16 in 12 ml of $SOCl_2$ and 12 ml of DCM are left stirring for 24 hours at RT. After evaporation under vacuum followed by 2 azeotropic evaporations with 30 ml of toluene, the acid chloride obtained is redissolved in 10 ml of acetonitrile and added to the solution obtained by refluxing a mixture of 0.43 g of compound B and 1.1 ml of bis(trimethylsilyl)acetamide in 20 ml of acetonitrile for 1 hour 15 minutes. The resulting mixture is left stirring under reflux for 4 hours and evaporated under vacuum, and the residue is stirred in 4 ml of MeOH and 0.5 ml of $H_2O$; the mixture is evaporated under vacuum and the residue is then chromatographed on silica H, eluting with DCM/MeOH/20% $NH_4OH$ (95:5:0.5; 90:10:0.5; 85:15:0.5; v/v/v) mixtures to obtain 0.3 g of expected product, m.p.=170° C. (dec.).

NMR: 0.8:mt:3H; 1:mt:3H; 1.5–3.6:mt:34H; 6.5:d:2H; 6.65:s:1H; 6.95:mt:2H; 7.3:mt:3H.

EXAMPLE 20

2-{5-(2,6-Dimethoxyphenyl)-1-[4-[N-methyl-N-(2-(N',N'-diethylaminoethyl)carbamoyl]-2-chlorophenyl]-3-pyrazolylcarbonylamino}-2-adamantanecarboxylic acid hydrochloride.

(I: $R_1$=4-$CONMe(CH_2)_2NEt_2$; $R_2$=2-Cl; $R_3$=H; $R_4$=$CH_3$; AA(OH)=2-carboxy-2-adamantyl.

1.3 g of the product of Preparation 4.17 in 12 ml of DCM and 12 ml of $SOCl_2$ are left stirring for 24 hours at RT. After evaporation under vacuum followed by 2 azeotropic evaporations with 30 ml of toluene, the acid chloride obtained is redissolved in 10 ml of acetonitrile and added to the solution obtained by refluxing a mixture of 0.46 g of compound B and 1.2 ml of bis(trimethylsilyl)acetamide in 20 ml of acetonitrile for 1 hour 15 minutes. The resulting mixture is left stirring under reflux for 4 hours and then evaporated under vacuum, the residue is triturated in 4 ml of MeOH and 2 ml of water, and the mixture is stirred for 30 minutes at RT and evaporated under vacuum. The residue is chromatographed on silica H, eluting with a DCM/MeOH/20% $NH_4OH$ (80:20:0.5; v/v/v) mixture to obtain 0.3 g of expected product; m.p.=160° C. (dec.).

EXAMPLE 21

2-{5-(2,6-Dimethoxyphenyl)-1-[4-[N-(2-morpholinoethyl)carbamoyl]-2-chlorophenyl]-3-pyrazolylcarbonylamino}-2-adamantanecarboxylic acid hydrochloride.

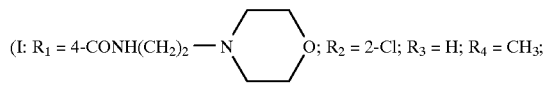

AA(OH)=2-carboxy-2-adamantyl).

A mixture of 1.4 g of the product of Preparation 4.18, 14 ml of $SOCl_2$ and 80 ml of DCM is left stirring for 18 hours at RT. After evaporation under vacuum followed by 2 azeotropic evaporations with 30 ml of toluene and redissolution of the acid chloride formed in 20 ml of acetonitrile, the solution is added to the solution obtained by refluxing a suspension of 0.53 g of compound B in 1.33 ml of bis(trimethylsilyl)acetamide and 30 ml of acetonitrile for 4 hours. After stirring under reflux for 4 hours, the mixture is evaporated under vacuum, the residue is stirred with 10 ml of MeOH and 1 ml of water and the mixture is filtered. After stirring the precipitate for 1 hour with 5 ml of $H_2O$ and 5 drops of concentrated HCl, filtration and washing with 1 ml of $H_2O$, 5 ml of pentane and 5 ml of isopropyl ether, 0.7 g of expected product is obtained, m.p.=200° C.

NMR: 1.5–2.2:u.c.:12; 2.6:bs:2; 2.85:bs:4; 3.3–3.8:mt:20; 6.6:d: 2H; 6.75:s:1H; 7.3:t 1H; 7.45:mt:2H; 7.8:dd:1H; 7.95:d:1H; 8.85:bs:1H.

EXAMPLE 22

2-[5-(2,6-Dimethoxyphenyl)-1-(3-chloro-4-cyanophenyl)-3-pyrazolylcarbonylamino]-2-adamantanecarboxylic acid.

(I: $R_1$=4-CN; $R_2$=3-Cl; $R_3$=H; $R_4$=$CH_3$; AA(OH)=2-carboxy-2-adamantyl).

A mixture containing 0.36 g of the compound obtained in Preparation 4.19, 0.145 ml of isobutyl chloroformate and 0.145 ml of triethylamine in 5 ml of DCM is left stirring at RT for 3 days. Separately, a mixture containing 0.23 g of compound B and 0.34 ml of bis(trifluoromethyl)acetamide in 2 ml of acetonitrile is brought to reflux for 1 hour. The 2 solutions thus prepared are mixed and the resulting mixture is left stirring at RT for 48 hours. After filtration and washing with methanol, the solvents are evaporated of off and the residue is then chromatographed on silica, eluting with a DCM/MeOH/AcOH (100:1:0.5; v/v/v) mixture to obtain 120 mg of the expected product, m.p.=292° C.

EXAMPLE 23

2-[5-(2,6-Dimethoxyphenyl)-1-(4-carbamoyl-3-chlorophenyl)-3-pyrazolylcarbonylamino]-2-adamantanecarboxylic acid.

(I: $R_1$=4-$CONH_2$; $R_2$=3-Cl; $R_3$=H; $R_4$=$CH_3$; AA(OH)=2-carboxy-2-adamantyl).

A mixture containing 0.73 g of the compound obtained in Preparation 4.20, 0.263 ml of isobutyl chloroformate and 0.26 ml of triethylamine in 5 ml of DCM is left stirring at RT for 24 hours.

Separately, a mixture containing 0.34 g of compound B and 0.65 ml of bis(trimethylsilyl)acetamide in 2 ml of acetonitrile is brought to reflux for 1 hour. The 2 solutions thus prepared are mixed and the resulting mixture is left stirring at RT for 4 days. After filtration, washing with 1N HCl and then EtOH and drying over $MgSO_4$, the residue is chromatographed on silica H, eluting with a DCM/MeOH/AcOH (100:2:1; v/v/v) mixture, m.p.=293° C.

EXAMPLE 24

2-{1-[4-[N-Methyl-N-(2-(N',N'-diethylamino)ethyl)carbamoyl]-2-cyclopropylphenyl]-5-(2,6-dimethoxyphenyl)-3-pyrazolylcarbonylamino}-2-adamantanecarboxylic acid hydrochloride.

(I: $R_1$=4-CONMe$(CH_2)_2$NEt$_2$; $R_2$=2-cyclopropyl; $R_3$=H; $R_4$=$CH_3$; AA(OH)=2-carboxy-2-adamantyl).

0.5 g of the product of Preparation 4.21 in 5 ml of DCM and 1 ml of $SOCl_2$ is left stirring for 24 hours at RT. After evaporation under vacuum followed by 2 azeotropic distillations with 30 ml of toluene, the acid chloride formed is redissolved in 5 ml of acetonitrile and added to the solution obtained by refluxing a suspension of 0.19 g of compound B in 0.5 ml of bis(trimethylsilyl)acetamide and 8.5 ml of acetonitrile for two and a half hours, and the mixture is stirred for 12 hours at RT. It is evaporated under vacuum, the residue is stirred for 45 minutes with 5 3.5 ml of MeOH and 1 ml of $H_2O$, 2.5 ml of $H_2O$ are then added dropwise and the mixture is filtered. After evaporation of the filtrate under vacuum and drying under vacuum for 24 hours at 60° C., 0.14 g of expected product are obtained, m.p.=135° C. (dec.).

NMR (DMSO+TFA): 0.6:u.c.:2H; 0.9:u.c.:2H; 1.2:u.c.:6H; 1.5–2.2:u.c.:12H; 2.6:u.c.:2H; 2.9:bs:3H; 3.2:u.c.:6H; 3.6:s:6H; 3.7u.c.:2H; 6.6:d:2H; 6.75:s:1H; 6.85:s:1H; 7.1–7.4:u.c.:3H.

EXAMPLE 25

2-{1-[3-[N-Methyl-N-(2-(N',N'-dimethylamino)ethyl)carbamoyl]-4-chlorophenyl]-5-(2,6-dimethoxyphenyl)-3-pyrazolylcarbonylamino}-2-adamantanecarboxylic acid hydrochloride.

(I: $R_1$=3-CONMe$(CH_2)_2$NMe$_2$; $R_2$=4-Cl; $R_3$=H; $R_4$=$CH_3$; AA(OH)=2-carboxy-2-adamantyl).

A solution of 0.43 g of the product of Preparation 4.22 in 10 ml of DCM and 6 ml of $SOCl_2$ is left stirring for 15 hours at RT. After evaporation under vacuum followed by 2 azeotropic distillations with 30 ml of toluene, the acid chloride is redissolved in 3 ml of acetonitrile, and the solution is added to the solution obtained by refluxing a suspension of 0.17 g of compound B in 0.5 ml of bis(trimethylsilyl)acetamide and 10 ml of acetonitrile for 3 hours. The mixture is stirred under reflux for 3 hours and then for 15 hours at RT. It is evaporated under vacuum, and the residue is stirred for 1 hour with 12 ml of MeOH and 6 ml of water. The MeOH is evaporated off under vacuum, the residue is extracted twice with 50 ml of DCM and the organic phase is dried over $Na_2SO_4$ and evaporated under vacuum to obtain 0.16 g of expected product, m.p.=206° C. (dec.).

NMR: 1.5–2.3:u.c.:12H; 2.6–3.8:u.c.: 21H; 6.7:d:2H; 6.8:s:1H; 7.1–7.7:u.c.:4H.

EXAMPLE 26

2-{1-[5-[N-Methyl-N-(3-(N',N'-dimethylamino)propyl)carbamoyl]-2-methylphenyl]-5-(2,6-dimethoxyphenyl)-3-pyrazolylcarbonylamino}-2-adamantanecarboxylic acid.

(I: $R_1$=5-CONMe$(CH_2)_3$NMe$_2$; $R_2$=2-CH$_3$; $R_3$=H; $R_4$=CH$_3$; AA(OH)=2-carboxy-2-adamantyl).

A solution of 1.7 g of the product of Preparation 4.23 in 15 ml of SOCl$_2$ is left stirring for five and a half hours at RT. After evaporation under vacuum followed by 3 azeotropic distillations with 30 ml of DCM, the acid chloride formed is redissolved in 30 ml of acetonitrile, and the solution is added to the solution obtained by refluxing a suspension of 0.69 g of compound B in 1.75 ml of bis(trimethylsilyl)acetamide and 6 ml of acetonitrile for 1 hour. After stirring for 15 hours at RT and evaporation under vacuum, the residue is dissolved in 13 ml of MeOH, 12 ml of water are added slowly and the mixture is stirred for 30 minutes at RT. After evaporation under vacuum, trituration of the residue in 5 ml of 1N HCl, decantation, 3 extractions of the residual gum with 100 ml of DCM and drying over MgSO$_4$, the organic phase is evaporated and the residue is then dissolved in 15 ml of water. The mixture is alkalinized with 30% NaOH to pH 8 and crystallization is then induced ultrasonically. After filtration, the residue is recrystallized in toluene and dried under vacuum at 60° C. to obtain 1.32 g of expected product, m.p.=165° C.

NMR (DMSO+TFA): 1.6–2.2:u.c.:14H; 2.2:s:3H; 2.5–3.2:u.c.:13H; 3.5:mt 2H; 3.7:s:6H; 6.65:d:2H; 6.8:s:1H; 7.3–7.6:u.c.:3H.

From the acids II described in Table 5 or in the Preparations, by following the procedures indicated above, the compounds according to the invention collated in Table 7 below are prepared.

TABLE 7

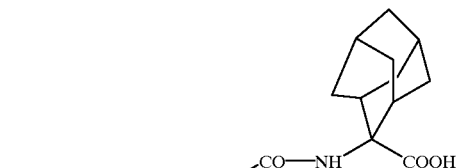

(I)

| EXAMPLE (from) | $R_1$ | $R_2$ | $R_3$ | M.p. ° C. or NMR |
|---|---|---|---|---|
| 27 (4.24) | 4-CONMe(CH$_2$)$_2$NMe$_2$ | 2-OCH$_3$ | H | 195 (dec.) |

TABLE 7-continued

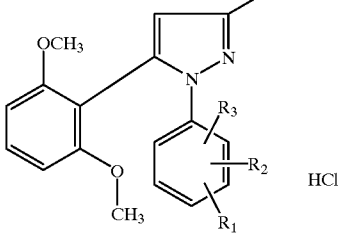

(I)

| EXAMPLE (from) | $R_1$ | $R_2$ | $R_3$ | M.p. ° C. or NMR |
|---|---|---|---|---|
| 28 (4.25) | 4-CO—N(piperazine)N—CH$_3$ | 2-OCH$_3$ | H | 220 (dec.) NMR |
| 29 (4.26) | 4-SO$_2$NMe(CH$_2$)$_3$NMe$_2$ | 2-CH$_3$ | 3-CH$_3$ | 266 (dec.) NMR |
| 30 (4.27) | 5-CONMe(CH$_2$)$_2$NMe$_2$ | 2-Cl | H | 198 (dec.) NMR |
| 31 (4.28) | 4-CONMe(CH$_2$)$_2$NEt$_2$ | 2-CF$_3$ | H | 180 (dec.) NMR |
| 32 (4.29) | 5-CONMe(CH$_2$)$_2$NMe$_2$ | 2-OCH$_3$ | H | 208 NMR |
| 33 (4.31) (a) | 4-CONH(CH$_2$)$_3$N(nBu)$_2$ | 2-iPr | H | 165 |
| 34 (4.40) (a) | 4-CONEt(CH$_2$)$_2$NEt$_2$ | 2-iPr | H | 230 NMR |
| 35 (4.33) | 4-CONH—C(cyclopentyl)—CH$_2$NMe$_2$ | 2-iPr | H | 253 (dec.) |
| 36 (4.39) | 4-SO$_2$N(CH$_2$)NMe$_2$ / Bz | 2-iPr | H | 167 |

(a) unsalified compound.

NMR:

EXAMPLE 28

1.3–3.7:mt:26H; 6.55:d 2H; 6.65:S:1H; 6.9:mt:3H, 7.15–7.5:mt:4H.

EXAMPLE 29

1.5–2.3:u.c.:17H; 2.55:s:2H; 2.8:s:9H; 2.95–3.3:u.c.:4H; 3.6:s:6H; 6.6:d:2H; 6.7:s:1H; 7–7.7:u.c.:3H.

EXAMPLE 30

1.4–2.3:u.c.:12H; 2.6:bs:2H; 2.7:bs:3H; 2.8:bs:6H; 3.4:u.c.:2H; 3.6:s:6H; 3.8:u.c.:2H; 6.6:d:2H; 6.82:s:1H; 7.2–7.8:u.c.:5H; 13.0:bs:1H.

EXAMPLE 31

(DMSO +TFA): 1.2:t:6H; 1.5–2.2:u.c.:12H; 2.5:bs:2H; 2.9:s:3H; 3.1–3.5::u.c.:9H; 3.6:s:6H; 3.8:u.c.:2H; 6.6:d:2H; 6.8:s:1H; 7.3:u.c.:3H; 7.7:d:1H; 8:s:1H.

EXAMPLE 32

1.6–2.2:u.c.:12H; 2.45s:6H; 2.60:bs:2H; 2.85:s:3H; 3.40:u.c.:2H; 3.56:s:3H; 3.60:s:6H; 3.70:u.c.:2H; 6.60:d:2H; 6.78:s:1H; 7.00:t:1H; 7.20:u.c.:3H; 7.40:bs:1H.

EXAMPLE 34

(DMSO+TFA): 0.9–1.3:u.c.:15H; 1.6–2.2:u.c.:8H; 2.7:u.c.:1H; 3.1–3.4:u.c.:8H; 3.6–3.8:u.c.:8H; 6.55:d:2H; 6.75:s:1H; 7.1–7.4:u.c.:4H.

EXAMPLE 37

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid hydrogen sulphate.

0.5 g of the compound obtained in EXAMPLE 1' is added to a solution of 0.08 g of $H_2SO_4$ in 5 ml of MeOH, this solution is poured into 150 ml of ether cooled to 5° C., and the precipitate formed is drained. 0.54 g of the expected product is obtained. After recrystallization in water, m.p.=212° C. (dec.). After recrystallization in 2-isopropanol, m.p.=263° C.

NMR (DMSO+TFA): 1.1:d:6H; 1.5–2.2:u.c.:14H; 2.5:bs:2H; 2.6–3:u.c.:10H; 3.1:mt:2H; 3.5:mt:2H; 3.65:s:6H; 6.6:d:2H; 6.75: s:1H; 7.1–7.5:u.c.:4H.

The product of EXAMPLE 37 may also be prepared according to the procedure below:

22 ml of concentrated $H_2SO_4$ are added slowly and with stirring to a suspension of 3.4 g of internal salt of EXAMPLE 1' in 34 ml of water, and the mixture is heated to 40° until a change is obtained in the appearance of the suspension. The latter is allowed to cool to RT for 4 hours with stirring, and the product is filtered off and dried to obtain 3.8 g of expected hydrogen sulphate.

EXAMPLE 38

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid benzenesulphonate.

A mixture of 0.5 g of the compound obtained in EXAMPLE 1' and 0.16 g of benzenesulphonic acid in 5 ml of MeOH is poured into 75 ml of ether cooled to 5° C., and the precipitate formed is drained. 0.06 g of the expected product is obtained, m.p.=170° C. (dec.).

NMR (DMSO+TFA): 1:d:6H; 1.4–2.2:u.c.:14H; 2.45:bs:2H; 2.5–3.2:u.c.:12H; 3.4:mt:2H; 3.55:s:6H; 6.5:d:2H; 6.65:s:1H; 7–7.4::u.c.:7H; 7.5:mt:2H.

EXAMPLE 39

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid citrate.

0.084 g of citric acid is added at RT to a solution of 0.3 g of the compound obtained in EXAMPLE 1' in 5 ml of EtOH and 3 ml of DCM, and the mixture is left stirring for 2 hours at RT. It is concentrated under vacuum and the residue is recrystallized in 2-propanol. 0.26 g of the expected product is obtained, m.p.=168° C.

NMR (DMSO+TFA): 1.05:d:6H; 1.5–2.3:u.c.:14H; 2.5:bs:2H; 2.6–3.3:u.c.:16H; 3.3– 3.8:s+u.c.:8H; 6.6:d:2H; 6.75:S:1H; 7.1–7.5:u.c.:4H.

EXAMPLE 40

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid maleate.

0.1 g of the compound obtained in EXAMPLE 1' and 0.017 g of maleic acid are dissolved in the heated state in 2.3 ml of 2-propanol, and the mixture is concentrated under vacuum. The residue is dissolved in 0.3 ml of EtOH, this solution is poured into 30 ml of ether and the precipitate formed is drained. 0.04 g of the expected product is obtained, m.p.=260° C. (dec.).

NMR (DMSO+TFA): 1.05:d:6H; 1.55–2.2:u.c.:14H; 2.5:bs:2H; 2.6–3:u.c.:10H; 3.5:mt:2H; 3.65:s:6H; 6.3:s:2H; 6.6:d:2H; 6.75:s:1H; 7.15–7.45:u.c.:4H.

EXAMPLE 41

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid (S)-(+)-arginine salt.

0.1 g of the compound obtained in EXAMPLE 1' and 0.03 g of (S)-(+)-arginine are dissolved in the heated state in 4 ml of MeOH, and this solution is concentrated to 1 ml and poured into 10 ml of ether cooled to 5° C. 0.055 g of the expected product is obtained after draining and drying over $P_2O_5$, m.p.=176° C. (dec.).

NMR (DMSO+TFA): 1.05:d:6H; 1.5–2.2:u.c.:20H; 2.55:bs:2H; 2.6–3.55:u.c.:16H; 3.65:s:6H; 3.95:t:1H; 6.6:d:2H; 6.75:s:1H; 7.15–7.4:u.c. 4H.

EXAMPLE 42

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid edisylate.

A) 1,2-Ethanedisulphonic acid.

A solution of 3 g of 1,2-ethanedisulphonic acid disodium salt in 10 ml of water is introduced slowly into 200 ml of Dowex® 50×X 8 resin, and the product is eluted with 200 ml of demineralized water. The eluate is diluted by adding EtOH and concentrated under vacuum. 3.35 g of the expected product are obtained in the form of an oil which crystallizes at RT.

B) 2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid edisylate.

0.05 g of the compound obtained in EXAMPLE 1' and 0.04 g of the compound obtained in step A are dissolved in the heated state in 2 ml of 2-propanol, and the mixture is concentrated under vacuum. The residue is dissolved in 0.3 ml of water and 8 drops of dioxane, and crystallization is allowed to take place at RT. The crystallized product formed is drained, washed with water and dried at 90° C. under vacuum. 0.042 g of expected product is obtained, m.p.=266° C. (dec.).

NMR (DMSO+TFA): 1.05:d:6H; 1.5–2.2:u.c.:14H; 2.5:bs:2H; 2.6–3:u.c.+s:14H; 3.1:mt:2H; 3.5:mt:2H; 3.65:s:6H; 6.6:d:2H; 6.75:s:1H; 7.15–7.45:u.c.:4H.

EXAMPLE 43

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid sodium salt.

0.206 g of the compound obtained in EXAMPLE 1' and 0.026 g of sodium methylate are dissolved in 1 ml of MeOH and a few drops of DCM, and this solution is then poured into 50 ml of ether cooled to 5° C. The gelatinous precipitate formed is drained and dried over $P_2O_5$ and under vacuum. 0.15 g of the expected product is obtained, m.p.=191° C.

This compound may also be obtained by following the procedure described below.

0.7 ml of a solution of 0.104 g of NaOH in 10 ml of MeOH is added to a solution of 0.1 g of the compound obtained in EXAMPLE 1' in 5 ml of MeOH and 4 ml of DCM, and the mixture is concentrated under vacuum. The residue is dissolved in 1 ml of 2-propanol, this solution is poured into 75 ml of ether cooled to 5° C. and the precipitate formed is drained. 0.005 g of the expected product is obtained.

NMR: 1:d:6H; 1.4–2.3:u.c.:20H; 2.55:bs:2H; 2.6:mt:1H; 2.85:d:3H; 3.1 and 3.4: 2mt:4H; 3.6:s:6H; 6.55:s:1H; 6.6:s:2H; 6.95:s:1H; 7–7.35:u.c.:4H.

The NMR spectrum recorded in the presence of DMSO+TFA is slightly different.

NMR (DMSO+TFA): 1.05:d:6H; 1.5–2.3:u.c.:14H; 2.5:bs:2H; 2.6–3:u.c.:10H; 3.1:mt:2H; 3.5:mt:6H; 6.6:d:2H; 6.75:s:1H; 7.1–7.4:u.c.:4H.

EXAMPLE 44

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid fumarate.

0.1 g of the compound obtained in EXAMPLE 1' and 0.017 g of fumaric acid are dissolved in 1.5 ml of EtOH, 1.5 ml of DCM and 4 ml of MeOH, and the mixture is left stirring for 10 minutes at RT. It is partially concentrated under vacuum and crystallization is allowed to take place. 0.025 g of the expected product is obtained after draining and washing with EtOH, m.p.=243° C.

NMR (DMSO+TFA): 1:d:6H; 1.5–2.3:u.c.:14H; 2.5:bs:2H; 2.6–3:u.c.:10H; 3.1:mt:2H; 3.4:mt:2H; 3.6:s:6H; 6.5–6.7:d+s:3H; 6.75:s:1H; 7.1–7.4:u.c.:5H.

EXAMPLE 45

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid N-methyl-D-glucamine salt.

A solution of 0.07 g of the compound obtained in EXAMPLE 1' in 5 ml of EtOH and 1 ml of DCM is heated to reflux, 0.02 g of N-methyl-D-glucamine is added and the mixture is left stirring for 1 hour 30 minutes at RT. It is partially concentrated under vacuum and poured into 15 ml of ether, and the precipitate formed is drained. 0.032 g of the expected product is obtained, m.p.=90° C. (gum).

NMR (DMSO+TFA): 1:d:6H; 1.5–2.2:u.c.:14H; 2.5–2.6:mt:5H; 2.6–3.2:u.c.:14H; 3.2–3.7:u.c.:13H; 3.85:mt:1H; 6.6:d:2H; 6.7:s:1H; 7.1–7.4:u.c.:4H.

EXAMPLE 46

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid diethanolamine salt.

0.1 g of the compound obtained in EXAMPLE 1' is dissolved in 1.5 ml of EtOH and 1.5 ml of DCM, 0.015 g of diethanolamine is added and the mixture is left stirring for 30 minutes at RT and left overnight at 5° C. The crystallized product formed is drained. 0.03 g of the expected product is obtained, m.p.=200° C. (dec.).

NMR (DMSO+TFA): 1.05:d:6H; 1.5–2.2:u.c.:14H; 2.5:bs:2H; 2.6–3.25:u.c.:16H; 3.3–3.8:u.c.+s:12H; 6.6:d:2H; 6.7:s:1H; 7.1–7.4::u.c.:4H.

EXAMPLE 47

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid L(+)-tartrate.

A mixture of 0.1 g of the compound obtained in EXAMPLE 1' and 0.022 g of L(+)-tartaric acid in 1.5 ml of EtOH and 1.5 ml of DCM is heated to reflux, 8 ml of EtOH are then added and refluxing is continued for 5 minutes. After cooling to RT, the mixture is partially concentrated under vacuum and poured into 10 ml of ether, and the precipitate formed is drained. 0.07 g of the expected product is obtained after drying over $P_2O_5$, m.p.=154° C. (dec.).

NMR (DMSO+TFA): 1.05:d:6H; 1.5–2.4:u.c.:14H; 2.55:bs:2H; 2.6–3:u.c.:10H; 3.1mt 2H; 3.5:mt:2H; 3.65:s:6H; 4.35 s:2H; :6.6:d:2H; 6.75:s:1H; 7.15–7.5:u.c.:4H.

EXAMPLE 48

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid choline salt.

A solution of 1 ml of DCM containing 0.05 g of the compound obtained in EXAMPLE 1' and 0.025 ml of a 45% solution of choline hydroxide in MeOH are left stirring for 15 minutes at 35° C., and the mixture is then concentrated under vacuum. The residue is triturated in 5 ml of ether and the precipitate formed is drained. 0.03 g of the expected product is obtained, m.p.=150° C.

NMR (DMSO+TFA): 1.05:d:6H; 1.4–2.2:u.c.:14H; 2.5:bs:2H; 2.4–3:u.c.:10H; 3.1:bs:11H; 3.4:mt:2H; 3.5:mt:2H; 3.6:s:6H; 3.8:mt:2H; 6.6:d:2H; 6.7:1H; 7.1–7.4:u.c.:4H.

EXAMPLE 49

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid isethionate.

A mixture of 0.1 g of the compound obtained in EXAMPLE 1' in 3 ml of 2-propanol is heated to reflux, 0.022 g of 83% isethionic acid (obtained by elution of sodium isethionate on DOWEX® 50W×8 resin in $H^+$ form) is added and crystallization is allowed to take place overnight. The crystallized product formed is drained. 0.055 g of the expected product is obtained, m.p.=230° C.

NMR (DMSO+TFA): 1.05:d:6H; 1.55:u.c.:14H; 2.55:bs:2H; 2.6–3.05:u.c.:12H; 3.1:mt:2H; 3.5:mt:2H; 3.6–3.7:s+mt:8H; 6.6:d:2H; 6.75:s:1H; 7.15–7.45:u.c.:4H.

EXAMPLE 50

2-[5-(2,6-Dimethoxyphenyl)-1-[4-[N-methyl-N-(3-dimethylaminopropyl)carbamoyl]-2-isopropylphenyl]-3- pyrazolylcarbonylamino]-2-adamantanecarboxylic acid potassium salt.

A solution of 0.15 g of the compound obtained in EXAMPLE 1' and 0.03 g of potassium tert-butylate in 6.5 ml of 2-propanol is left overnight at RT and then concentrated under vacuum. The residue is dissolved in 0.5 ml of MeOH, and this solution is poured into 25 ml of isopropyl ether cooled to −20° C. The precipitate formed is drained and dried over $P_2O_5$ at 80° C. 0.09 g of the expected product is obtained, m.p.=222° C.

This compound may also be obtained by following the procedure described below.

1 ml of a solution of 0.129 g of KOH in 10 ml of MeOH is added to a solution of 0.1 g of the compound obtained in EXAMPLE 1' in 4 ml of DCM, and the mixture is then concentrated under vacuum. The residue is dissolved in 0.5 ml of 2-propanol, this solution is poured into 75 ml of ether cooled to 5° C. and the precipitate formed is drained. 0.015 g of the expected product is obtained.

NMR (DMSO+TFA): 1.05:d:6H; 1.5–2.3:u.c.:14H; 2.5:bs:2H; 2.6–3:u.c.:10H; 3.1:t2H; 3.5:t:2H; 3.6:s:6H; 6.6:d:2H; 6.7:s:1H; 7.1–7.5:u.c.:4H.

EXAMPLE 51

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid dihydrogen phosphate.

A mixture of 0.1 g of the compound obtained in EXAMPLE 1' and 0.017 g of 85% orthophosphoric acid in 2 ml of DCM and 3 ml of EtOH is left stirring for 1 hour at RT. It is partially concentrated under vacuum and poured into 10 ml of ether cooled to 5° C., and the precipitate formed is drained. 0.04 g of the expected product is obtained after drying at 60° C.

NMR (DMSO+TFA): 1.05:d:6H; 1.5–2.2:m:14H; 2.5:se:2H; 2.6–3.3:u.c.:12H; 3.5:mt:2H; 3.6:s:6H; 6.6:d:2H; 6.7:s:1H; 7.1–7.4:u.c.:4H.

EXAMPLE 52

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid 2-naphthalenesulphonate.

A solution of 0.5 g of the compound obtained in EXAMPLE 1' and 0.16 g of 2-naphthalenesulphonic acid in 5 ml of MeOH is precipitated with 25 ml of ether cooled to 5° C., the precipitate formed is drained and the filtrate is kept. The precipitate is dissolved in 2 ml of MeOH, this solution is poured into 50 ml of ether cooled to 5° C., the precipitate formed is drained and 0.2 g of the expected product is obtained. The first filtrate is precipitated with 50 ml of ether cooled to 5° C., the precipitate formed is drained and 0.27 g of second crop of the expected product is obtained.

NMR (DMSO+TFA): 1.05:d:6H; 1.5–2.2:u.c.:14H; 2.5:bs:2H; 2.6–3:u.c.:10H; 3.1:mt:2H; 3.5:mt:2H; 3.65:s:6H; 6.6:d:2H; 6.7:s:1H; 7.1–7.6:u.c.:7H; 7.7:d:1H; 7.8–8.1:u.c.:2H; 8.2:s:1H.

EXAMPLE 53

2-[5-(2,6-Dimethoxyphenyl)-1-[4-[N-(2-diisopropylaminoethyl)carbamoyl]-2-isopropylphenyl]-3-pyrazolylcarbonylamino]-2-adamantanecarboxylic acid.

(I: $R_1$=4-CONH(CH$_2$)$_2$N(iPr)$_2$; $R_2$=2-iPr; $R_3$H; $R_4$=CH$_3$; AA(OH)=2-carboxy-2-adamantyl).

A mixture of 0.53 g of the compound obtained in reparation 4.30 and 2 ml of SOCl$_2$ is left stirring for 4 hours at RT. It is concentrated under vacuum, the residue is taken up with DCM and the mixture is evaporated under vacuum, the residue is taken up with DCM and the solvent is evaporated off under vacuum. The acid chloride thereby obtained is used without further treatment. Separately, a mixture of 0.19 g of compound B and 0.49 ml of bis(trimethylsilyl) acetamide in 2 ml of acetonitrile is heated to reflux under a nitrogen atmosphere for 35 minutes. After cooling to RT, a solution of the acid chloride prepared above in 8 ml of acetonitrile is added, and the mixture is left stirring overnight at RT. It is evaporated under vacuum, the residue is stirred with 8.8 ml of MeOH, 8.8 ml of water are added and the mixture is evaporated under vacuum. The residue is treated with 1.2N HCl solution and the precipitate formed is filtered off. The precipitate is treated with 10 ml of water, the mixture is alkalinized to pH 8 by adding 1.3N NaOH solution, and the precipitate is drained and washed with water. 0.475 g of the expected product is obtained after crystallization in the heated state in 40 ml of acetonitrile, m.p.=196–198° C.

NMR (DMSO+TFA): 1.1:d:6H; 1.3:d:12H; 1.6–2.2:u.c.:12H; 2.55:u.c.:2H; 2.7:mt:1H; 3.2:u.c.:2H; 3.5–3.8:u.c.+s:10H; 6.6:d:2H; 6.75:s:1H; 7.2–7.4:mt:2H; 7.65:d:1H; 7.85:s:1H.

EXAMPLE 54

2-[5-(2,6-Dimethoxyphenyl)-1-[4-[N,N-bis(2-diethylaminoethyl)carbamoyl]-2-isopropylphenyl]-3-pyrazolylcarbonylamino]-2-adamantanecarboxylic acid.

(I: $R_1$=4-CON(CH$_2$CH$_2$NEt$_2$)$_2$; $R_2$=2-iPr; $R_3$=H; $R_4$=CH$_3$; AA(OH)=2-carboxy-2-adamantyl).

A mixture of 0.4 g of the compound obtained in Preparation 4.34 and 2.5 ml of SOCl$_2$ is left stirring for 24 hours at RT. It is concentrated under vacuum, the residue is taken up with toluene and the solvent is evaporated off under vacuum. The acid chloride thereby obtained is used without further treatment. Separately, a mixture of 0.18 g of compound B and 0.5 ml of bis(trimethylsilyl)acetamide in 4 ml of acetonitrile is heated to reflux for 45 minutes.

After cooling to RT, a solution of the acid chloride prepared above in 3 ml of acetonitrile is added, and the mixture is left stirring for 72 hours at RT. 3 ml of MeOH are added and the reaction mixture is concentrated under vacuum. The residue is dissolved in 3 ml of 1.2N HCl, the solution is washed 3 times with AcOEt, the aqueous phase is neutralized to pH 6 by 10 adding concentrated NaOH solution, and the gummy product formed is separated after settling has taken place. The gummy product is chromatographed on silica H, eluting with a DCM/MeOH/NH$_4$OH (75:25:1.2; v/v/v) mixture. 0.4 g of the expected product is obtained is after trituration in ether, m.p.=169° C.

EXAMPLE 55

2-[5-(2,6-Dimethoxyphenyl)-1-[4-[N-(4-piperidyl)carbamoyl]-2-isopropylphenyl]-3-pyrazolylcarbonylamino]l-2-adamantanecarboxylic acid hydrochloride.

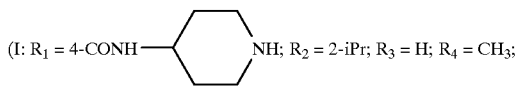

AA(OH)=2-carboxy-2-adamantyl).

A mixture of 0.3 g of the compound obtained in EXAMPLE 12, 0.05 g of palladium on charcoal (10% Pd) and 0.033 ml of concentrated HCl in 10 ml of MeOH and 4 ml of DMF is hydrogenated for 5 days at RT and then for 4 days at 50° C., at atmospheric pressure. The catalyst is filtered off on Celite® and the filtrate is evaporated under vacuum. The residue is taken up with ether and the crystallized product formed is drained. 0.121 g of the expected product is obtained after drying over $P_2O_5$ at 70° C. under vacuum, m.p.=252° C.

NMR (DMSO+TFA): 1.1:d:6H; 1.5–2.2:u.c.:16H; 2.4–3.5:3mt+bs:7H; 3.6:s:6H; 3.9–4.15:u.c.:1H; 6.6:d:2H; 6.7:s:1H; 7.1–7.4:mt:2H; 7.6:d:1H; 7.8:s:1H.

EXAMPLE 56

2-[5-(2,6-Dimethoxyphenyl)-1-[4-[N-(1-ethyl-2-pyrrolidinylmethyl)carbamoyl]-2-isopropylphenyl]-3-pyrazolylcarbonylamino]-2-adamantanecarboxylic acid.

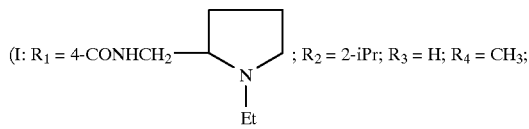

AA(OH)=2-carboxy-2-adamantyl).

This compound is prepared according to the procedure described in EXAMPLE 53, from 0.48 g of the compound obtained in Preparation 4.35 and 2 ml of $SOCl_2$, followed by 0.18 g of compound B and 0.46 ml of bis(trimethylsilyl) acetamide in 2 ml of acetonitrile. 0.2 g of the expected product is obtained after recrystallization in 2-propanol, m.p.=212° C. (dec.).

NMR (DMSO+TFA): 0.9:bs:6H; 1.05:u.c.:3H; 1.3–2.1:u.c.:14H; 2.3:bs:2H; 2.5:u.c.:1H; 2.9:u.c.:2H; 3.2–3.6:u.c.+s:11H; 6.4:d:2H; 6.5:bs:1H; 7–7.3:u.c.:2H; 7.45:d:1H; 7.65:bs:1H.

EXAMPLE 57

2-[5-(2,6-Dimethoxyphenyl)-1-[4-[N-(2,2,6,6-tetramethyl-4-piperidyl)carbamoyl]-2-isopropylphenyl]-3-pyrazolylcarbonylamino]-2-adamantanecarboxylic acid.

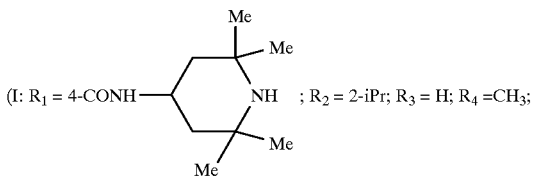

AA(OH)=2-carboxy-2-adamantyl).

This compound is prepared according to the procedure described in EXAMPLE 53, from 0.43 g of the compound obtained in Preparation 4.36 and 2 ml of $SOCl_2$, followed by 0.15 g of compound B and 0.39 ml of bis(trimethylsilyl) acetamide in 2 ml of acetonitrile. After stirring of the reaction mixture overnight at RT, the precipitate formed is drained and washed with acetonitrile. The precipitate is taken up in 4 ml of MeOH, 4 ml of water are added gradually and the mixture is concentrated under vacuum. The residue is taken up with 1.2N HCl solution and the precipitate is drained after trituration. The precipitate is taken up in 3 ml of water, the mixture is alkalinized to pH 9 by adding 1.3N NaOH solution, and the precipitate formed is drained and washed with water. 0.24 g of the expected product is obtained after drying over $P_2O_5$, m.p.=270–272° C.

NMR (DMSO+TFA): 1.5:d:6H; 1.3:s:6H; 1.4:s:6H; 1.5–2.2:2:u.c.:16H; 2.65:mt:1H; 3.6:s:6H; 4.2–4.4:u.c.:1H; 6.55:d:2H; 6.7:s:1H; 7.1–7.4:u.c.:2H; 7.6:d:1H; 7.8:s:1H.

EXAMPLE 58

2-[5-(2,6-Dimethoxyphenyl)-1-[4-[[3-(diethylamino)-1-pyrrolidinyl]carbonyl]-2-isopropylphenyl]-3-pyrazolylcarbonylamino]-2-adamantanecarboxylic acid.

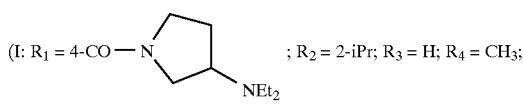

AA(OH)=2-carboxy-2-adamantyl).

This compound is prepared according to the procedure described in EXAMPLE 53, from 0.39 g of the compound obtained in Preparation 4.41 and 2 ml of $SOCl_2$, followed by 0.13 g of compound B and 0.34 ml of bis(trimethylsilyl) acetamide in 2 ml of acetonitrile. After stirring of the reaction mixture overnight at RT, some insoluble matter is filtered off and the filtrate is concentrated under vacuum. The residue is taken up in 5 ml of MeOH, 5 ml of water are added and the mixture is concentrated under vacuum. The residue is taken up with 1.2N HCl solution and the crystals formed are drained. The crystals are dissolved in water, the solution is alkalinized to pH 9 by adding 1.3N NaOH and the precipitate formed is drained. 0.07 g of the expected product is obtained after recrystallization in acetonitrile, m.p.=175° C. (dec.).

NMR (DMSO+TFA): 1.0:d:6H; 1.1–1.3:u.c.:6H; 1.5–2.8:4:u.c.:17H; 2.8–4.2:3:u.c.+1s:15H; 6.6:d:2H; 6.7:s:1H; 7.2–7.4:u.c.:3H; 7.5:bs:1H.

EXAMPLE 59

2-[5-(2,6-Dimethoxyphenyl)-1-[4-[[4-(dimethylamino)-1-piperidyl]carbonyl]-2-isopropylphenyl]-3-pyrazolylcarbonylamino]-2-adamantanecarboxylic acid.

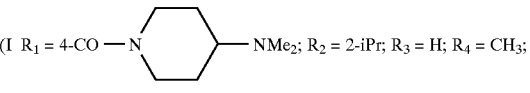

AA(OH)=2-carboxy-2-adamantyl).

This compound is prepared according to the procedure described in EXAMPLE 53, from 0.45 g of the compound obtained in Preparation 4.37 and 2 ml of $SOCl_2$, followed by 0.17 g of compound B and 0.43 ml of bis(trimethylsilyl) acetamide in 2 ml of acetonitrile. 0.26 g of the expected product is obtained after crystallization in the heated state in acetone and then in MeOH, m.p.=200° C. (dec.).

NMR (DMSO+TFA): 1.05:d:6H; 1.4–2.3:2:u.c.:16H; 2.5:bs:2H; 2.7:s+mt:7H; 2.8–3.8:2:u.c.+s:10H; 4.4–4.8:u.c.:1H; 6.6:d:2H; 6.7:s:1H; 7.1–7.4:u.c.:4H.

EXAMPLE 60

2-[5-(2,6-Dimethoxyphenyl)-1-[4-[N-methyl-N-(2-cyanoethyl)carbamoyl]-2-isopropylphenyl]-3-pyrazolylcarbonylamino]-2-adamantanecarboxylic acid.

(I: $R_1$=4-CONMe(CH$_2$)$_2$CN; $R_2$=2-iPr; $R_3$=H; $R_4$=CH$_3$; AA(OH)=2-carboxy-2-adamantyl).

This compound is prepared according to the procedure described in EXAMPLE 53, from 3.48 g of the compound obtained in Preparation 4.38 and 20 ml of SOCl$_2$ followed by 1.43 g of compound B and 3.6 ml of bis(trimethylsilyl) acetamide in 25 ml of acetonitrile. After stirring of the reaction mixture overnight at RT, the mixture is concentrated under vacuum, the residue is taken up in 64 ml of MeOH, 64 ml of water are added and the mixture is concentrated under vacuum. The residue is taken up in 1.2N HCl, and the precipitate formed is drained and washed with 1.2N HCl. The precipitate is taken up in 5 ml of MeOH, the mixture is heated to reflux and allowed to cool to RT and the precipitate is drained. 3.78 g of the expected product are obtained after drying over P$_2$O$_5$, m.p.=249° C.

NMR (DMSO+TFA): 1.05:d:6H; 1.5–2.2:u.c.:12H; 2.42–3.0:u.c.:8H; 3.3–3.75:u.c.:8H; 6.58:d:2H; 6.73:s:1H; 7.1–7.42:u.c.:4H.

EXAMPLE 61

2-[5-(2,6-Dimethoxyphenyl)-1-[4-[N-methyl-N-(3-aminopropyl)carbamoyl]-2-isopropylphenyl]-3-pyrazolylcarbonylamino]-2-adamantanecarboxylic acid.

(I: $R_1$=4-CONMe(CH$_2$)$_3$NH$_2$; $R_2$=2-iPr; $R_3$H; $R_4$=CH$_3$; AA(OH)=2-carboxy-2-adamantyl).

A mixture of 1 g of the compound obtained in EXAMPLE 60, 10 ml of 20% ammonium hydroxide solution and 0.1 g of Raney® nickel in 20 ml of EtOH is hydrogenated for 4 hours at RT and at atmospheric pressure. The catalyst is filtered off on Celite® and washed with EtOH and then with MeOH, and the filtrate is partially concentrated. The crystallized product formed is drained and the filtrate is concentrated under vacuum. The crystallized product and the concentration residue are taken up in 1.2N HCl, and the precipitate is drained and washed with 1.2N HCl. The precipitate is dissolved in water, the aqueous phase is neutralized to pH 7 by adding 1.3N NaOH, and the precipitate formed is drained, washed with water and dried over P$_2$O$_5$. The precipitate is taken up in 2-propanol, the mixture is heated to reflux and allowed to cool to RT and the precipitate is drained. 0.54 g of the expected product is obtained after drying, m.p.=239–241 ° C.

NMR (DMSO+TFA): 1.05:d:6H; 1.5–2.2:u.c.:14H; 2.4–3.8:u.c.:8H; 3.5:mt:2H; 3.64:s:6H; 6.6:d:2H; 6.72:s:1H; 7.1–7.45:u.c.:4H.

EXAMPLE 62

2-[5-(2,6-Dimethoxyphenyl)-1-[4-[N-methyl-N-(2-carbamoylethyl)carbamoyl]-2-isopropylphenyl]-3-pyrazolylcarbonylamino]-2-adamantanecarboxylic acid.

(I: $R_1$=4-CONMe(CH$_2$)$_2$CONH$_2$; $R_2$=2-iPr; $R_3$H; $R_4$=CH$_3$; AA(OH)=2-carboxy-2-adamantyl).

A mixture of 0.2 g of the compound obtained in EXAMPLE 60, 0.12 ml of 30% hydrogen peroxide solution in water and 0.18 ml of 6N NaOH in 10 ml of 95% EtOH is left stirring for 3 hours 30 minutes at RT. 0.06 ml of 30% hydrogen peroxide solution and 0.06 ml of 6N NaOH are then added, and stirring is continued at RT for 1 hour 30 minutes. Some insoluble matter is filtered off, water is added to the filtrate, the aqueous phase is washed twice with DCM, acidified to pH 3 by adding 1.2N HCl and extracted with DCM, the organic phase is dried over MgSO$_4$ and the solvent is evaporated off under vacuum. The residue is chromatographed on silica H, eluting with a toluene/MeOH (90:10; v/v) mixture. 0.018 g of the expected product is obtained after trituration in ether, m.p. 164–166° C.

EXAMPLE 63

2-[5-(2,6-Dimethoxyphenyl)-1-[4-[N-methyl-N-(2-carboxyethyl)carbamoyl]-2-isopropylphenyl]-3-pyrazolylcarbonylamino]-2-adamantanecarboxylic acid.

(I: $R_1$=4-CONMe(CH$_2$)$_2$CO$_2$H; $R_2$=2-iPr; $R_3$=H; $R_4$=CH$_3$; AA(OH)=2-carboxy-2-adamantyl).

A mixture of 0.4 g of the compound obtained in EXAMPLE 60 and 0.042 ml of 4-methoxybenzyl alcohol in 3 ml of DCM is cooled to 0° C., a stream of HCl gas is bubbled through it for 30 minutes, and the reaction mixture is diluted by adding 17 ml of DCM and left stirring for 2 hours at 0° C. It is concentrated under vacuum, the intermediate imidate obtained is taken up in 9 ml of acetone, 2 ml of 1.2N HCl are added and the mixture is left stirring for 5 days at RT. 6 ml of DMF and 1 ml of 1.2N HCl are added, and the mixture is heated to reflux for 3 days and left stirring for 72 hours at RT. It is concentrated under vacuum, the residue is taken up with DCM, the organic phase is extracted with saturated NaHCO$_3$ solution, the aqueous phase is washed with DCM, acidified to pH 1 by adding concentrated HCl solution and extracted with DCM, the organic phase is dried over MgSO$_4$ and the solvent is evaporated off under vacuum. 0.03 g of the expected product is obtained after trituration in ether followed by drying at 60° C. over P$_2$O$_5$, m.p.=166–168° C.

NMR (DMSO+TFA): 1:d:6H; 1.5–1.9:u.c.:12H; 1.9–2.8:u.c.:5H; 2.8–3.0:mt:3H; 3.2–3.6:mt:2H; 3.65:s:6H; 6.6:d:2H; 6.7:s:1H; 7.0–7.5:u.c.:4H.

EXAMPLE 64

2-[5-(2,6-Dimethoxyphenyl)-1-[4-[N-(2-propenyl)carbamoyl]-2-isopropylphenyl]-3-pyrazolylcarbonylamino]-2-adamantanecarboxylic acid.

(I: $R_1$=4-CONHCH$_2$CH=CH$_2$; $R_2$=2-iPr; $R_3$=H; $R_4$=CH$_3$; AA(OH)=2-carboxy-2-adamantyl).

This compound is prepared according to the procedure described in EXAMPLE 53, from 1.49 g of the compound obtained in Preparation 4.42 and 25 ml of SOCl$_2$, followed by 0.65 g of compound B and 1.6 ml of bis(trimethylsilyl) acetamide in 10 ml of acetonitrile. After stirring overnight at RT, some insoluble matter is filtered off and the filtrate is concentrated under vacuum. The residue is taken up in 10 ml of MeOH, 10 ml of water are added, and the solid product is drained and washed with MeOH. The solid product is taken up in acetonitrile, the mixture is heated to reflux and allowed to cool to RT, and the precipitate is drained and dried over P$_2$O$_5$. 1.6 g of the expected product are obtained, m.p.=304° C.

NMR: 1.1:d:6H; 1.5–2.2:u.c.:12H; 2.5:bs:2H; 2.65:qt:1H; 3.65:s:6H; 3.9:t:2H; 5.0–5.2::u.c.:2H; 5.8–6.0:u.c.:1H; 6.6:d:2H; 6.7:s:1H; 7.1–7.4:u.c.:3H; 7.6:d:1H; 7.85::s:1H; 8.7:t:1H.

EXAMPLE 65

2-[5-(2,6-Dimethoxyphenyl)-1-[4-[N-methyl-N-(3-trimethylammoniopropyl)carbamoyl]-2-isopropylphenyl]-3-pyrazolylcarbonylamino]-2-adamantanecarboxylic acid iodide.

(I: $R_1$=4-CONMe(CH$_2$)$_3$$^\oplus$NMe$_3$, I$^\ominus$, $R_2$=2-iPr, $R_3$=H $R_4$=CH$_3$,
AA(OH)=2-carboxy-2-adamantyl).

A mixture of 0.1 g of the compound obtained in EXAMPLE 1' and 0.04 g of methyl iodide in 6 ml of DCM is left stirring for 24 hours at RT. It is concentrated under vacuum, the residue is triturated in ether and the precipitate formed is drained. 0.12 g of the expected product is obtained, m.p.=222° C.

NMR (DMSO+TFA): 1.05:d:6H; 1.5–2.3:u.c.:14H; 2.5:bs:2H; 2.7:qt:1H; 2.75–3.7:u.c.:22H; 6.6:d:2H; 6.7:s:1H; 7.1–7.5:u.c.:4H.

EXAMPLE 66

2-[5-(2,6-Dimethoxyphenyl)-1-[4-[N-methyl-N-[3-[N'-methyl-N'-(tert-butoxycarbonyl)amino]propyl]carbamoyl]-2-isopropylphenyl]-3-pyrazolylcarbonylamino]-2-adamantanecarboxylic acid.

(I: $R_1$=4-CONMe($CH_2$)$_3$N(Me)COOtBu; $R_2$=2-iPr; $R_3$=H; $R_4$=$CH_3$; AA(OH)=2-carboxy-2-adamantyl).

A solution of 1.17 g of the compound obtained in Preparation 4.43 and 0.3 ml of triethylamine in 3 ml of DMF is cooled to –10° C., 0.21 ml of ethyl chloroformate is added under a nitrogen atmosphere and the mixture is left stirring for 15 minutes at –10° C. Separately, a mixture of 0.77 g of compound B and 2 ml of bis(trimethylsilyl)acetamide in 3 ml of DMF is heated at 80° C. for 45 minutes. After cooling to RT, this solution is added to the solution of mixed anhydride prepared above, and the mixture is left stirring for 3 days at RT. Some insoluble matter is filtered off and the filtrate is concentrated under vacuum. The residue is taken up with 32 ml of MeOH, 32 ml of water are added gradually and the mixture is concentrated under vacuum. The residue is taken up with water, and the crystallized product formed is drained, washed with water and dried. The crystals are taken up with DCM, some insoluble matter is filtered off and the filtrate is chromatographed on silica, eluting with a DCM/MeOH mixture from (100:0.5; v/v) to (100:2.5; v/v). 1 g of the expected product is obtained after trituration in pentane, m.p.=118–120° C.

EXAMPLE 67

2-[5-(2,6-Dimethoxyphenyl)-1-[4-[N-methyl-N-(3-methylaminopropyl)carbamoyl]-2-isopropylphenyl]-3-pyrazolylcarbonylamino]-2-adamantanecarboxylic acid hydrochloride.

(I: $R_1$=4-CONMe($CH_2$)$_3$NHMe; $R_2$=2-iPr; $R_3$=H; $R_4$=Me; AA(OH)=2-carboxy-2-adamantyl).

A mixture of 0.6 g of the compound obtained in EXAMPLE 66 and 4.2 ml of concentrated HCl solution in 2.7 ml of MeOH and 1.8 ml of water is left stirring for 20 minutes at RT. EtOH is added and the reaction mixture is concentrated under vacuum. The residue is taken up with EtOH and the solvent is evaporated off under vacuum. The residue is taken up with ether, and the precipitate formed is drained and washed with ether. 0.51 g of the expected product is obtained after drying under vacuum at 60° C., m.p.=240° C.

NMR (DMSO+TFA) 1.1:d:6H; 1.5–2.4:u.c.:14H; 2.6:d:3H; 2.7:mt:1H; 2.8–3.6:u.c.+s:7H; 3.65:s:6H; 6.6:d:2H; 6.7:s:1H; 7.1–7.45:u.c.:4H.

EXAMPLE 68

2-[5-(2,6-Dimethoxyphenyl)-1-[4-(4-methylphenylsulphonylamino)-2-isopropylphenyl]-3-pyrazolylcarbonylamino]-2-adamantanecarboxylic acid.

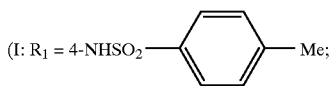

(I: $R_1$ = 4-NHSO$_2$—⟨phenyl⟩—Me;

$R_2$ = 2iPr; $R_3$ = H; $R_4$ = Me;

A(OH)=2-carboxy-2-adamantyl).

A mixture of 0.92 g of the compound obtained in Preparation 4.44 and 7 ml of SOCl$_2$ in 7 ml of DCM is heated for 1 hour at 40° C. It is concentrated under vacuum, and the acid chloride thereby obtained is used without further treatment. Separately, a mixture of 5 0.54 g of compound B and 1.35 ml of bis(trimethylsilyl)acetamide in 5 ml of acetonitrile is heated to reflux for 1 hour. After cooling to RT, this solution is added to the acid chloride prepared above, 0.25 ml of triethylamine is added and the mixture is left stirring for 2 hours at RT. It is concentrated under vacuum, the residue is taken up with 10% HCl solution, the mixture is extracted with DCM, the organic phase is dried over Na$_2$SO$_4$ and the solvent is evaporated off under vacuum. The residue is chromatographed on silica H, eluting with a DCM/MeOH/H$_2$O (100:3:0.5; v/v/v) mixture. 0.9 g of the expected product is obtained.

NMR (DMSO+TFA): 0.85:d:6H; 1.52–2.25:u.c.:12H; 2.34:s:3H; 2.45–2.06:u.c.:3H; 3.55:s:6H; 6.55:d:2H; 6.65:s:1H; 6.84:dd:1H; 6.95–7.05:u.c.:2H; 7.23–7.36:u.c.:3H; 7.58:d:2H.

EXAMPLE 69

2-[5-(2,6-Dimethoxyphenyl)-1-[4-[3-(diethylamino)propanoylamino]-2-isopropylphenyl]-3-pyrazolylcarbonylamino]-2-adamantanecarboxylic acid.

(I: $R_1$=4-NHCO($CH_2$)$_2$NEt$_2$; $R_2$=2-iPr; $R_3$=H; $R_4$=Me; AA(OH)=2-carboxy-2-adamatyl).

This compound is prepared according to the procedure described in EXAMPLE 68, from 0.27 g of the compound obtained in Preparation 4.46 in 5 ml of SOCl$_2$ and 5 ml of DCM on the one hand, and on the other hand 0.155 g of compound B and 0.39 ml of bis(trimethylsilyl)acetamide in 2 ml of acetonitrile and 0.14 ml of triethylamine. 0.13 g of the expected product is obtained, m.p.=180° C.

NMR (DMSO+TFA): 1.05:d:6H; 1.25:t:6H; 1.55–2.22:u.c.:12H; 2.5–2.72:u.c.:3H; 2.85:t:2H; 3.2:qr:4H; 3.4:mt:2H; 3.68:s:6H; 6.6:d:2H; 6.72:s:1H; 7.15:d:1H; 7.25–7.5 :u.c.:2H; 7.58:d:1H.

EXAMPLE 70

2-[5-(2,6-Dimethoxyphenyl)-1-[4-[N-acetyl-N-(3-diethylaminopropyl)amino]-2-isopropylphenyl]-3-pyrazolylcarbonylamino]-2-adamantanecarboxylic acid.

(I: $R_1$=4-N(COMe)($CH_2$)$_3$NEt$_2$; $R_2$=2-iPr; $R_3$=H; $R_4$=Me; AA(OH)=2-carboxy-2-adamantyl).

This compound is prepared according to the procedure described in EXAMPLE 68, from 0.38 g of the compound obtained in Preparation 4.48 and 3 ml of SOCl$_2$ in 3 ml of DCM, followed by 0.164 g of compound B and 0.36 ml of bis(trimethylsilyl)acetamide in 2 ml of acetonitrile and 0.075 ml of triethylamine. 0.24 g of the expected product is obtained, m.p.=220° C.

NMR (DMSO+TFA): 1.0:d:6H; 1.5:t:6H; 1.45–2.2:u.c.:17H; 2.5–2.72:u.c.:3H; 2.9–3.15:u.c.:6H; 3.6:s:6H; 3.7:t:2H; 6.59:d:2H; 6.74:s:1H; 7.15–7.42:u.c.:5H.

EXAMPLE 71

2-[5-(2,6-Dimethoxyphenyl)-1-(4-[(3-diethylaminopropyl)amino]-2-isopropylphenyl]-3-pyrazolylcarbonylamino]-2-adamantanecarboxylic acid.

(I: $R_1$=4-NH(CH$_2$)$_3$NEt$_2$; $R_2$=2-iPr; $R_3$=H; $R_4$=Me; AA(OH)=2-carboxy-2-adamantyl).

A mixture of 0.2 g of the compound obtained in EXAMPLE 70 and 1 ml of concentrated HCl in 5 ml of water and 5 ml of EtOH is heated to reflux for 16 hours. Water is added, the pH is adjusted to 5 by adding 10% NaOH and the precipitate is drained. 0.145 g of the expected product is obtained, m.p.=180° C.

NMR (DMSO+TFA): 1.05:d:6H; 1.19:t:6H; 1.4–2.2:u.c.:14H; 2.4–2.63:u.c.:3H; 2.98–3.3:u.c.:8H; 3.62:s:6H; 6.5–6.85:u.c.:5H; 7.05:d:1H; 7.3:t:1H.

EXAMPLE 72

2-[5-[2-(Cyclopropylmethyloxy)-6-methoxyphenyl]-1-[4-[N-methyl-N-(3-dimethylaminopropyl)carbamoyl]-2-isopropylphenyl]-3-pyrazolylcarbonylamino]-2-adamantanecarboxylic acid hydrochloride.

(I : $R_1$= 4-CONMe(CH$_2$)$_3$NME$_2$; $R_2$ = 2-iPr; $R_3$ = H;

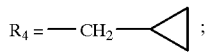

AA(OH)=2-carboxy-2-adamantyl).

A mixture of 3.87 g of the compound obtained in Preparation 4.49 and 2.4 ml of SOCl$_2$ in 50 ml of DCM is heated at 60° C. for 8 hours. It is concentrated under vacuum, the residue is taken up with toluene and the solvent is evaporated off under vacuum. The acid chloride thereby obtained is used without further treatment. Separately, a mixture of 1.27 g of compound B and 2.65 g of bis(trimethylsilyl) acetamide in 80 ml of acetonitrile is heated at 80° C. for 3 hours. A solution of the acid chloride prepared above in 80 ml of acetonitrile is then added and the mixture is heated at 60° C. for 3 hours. Some insoluble matter is filtered off and the filtrate is concentrated under vacuum. The residue is taken up in 16 ml of MeOH, 16 ml of water is added and the mixture is concentrated under vacuum. The residue is taken up with water, the mixture is extracted with DCM, the organic phase is dried over Na$_2$SO$_4$ and the solvent is evaporated off under vacuum. The residue is chromatographed on silica H, eluting with a DCM/MeOH/H$_2$O (100:5:0.5; v/v/v) mixture. 2.1 g of the expected product are obtained.

EXAMPLE 73

2-[5-(2-Hydroxy-6-methoxyphenyl)-1-[4-[N-methyl-N-(3-dimethylaminopropyl)carbamoyl]-2-isopropylphenyl]-3-pyrazolylcarbonylamino]-2-adamantanecarboxylic acid hydrochloride.

(I: $R_1$=4-CONMe(CH$_2$)$_3$NMe$_2$; $R_2$=2-iPr; $R_3$=H; $R_4$=H; AA(OH)=2-carboxy-2-adamantyl).

A mixture of 1 g of the compound obtained in EXAMPLE 72 and 20 ml of MeOH and 20 ml of HCl is heated at 60° C. for 5 hours. It is concentrated under vacuum, the residue is taken up with toluene and the mixture is concentrated under vacuum. The residue is chromatographed on silica H, eluting with a DCM/MeOH (90:10; v/v) mixture and then with a DCM/MeOH/NH$_4$OH (80:20:2; v/v/v) mixture. 0.6 g of the expected product is obtained, m.p. >250° C.

EXAMPLE 74

2-[5-(2,6-Dimethoxyphenyl)-1-[4-[3-(diethylaminopropanoyl)amino]-2-methylphenyl]-3-pyrazolylcarbonylamino]-2-adamantanecarboxylic acid.

(I: $R_1$=4-NHCO(CH$_2$)$_2$NEt$_2$; $R_2$=2-Me; $R_3$=H; $R_4$=Me; AA(OH)=2-carboxy-2-adamantyl).

A) 2-[5-(2,6-Dimethoxyphenyl)-1-(2-methyl-4-nitrophenyl)-3-pyrazolylcarbonylamino]-2-adamantanecarboxylic acid.

This compound is prepared according to the procedure described in EXAMPLE 68, from 3.2 g of the compound obtained in Preparation 4.50 and 20 ml of SOCl$_2$ in 40 ml of DCM, followed by 2.4 g of compound B and 6 ml of bis(trimethylsilyl)acetamide in 15 ml of acetonitrile and then 1.1 ml of triethylamine. After stirring overnight at RT, the mixture is concentrated under vacuum, the residue is taken up in an acetone/water mixture, and the precipitate formed is drained and dried. The precipitate is chromatographed on silica H, eluting with a DCM/MeOH/H$_2$O (100:3:0.2; v/v/v) mixture. 4.3 g of the expected product are obtained, m.p.=150° C.

NMR: 1.6–2.2:u.c.:12H; 2.25:s:3H; 2.62:mt:2H; 3.63:s:6H; 6.68:d:2H; 6.88:s:1H; 7.03–7.43:u.c.:2H; 7.58:s:1H; 8.05:dd:1H; 8.28:d:1H; 12.4:bs:1H.

B) 2-[5-(2,6-Dimethoxyphenyl)-1-(4-amino-2-methylphenyl)-3-pyrazolylcarbonylamino]-2-adamantanecarboxylic acid.

A mixture of 4.2 g of the compound obtained in the preceding step and 0.5 g of Raney® nickel in 40 ml of MeOH and 2 ml of DMF is hydrogenated for 4 hours at RT and at atmospheric pressure. The catalyst is filtered off and the filtrate is concentrated under vacuum. The residue is taken up with ether and the precipitate formed is drained. 3.37 g of the expected product are obtained, m.p.=205° C.

NMR: 1.42–2.1:u.c.:15H; 2.52:mt:2H; 3.57:s:6H; 5.1:bs:2H; 6.1:dd:1H; 6.22:d:1H; 6.42–6.68:u.c.:4H; 7.17–7.25:u.c.:2H.

C) 2-[5-(2,6-Dimethoxyphenyl)-1-[4-[3-(diethylaminopropanoyl)amino]-2-methylphenyl]-3-pyrazolylcarbonylamino]-2-adamantanecarboxylic acid.

A mixture of 0.3 ml of 3-diethylaminopropanoic acid hydrochloride and 3 ml of SOCl$_2$ in 6 ml of DCM is heated at 35° C. for 45 minutes and then concentrated under vacuum. The acid chloride thereby obtained is added to a solution of 0.87 g of the compound obtained in the preceding step and 0.157 ml of triethylamine in 5 ml of DCM. The mixture is concentrated under vacuum and the residue is chromatographed on silica H, eluting with a DCM/MeOH/H$_2$O (100:5:0.5; v/v/v) mixture. 0.5 g of the expected product is obtained, m.p.=190° C.

NMR: 1.28:t:6H; 1.6–2.22:u.c.:15H; 2.5–3.2:u.c.:10H; 3.6:s:6H; 6.63:d:2H; 6.75:s:1H; 7.05:d:1H; 7.28–7.48:u.c.:3H; 7.55:d:1H; 10.18:s:1H.

EXAMPLE 75

2-[5-(2,6-Dimethoxyphenyl)-1-[4-[[3-(1-piperidyl)propanoyl]amino]-2-methylphenyl]-3-pyrazolylcarbonylamino]-2-adamantanecarboxylic acid.

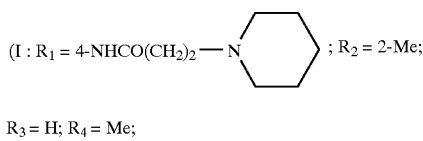

(I : R₁ = 4-NHCO(CH₂)₂—N⟨hexyl⟩ ; R₂ = 2-Me;

R₃ = H; R₄ = Me;

AA(OH)=2-carboxy-2-adamantyl).

This compound is prepared according to the procedure described in EXAMPLE 74, step C, from 0.1 g of 3-(1-piperidyl)propanoic acid and 1 ml of SOCl₂ in 2 ml of DCM, followed by 0.337 g of the compound obtained in step B of EXAMPLE 74 and 0.17 ml of triethylamine in 5 ml of DCM. 0.2 g of the expected product is obtained, m.p.=240° C.

NMR: 1.22–2.1:u.c.:21H; 2.22–2.38:u.c.:10H; 3.58:s:6H; 6.5:d:2H; 6.6:s:1H; 6.9:d:1H; 7.18–7.3:u.c.:3H; 7.38:d:1H; 10.1:s:1H.

EXAMPLE 76

2-[5-(2,6-Dimethoxyphenyl)-1-[4-[3-(diethylamino) propanoylamino]-2-isobutylphenyl]-3-pyrazolylcarbonylamino]-2-adamantanecarboxylic acid.

(I: R₁=4-NHCO(CH₂)₂NEt₂; R₂=2-iBu; R₃=H; R₄=Me; AA(OH)=2-carboxy-2-adamantyl).

This compound is prepared according to the procedure described in EXAMPLE 68, from, on the one hand 0.15 g of the compound obtained in Preparation 4.52 and 2 ml of SOCl₂ in 2 ml of DCM, and on the other hand 0.084 g of compound B and 0.21 ml of bis(trimethylsilyl)acetamide in 2 ml of acetonitrile and 0.79 ml of triethylamine. 0.014 g of the expected product is obtained, m.p.=180–200° C.

NMR: 0.75:d:6H; 1.15:t:6H; 1.4–2.25:u.c.:15H; 2.5::s:2H; 2.8:t:2H; 3.1:qr:4H; 3.3:t:2H; 3.55:s:6H; 6.5:d:2H; 6.6:s:1H; 6.8–7.6:u.c.:5H; 10.3:s:1H.

EXAMPLE 77

2-[5-(2,6-Dimethoxyphenyl)-1-[4-[3-(diethylamino) propanoylamino]-2-cyclopentylphenyl]-3-pyrazolylcarbonylamino]-2-adamantanecarboxylic acid.

(I : R₁ = 4-NHCO(CH₂)₂—NEt₂;

R₂ = 2-⟨cyclopentyl⟩ ; R₃ = H; R₄ = Me;

AA(OH)=2-carboxy-2-adamantyl).

This compound is prepared according to the procedure described in EXAMPLE 68, from, on the one hand, 0.32 g of the compound obtained in Preparation 4.54 and 2 ml of SOCl₂ in 5 ml of DCM, and on the other hand 0.17 g of compound B and 0.42 ml of bis(trimethylsilyl)acetamide in 2 ml of acetonitrile and 0.154 ml of triethylamine. 0.035 g of the expected product is obtained, m.p.=175–185° C.

NMR (DMSO+TFA): 1.1–2.55:u.c.:26H; 2.5–2.75:u.c.:5H; 3.15:mt:4H; 3.35:mt:2H; 3.62:s:6H; 6.55:d:2H; 6.65:s:1H; 7.03:d:1H; 7.25:t:1H; 7.35:dd:1H; 7.55d:1H.

EXAMPLE 78

2-[5-(2,6-Dimethoxyphenyl)-1-[4-[N-(2-diethylaminoethyl)carbamoyl]-3-isopropylphenyl]-3-pyrazolylcarbonylamino]-2-adamantanecarboxylic acid hydrochloride.

(I: R₁=4-CONH(CH₂)₂NEt₂; R₂=3-iPr; R₃=H; R₄=Me; AA(OH)=2-carboxy-2-adamantyl).

A mixture of 0.36 g of the compound obtained in Preparation 4.55 and 5 ml of SOCl₂ in 15 ml of chloroform is left stirring overnight at RT. It is concentrated under vacuum, the residue is taken up with toluene and the mixture is concentrated under vacuum. The acid chloride thereby obtained is used without further treatment. Separately, a mixture of 0.123 g of compound B and 0.315 ml of bis(trimethylsilyl) acetamide in 10 ml of acetonitrile is heated to reflux for 30 minutes. This solution is added to a solution of the acid chloride prepared above in 15 ml of acetonitrile, and the mixture is heated to reflux for 3 hours. It is concentrated under vacuum, the residue is taken up in 15 ml of MeOH and 5 ml of water and the mixture is left stirring for 2 hours at RT. It is concentrated under vacuum, the residue is extracted with chloroform, the organic phase is washed with water and dried over Na₂SO₄ and the solvent is evaporated off under vacuum. 0.35 g of the expected product is obtained after crystallization in chloroform, m.p.=210° C. (dec.) (the product crystallizes with 1 mol of chloroform).

EXAMPLE 79

2-[5-(2,6-Dimethoxyphenyl)-1-[4-(2-aminoacetylamino)-5,6,7,8-tetrahydro-1-naphthyl]-3-pyrazolylcarbonylamino]-2-adamantanecarboxylic acid hydrochloride.

(I: R₁=4-NHCOCH₂NH₂; R₂, R₃=—(CH₂)₄—; R₄=Me; AA(OH)=2-carboxy-2-adamantyl).

A) 2-[5-(2,6-Dimethoxyphenyl)-1-(4-nitro-5,6,7,8-tetrahydro-1-naphthyl)-3-pyrazolylcarbonylamino]-2-adamantanecarboxylic acid.

This compound is prepared according to the procedure described in EXAMPLE 15, from 4 g of the compound obtained in Preparation 4.56 and 20 ml of SOCl₂ in 20 ml of DCM, followed by 2.74 g of compound B and 6.86 ml of bis(trimethylsilyl)acetamide in 20 ml of acetonitrile and 0.8 ml of triethylamine. After concentration under vacuum, the residue is taken up in EtOH and the precipitate formed is drained. The precipitate is taken up in MeOH, drained and washed with ether. 5.3 g of the expected product are obtained.

NMR (DMSO+TFA) :1.5–2.25:u.c.:16H; 2.42–2.65:u.c.:4H; 2.8:mt:2H; 3.6 s:6H; 6.61:d:2H; 6.75:1H; 7.06 d:1H; 7.3 t:1H; 7.4 S: 1H; 7.65 d:1H.

B) 2-[5-(2,6-Dimethoxyphenyl)-1-(4-amino-5,6,7,8-tetra-hydro-1-naphthyl)-3-pyrazolylcarbonylamino]-2-adamantanecarboxylic acid.

A mixture of 3 g of the compound obtained in the preceding step and 0.5 g of Raney® nickel in 200 ml of DMF is hydrogenated at RT and at atmospheric pressure. The catalyst is filtered off and the filtrate is concentrated under vacuum. The residue is taken up with water and the precipitate formed is drained. 2.16 g of the expected product are obtained after drying.

NMR (DMSO+TFA) :1.42–2.2:u.c :16H; 2.3–2.8:u.c.:6H; 3.6:s :6H; 6.55:d:2H; 6.7:s 1H; 6.98:d:1H; 7.12: d:1H; 7.25:t:1H.

C) 2-[5-(2,6-Dimethoxyphenyl)-1-[4-[2-(tert-butoxycarbonylamino)acetylamino]-5,6,7,8-tetrahydro-1-naphthyl)-3-pyrazolylcarbonylamino]-2-adamantanecarboxylic acid.

A mixture of 0.3 g of the compound obtained in the preceding step and 0.258 ml of bis(trimethylsilyl)acetamide in 2 ml of toluene is heated for 1 hour at 60° C. After cooling to RT, 0.64 ml of Boc-glycine N-carboxy anhydride and 0.006 ml of N-methylmorpholine Are added and the mixture is left stirring overnight at RT. A pH 4 buffer solution is added, the mixture is extracted with AcOEt, the organic phase is dried over $Na_2SO_4$ and the solvent is evaporated off under vacuum. The residue is chromatographed on silica H, eluting with a DCM/MeOH mixture from (100:1; v/v) to (100:5; v/v). 0.14 g of the expected product is obtained.

NMR (DMSO+TFA) :1.32:s:9H; 1.45–2.12: u.c.:16H; 2.35–2.6:u.c.:6H; 3.55:s:6H; 3.65: s:2H; 6.5:d:2H; 6.62:s:1H; 6.83:d:1H; 7.13–7.3:u.c.:3H.

D) 2-[5-(2,6-Dimethoxyphenyl)-1-[4-(2-aminoacetylamino)-5,6,7,8-tetrahydro-1-naphthyl]-3-pyrazolylcarbonylamino]-2-adamantanecarboxylic acid hydrochloride.

A mixture of 0.14 g of the compound obtained in the preceding step and 5 ml of concentrated HCl in 5 ml of MeOH is left stirring for 30 minutes at RT. Water is added, and the precipitate formed is drained and dried. 0.06 g of the expected product is obtained, m.p. 220° C.

NMR: 1.59–2.5:u.c.:16H; 2.42–2.75:u.c.:6H; 3.7:s:6H; 3.88:mt:2H; 6.68:d:2H; 6.75: s:1H; 6.95:d:1H; 7.2–7.48:u.c.:3H; 8.2: mt:1H; 9.85:s:1H; 12.4:bs:1H.

EXAMPLE 80

2-[5-(2,6-Dimethoxyphenyl)-1-[4-[(3-diethylaminopropanoyl)amino]-5,6,7,8-tetrahydro-1-naphthyl]-3-pyrazolylcarbonylamino]-2-adamantanecarboxylic acid hydrochloride.

(I: $R_1$=4-NHCO$(CH_2)_2$NEt$_2$; $R_2$, $R_3$=—$(CH_2)_4$—; $R_4$=Me; AA(OH)=2-carboxy-2-adamantyl).

A mixture of 0.16 g of 3-diethylaminopropanoic acid hydrochloride and 2 ml of SOCl$_2$ in 2 ml of DCM is heated at 40° C. for 1 hour. It is concentrated under vacuum, the residue is taken up with DCM and the mixture is added at RT to a solution of 0.5 g of the compound obtained in step B of EXAMPLE 79 and 0.124 ml of triethylamine in 3 ml of DCM. After stirring over-night at RT, water is added, the mixture is extracted with DCM, the organic phases are dried over MgSO$_4$ and the solvent is evaporated off under vacuum. The residue is chromatographed on silica H, eluting with a DCM/MeOH (100:3; v/v) mixture; 0.11 g of the expected product is obtained.

NMR (DMSO+TFA) :1.21:t:6H; 1.41–2.2: u.c.:16H; 2.35–2.7:u.c.:6H; 2.84:t:2H; 3.01–3.12:u.c.:4H; 3.35:t:2H; 3.6:s:6H; 6.55:d :2H; 6.7:s:1H; 6.9:d:1H; 7.12–7.3:u.c.:2H.

EXAMPLE 81

2-[5-(2,6-Dimethoxyphenyl)-1-[4-(2-aminoethylsulphonylamino)-5,6,7,8-tetrahydro-1-naphthyl]-3-pyrazolylcarbonylamino]-2-adamantanecarboxylic acid chloride.

(I: $R_1$=4-NHSO$_2$(CH$_2$)$_2$NH$_2$; $R_2$, $R_3$=—(CH$_2$)$_4$—; $R_4$=Me; AA(OH)=2-carboxy-2-adamantyl).

A) 2-Phthalimidoethanesulphonic acid potassium salt.

This compound and the one of step B are prepared according to J. Am. Chem. Soc., 1947, 69, 1393–1401.

A mixture containing 30 g of taurine, 25 g of potassium acetate and 90 ml of acetic acid is brought to reflux for 10 minutes and 37.8 g of phthalic anhydride are then added. The mixture is heated to reflux for two and a half hours and then filtered, and the product is washed with AcOH and then with 2-propanol; it is rinsed with ether and then dried under vacuum to obtain 59.14 g of the expected product.

B) 2-Phthalimidoethanesulphonyl chloride.

60 g of the compound obtained in step A in 300 ml of toluene are heated to reflux for 1 hour in the presence of 30.7 g of phosphorus pentachloride. 30.7 g of phosphorus pentachloride are added again and refluxing is maintained for 90 minutes. 280 g of ice are added to the reaction medium, the mixture is stirred, and the insoluble matter is filtered off and then washed with ice-cold water. The residue is dried over $P_2O_5$ and then recrystallized in dichloroethane to obtain 32 g of the expected product, m.p. =160° C.

C) 2-[5-(2,6-Dimethoxyphenyl)-1-[4-(2-phthalimidoethylsulphonyl)-5,6,7,8-tetrahydro-1-naphthyl]-3-pyrazolylcarbonylamino]-2-adamantanecarboxylic acid.

A mixture containing 0.5 g of the compound obtained in EXAMPLE 79, step B, 0.43 ml of bis(trimethylsilyl)acetamide and 5 ml of acetonitrile is left stirring at 70° C. for 1 hour. The mixture is allowed to return to RT, and 0.63 g of the compound obtained in step B and 0.30 ml of triethylamine are then added. After 2 hours with stirring at RT, the mixture is acidified with 10% HCl solution. The mixture is filtered and the residue is then dried over $P_2O_5$ to obtain 0.9 g of the expected product in crude form. It is recrystallized in 100% EtOH and decolorized on animal charcoal in DCM. The product obtained is chromatographed on silica H, eluting with a DCM/MeOH/$H_2O$ (100:2:0.2; v/v/v) mixture to obtain 0.28 g of the expected product.

NMR (DMSO+TFA) :1.45–2.15:u.c.:16H; 2.4–2.6:u.c.:4H; 2.75:mt:2H; 3.48:s:6H; 3.95–4.15:u.c.:4H; 6.46 d:1H; 6.75 :s1H; 6.9:d:1H; 7.1–7.3:u.c.:2H; 7.7–7.85:u.c.4H.

D) 2-[5-(2,6-Dimethoxyphenyl)-1-[4-(2-aminoethylsulphonylamino)-5,6,7,8-tetrahydro-1-naphthyl]-3-pyrazolylcarbonylamino]-2-adamantanecarboxylic acid hydrochloride.

A mixture containing 0.24 g of the compound obtained in the preceding step, 2 ml of 95% EtOH and 23 μl of hydrazine hydrate is heated to reflux for 2 hours. The reaction medium is diluted with MeOH, the crystals are then filtered off and heated to reflux in water and the mixture is filtered in the heated state. The crystals obtained are dried over $P_2O_5$. They are redissolved in MeOH, ethereal hydrogen chloride is added, the mixture is evaporated to dryness and the residue is then taken up with ether and pentane. The mixture is filtered to obtain 60 mg of the expected product.

NMR (DMSO+TFA) :1.48–2.18:u.c.:16H; 2.18–2.62:u.c.:4H; 2.7:mt:2H; 3.19:mt:2H; 3.41:mt:2H; 3.62:s:6H; 6.58:d:1H; 6.7: s:1H; 6.82:d1H; 7.08: d: 1H; 7.28:t:1H; 7.39:s:1H.

EXAMPLE 82

(R)-2-Cyclohexyl-2-[5-(2,6-dimethoxyphenyl)-1-[4-[N-methyl-N-(3-dimethylaminopropyl)carbamoyl]-2-isopropylphenyl]-3-pyrazolylcarbonylamino]acetic acid.

(I: $R_1$=4-CON(Me)(CH$_2$)$_3$NMe$_2$; $R_2$=2-iPr; $R_3$=H; $R_4$=CH$_3$; AA(OH)=(R)-(α-carboxy)cyclohexylmethyl).

1.2 g of sodium hydroxide in 20.2 ml of water and 1.62 g of cyclohexyl-D-glycine trifluoroacetate are mixed. 1.58 g of acid chloride prepared in EXAMPLE 1, step A in 40 ml of anhydrous THF are added dropwise, and the mixture is left stirring for 48 hours at RT. The medium is concentrated, ice is added and the pH is adjusted to 7 by adding concentrated HCl. The mixture is filtered, and the residue is washed with water and then with pentane and dried under vacuum. The product is ground and then stirred in a water/DCM mixture. The resulting mixture is filtered, the aqueous phase is then extracted with DCM and the organic phase is dried over $Na_2SO_4$. The residue is concentrated, and the product is stirred in pentane and filtered off again. 380 mg of the expected product are obtained, m.p.=160° C.

EXAMPLE 83

(S)-2-Cyclohexyl-2-[5-(2,6-dimethoxyphenyl)-1-[4-[N-methyl-N-(3-dimethylaminopropyl)carbamoyl]-2-isopropylphenyl]-3-pyrazolylcarbonylamino]acetic acid hydrochloride.

(I: $R_1$=4-CON(Me)(CH$_2$)$_3$NMe$_2$; $R_2$=2-iPr; $R_3$=H; $R_4$=CH$_3$; AA(OH)=(S)-(α-carboxy)cyclohexylmethyl).

A mixture containing 0.57 g of (S)-cyclohexylglycine and 1.49 g of bis(trimethylsilyl)acetamide in 39 ml of acetonitrile is heated at 80° C. for 3 hours, and a solution of 1.93 g of the acid chloride prepared in EXAMPLE 1, step A, in 39 ml of acetonitrile is added dropwise. After 3 hours at 60° C., the mixture is allowed to return to RT and is then filtered, and the filtrate is concentrated. 8 ml of MeOH and 3 ml of water are added to the residue and the mixture is left stirring for 30 minutes. 5 ml of water are added and the mixture is concentrated. The oil formed is taken up in DCM, and the organic phase is washed with saturated NaCl solution, dried over $Na_2SO_4$ and concentrated. The residue is taken up in isopropyl ether and filtered to obtain 1.12 g of the expected compound, m.p.=160° C.

EXAMPLE 84

9-[5-(2,6-Dimethoxyphenyl)-1-[4-[N-methyl-N-(3-dimethylaminopropyl)carbamoyl]-2-isopropylphenyl]-3-pyrazolylcarbonylamino]bicyclo[3.3.1]nonane-9-carboxylic acid.

(I: $R_1$=4-CON(Me)(CH$_2$)$_3$NMe$_2$; $R_2$=2-iPr; $R_3$=H; $R_4$=CH$_3$; AA(OH)=9-carboxybicyclo[3.3.1]nonan-9-yl).

585 mg of 9-aminobicyclo[3.3.1]nonane-9-carboxylic acid and 1.5 ml of bis(trimethylsilyl)acetamide in 39 ml of acetonitrile are mixed, and the mixture is heated at 80° C. for 3 hours. 1 equivalent of the acid chloride prepared in EXAMPLE 1, step A in 39 ml of acetonitrile is added dropwise, and the mixture is heated at 60° C. for 3 hours. After 12 hours at RT, the insoluble matter is filtered off, the filtrate is then concentrated and the residue is stirred thereafter with 8 ml of MeOH and 8 ml of water. The mixture is concentrated again and the residue is then extracted with DCM to obtain 900 mg of the expected product, m.p.=160° C.

EXAMPLE 85

2-[5-(2,6-Dimethoxyphenyl)-1-[5-[(3-diethylaminopropanoyl)amino]-2-isopropylphenyl]-3-pyrazolylcarbonylamino]-2-adamantanecarboxylic acid.

(I: $R_1$=5-NHCO(CH$_2$)$_2$NEt$_2$; $R_2$=2-iPr; $R_3$=H; $R_4$=CH$_3$; AA(OH)=2-carboxy-2-adamantyl).

The acid chloride is prepared from 0.95 g of the compound of Preparation 4.57 in 5 ml of thionyl chloride and 15 ml of DCM by heating to reflux for 1 hour followed by evaporation.

A mixture of 0.55 g of compound B, 1.37 ml of bis (trimethylsilyl)acetamide in 5 ml of acetonitrile and the acid chloride in solution in 5 ml of DCM and 0.5 ml of triethylamine is heated to reflux for 1 hour. After 2 hours of stirring at RT, the mixture is evaporated to dryness and the residue is then stirred with 10 ml of water, the mixture is extracted with DCM, the organic phase is dried over MgSO$_4$ and evaporated to dryness and the residue is crystallized in acetone to obtain 0.55 g of the expected product.

NMR (DMSO+TFA):0.8–1.35:u.c.:12H; 1.5–2.4:u.c.:12H; 2.4–2.6:u.c.:3H; 2.8:t:2H; 3.15:qr:4H; 3.3:t:2H; 3.5:s:6H; 6.55:d 2H; 6.65:s:1H; 7.15–7.4:u.c.:3H; 7.75:d:1H.

EXAMPLE 86

Internal salt of 2-[5-(2,6-dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid.

The compound may also be prepared from the compound of EXAMPLE 61 according to the following procedure.

A mixture containing 0.2 g of the compound of EXAMPLE 61, 0.33 ml of formic acid and 0.11 ml of formaldehyde is heated at 100° C. for 30 minutes. After 2 hours at RT, 1 ml of 2N HCl is added, and DCM and methanol are then added in order to dissolve the gum formed. The solvents are evaporated off, the residue is taken up with water, and the mixture is then neutralized with 1.3N sodium hydroxide to pH 7 while cooling the medium in ice. The mixture is filtered, and the residue is rinsed with water and then dried over $P_2O_5$ to obtain 0.13 g of the expected product.

EXAMPLE 87

2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid hydrochloride.

Another method of preparation of the compound of EXAMPLE 1 is described below.

A) 2-(Benzyloxycarbonylamino)-2-adamantanecarboxylic acid.

1.015 g of 2-amino-2-adamantanecarboxylic acid and 6 ml of bis(trimethylsilyl)acetamide in 10 ml of DCM is heated to reflux for one and a half hours. 0.75 ml of benzyloxycarbonyl chloride is added and the mixture is heated at 50° C. for 15 minutes. The reaction medium is cooled to −70° C., decomposition is then effected by adding ice and the mixture is extracted with AcOEt. The organic phase is washed with water (twice) and with brine, dried over MgSo$_4$ and evaporated under vacuum. The product crystallizes in hexane; 1.164 g are obtained.

NMR (DMSO+TFA) :1.5:d:2H; 1.8:u.c.:6H; 2:t:4H; 2.4–2.5:u.c.:2H; 5:s:2H; 7.3: bs:5H.

B) 2-(Benzyloxycarbonylamino)-2-adamantanecarboxylic acid tert-butyl ester.

1.164 g of the compound of the preceding step are dissolved in 15 ml of DCM, 100 mg of hydrated paratoluenesulphonic acid are added, the mixture is then cooled to −78° C. and a solution of isobutylene in 15 ml of DCM is added. The mixture is allowed to return to RT and is stirred for 24 hours.

50 μl of concentrated sulphuric acid are added to dissolve the solid, after 5 hours the medium is cooled, saturated NaHCO$_3$ solution is then added, and the organic phase is dried over MgSO$_4$ and evaporated under vacuum. The residue is chromatographed on silica, eluting with a hexane/AcOEt (80:20; v/v) mixture, and 612 mg of the expected compound are obtained.

NMR (CDCl$_3$): 1.4:s:9H; 1.5–1.9:u.c.:H; 2:t:4H; 2.5:s:2H; 4.9:s:1H; 5.1:s:2H; 7.2–7.4:u.c.:5H.

C) 2-Amino-2-adamantanecarboxylic acid tert-butyl ester hydrochloride.

600 mg of the product of the preceding step are dissolved in 40 ml of EtOH, 150 μl of concentrated HCl and then 80 mg of Pd/C are added and the medium is then hydrogenated. After 1 hour, the catalyst is filtered off and the solvent is evaporated off to obtain 503 mg of the expected product.

NMR (CD$_3$OD): 1.6:s:9H; 1.8–2:u.c.:8H; 2–2.2:u.c.:4H; 2.4:s:2H.

D) 5-(2,6-Dimethoxyphenyl)-1-[4-[N-methyl-N-[3-[N'-methyl-N'-(benzyloxycarbonyl)amino]propyl]carbamoyl]-2-isopropylphenyl]-3-pyrazolecarboxylic acid methyl ester.

0.33 g of the compound of Preparation 3.57 is dissolved in 20 ml of methanolic hydrogen chloride. After 72 hours with stirring, the solvents are evaporated off. The hydrochloride obtained is dissolved in 5 ml of DCM, and 0.5 ml of triethylamine and 150 μl of benzyloxycarbonyl chloride are then added. After one hour, the reaction medium is concentrated under vacuum and the residue is then chromatographed on silica, eluting with a toluene/acetone (80:20 to 70:30; v/v) mixture. 252 mg of the expected product are obtained.

E) 5-(2,6-Dimethoxyphenyl)-1-[4-[N-methyl-N-[3-[N'-methyl-N'-(benzyloxycarbonyl)amino]propyl]carbamoyl]-2-isopropylphenyl]-3-pyrazolecarboxylic acid.

The compound obtained in the preceding step (252 mg) is dissolved in 2.5 ml of dioxane and 90 μl of aqueous potassium hydroxide solution (1 g/ml). After 24 hours of stirring, the medium is acidified with 1 ml of concentrated HCl. It is extracted with AcOEt, and the organic phase is then dried over MgSO$_4$ to obtain 236 mg of the expected compound.

F) 5-(2,6-Dimethoxyphenyl)-1-[4-[N-methyl-N-[3-[N'-methyl-N'-(benzyloxycarbonyl)amino]propyl]carbamoyl]-2-isopropylphenyl]-3-pyrazolylcarbonylamino]-2-adamantanecarboxylic acid tert-butyl ester.

The acid obtained in the preceding step is dissolved in 2 ml of acetonitrile, 0.5 ml of carbon tetrachloride and 158 mg of triphenylphosphine are added and the mixture is left stirring for 2 hours.

110 mg of the compound prepared in step C and 100 μl of triethylamine are added to the acid chloride thus formed. Triethylamine hydrochloride precipitates and the mixture is left stirring for 15 minutes. Water is added and the mixture is then extracted with DCM; the organic phase is dried over MgSO$_4$ and concentrated under vacuum. The residue is chromatographed on silica, eluting with a toluene/acetone (80:20; v/v) mixture to obtain 323 mg of the expected product.

G) 5-(2,6-Dimethoxyphenyl)-1-[4-[N-methyl-N-[3-[N'-methylamino]propyl]carbamoyl]-2-isopropylphenyl]-3-pyrazolylcarbonylamino]-2-adamantanecarboxylic acid tert-butyl ester hydrochloride.

A mixture containing the compound of the preceding step (323 mg), 2 mg of Pd/C and 40 μl of concentrated HCl in 15 ml of ethanol is stirred for 24 hours under a hydrogen atmosphere. The catalyst is filtered off and the filtrate is evaporated under vacuum. The medium is taken up with ether and stirred. The white precipitate formed is filtered off to give 190 mg of the expected product.

NMR (CD$_3$OD): 1.1:d:6H; 1.5:s:9H; 1.7–1.9:u.c.:8H; 2.2–2.3:u.c.:6H; 2.6:s:2H; 2.7–2.9:q+s:4H; 3:s:3H; 3.1:t:2H; 3.7: s+mt:8H; 6.6:d:2H; 6.8:s:1H; 7.2–7.6:u.c.:5H.

H) 2-[5-(2,6-Dimethoxyphenyl)-1-[4-[N-methyl-N-(3-dimethylaminopropyl)carbamoyl]-2-isopropylphenyl]-3-pyrazolylcarbonylamino]-2-adamantanecarboxylic acid hydrochloride.

The compound of the preceding step (190 mg) is suspended in 50 μl of acetonitrile, and 0.5 ml of a solution of methyl iodide in toluene (89 μl of methyl iodide in 100 ml of toluene) and 7.6 mg of silver carbonate are added. The insoluble matter is filtered off and the solvent is then evaporated off under vacuum. The medium is taken up with 2 ml of formic acid and 0.2 ml of concentrated HCl and stirred overnight. After evaporation under vacuum and trituration in ether, 90 mg of the expected product are obtained.

EXAMPLE 88

Oxazolone of the compound of EXAMPLE 1':

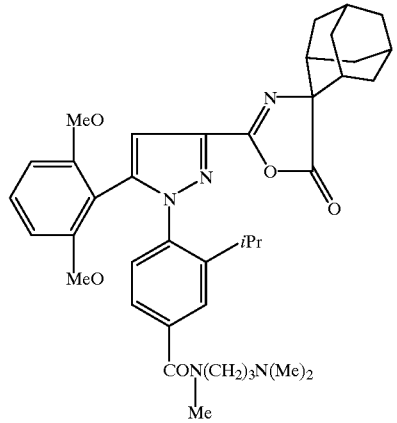

A solution of 0.23 g of the compound of EXAMPLE 1' in 2 ml of DCM and 0.5 ml of acetic anhydride is stirred for 4 hours 30 minutes. It is evaporated under vacuum, and the residue is triturated in pentane, filtered off and dried to obtain 230 mg of expected oxazolone, m.p.=129° C. (dec.). IR (KBr):1800 cm$^1$. Mass spectrum: M: 667.9.

NMR: 1:d:6H; 1.5–1.9:u.c.:8H; 2:bs: 8H; 2.1–2.5:u.c.:6H; 2.65:qt:1H; 2.9 and 3:2s: 3H; 3.1:mt 2H; 3.4:mt:2H; 3.65:s:6H; 6.6: d:2H; 6.9:s:1H; 7.1–7.4:u.c.:4H.

We claim:
1. Compound of formula:

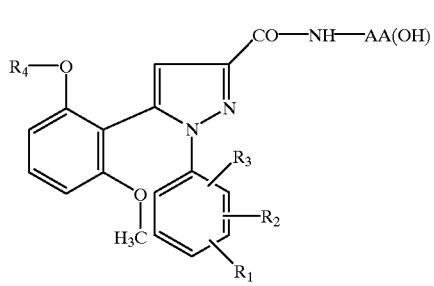

in which:

R$_1$ represents a group chosen from:
—T—CN;
—C(NH$_2$)=NOH;
—C(=NOH)NH(CH$_2$)$_r$NR$_5$R$_6$;
—T—C(NR$_{12}$R$_{13}$)=NR$_{14}$;
—C(NH$_2$)=NO(CH$_2$)$_r$NR$_5$R$_6$;
—T—CONR$_a$R$_b$;
—T—CONR$_7$R$_c$;
—Y—CO$_2$R$_7$;
—OR$_d$;

—T—$NR_5R_6$, on condition that $R_5$ and $R_6$ do not simultaneously represent hydrogen when T represents a direct bond;
—T—$N(R_7)COR_e$;
—$SO_2NR_aR_b$;
—T—$N(R_7)SO_2R'_7$;
—T—$NR_{27}R_{28}$;

—$NR_aR_b$ represents a group chosen from:
—$NR_5R_6$; —$NR_9(CH_2)_sCR_7R_8(CH_2)_tNR_5R_6$;
—$NR_{21}(CH_2)_sCR_7R_8(CH_2)_t{}^\oplus NR_{22}R_{23}R_{24}Q^\ominus$

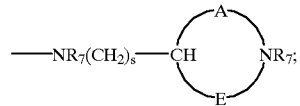

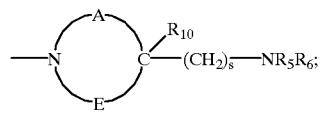

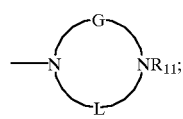

—$NR_7(CH_2)_qCN$; —$NR_7(CH_2)_qC(NR_{12}R_{13})=NR_{14}$;
—$NR_7(CH_2)_qCONH_2$; —$NR_7(CH_2)_qCO_2R_7$;
—$NR_{21}(CH_2)_sCR_7R_8(CH_2)_tNR_{25}R_{26}$;

$R_c$ represents a group chosen from:
—X—$OR_7$; —$CHR_{20}CO_2R_7$; —$(CH_2)_4CH(NH_2)CO_2R_7$;

$R_d$ represents a group chosen from:
—X—$NR_5R_6$; —Y—$CONR_5R_6$; —Y—$CO_2R_7$;
—Y—$SO_2NR_5R_6$;

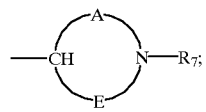

$R_e$ represents a group chosen from:
—$R_{16}$; —Y—$NR_5R_6$; —Y—$NHCOR_{16}$; —$CH(R_{17})NR_5R_6$; —Y—$^\oplus NR_{22}R_{23}R_{24}Q^\ominus$

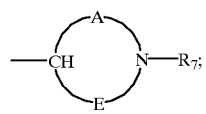

—$(CH_2)_qCN$; —$(CH_2)_qC(NR_{12}R_{13})=NR_{14}$;
—$NR_{18}R_{19}$;

$R_2$ and $R_3$ each independently represent hydrogen, a $(C_1-C_6)$alkyl, a $(C_3-C_8)$cycloalkylmethyl, a $(C_3-C_8)$cycloalkyl, a halogen, a nitro, a trifluoromethyl, a group —$OR_4$, a group —$NR_5R_6$, a 1-pyrrolyl, a cyano, a carbamoyl;

or $R_2$ and $R_3$ together constitute a trimethylene, tetramethylene or pentamethylene group;

$R_4$ represents hydrogen; a $(C_1-C_6)$alkyl; a $(C_3-C_4)$alkenyl; a $(C_3-C_8)$cycloalkyl; a $(C_3-C_8)$cycloalkylmethyl; a $(C_1-C_4)$alkoxy$(C_1-C_4)$alkylene; a benzyl;

$R_5$ and $R_6$ each independently represent a hydrogen, a $(C_1-C_6)$alkyl; a $(C_3-C_8)$alkenyl; a $(C_3-C_8)$cycloalkylmethyl; a benzyl; or $R_5$ and $R_6$, together with the nitrogen atom to which they are attached, represent a heterocycle chosen from: pyrrolidine, aziridine, and azetidine;

$R'_5$ and $R'_6$ each independently represent a hydrogen or a $(C_1-C_6)$alkyl; or alternatively, $R'_5$ and $R'_6$, together with the nitrogen atom to which they are attached, represent pyrrolidine;

$R'_7$ represents a $(C_1-C_4)$alkyl; a phenyl which is unsubstituted or substituted one or more times with a $(C_1-C_4)$alkyl; a group —X—$NR_5R_6$;

$R_7$ represents a hydrogen, a $(C_1-C_4)$alkyl or a benzyl;

$R_8$ represents a hydrogen, a $(C_1-C_4)$alkyl, a hydroxyl, or $R_7$ and $R_8$, together with the carbon atom to which they are attached, constitute a $(C_3-C_5)$cycloalkane;

$R_9$ represents hydrogen, a $(C_1-C_4)$alkyl, a benzyl, a group —X—OH or a group —X—$NR'_5R'_6$, a $(C_3-C_8)$alkenyl;

$R_{10}$ represents a hydrogen, a $(C_1-C_4)$alkyl, a benzyl, a carbamoyl, a cyano;

$R_{11}$ represents a hydrogen, a $(C_1-C_4)$alkyl, a group —X—OH, a group —X—$NR'_5R'_6$;

$R_{12}$ and $R_{13}$ each independently represent a hydrogen or a $(C_1-C_4)$alkyl;

$R_{14}$ represents hydrogen, $R_{14}$ can, in addition, represent a $(C_1-C_4)$alkyl when $R_{12}$ represents hydrogen and $R_{13}$ represents a $(C_1-C_4)$alkyl;

or $R_{13}$ and $R_{14}$ together represent a group Z;

$R_{15}$ represents hydrogen, a $(C_1-C_4)$alkyl, a group —$(CH_2)_sNR_5R_6$;

$R_{16}$ represents hydrogen, a $(C_1-C_8)$alkyl, a $(C_3-C_8)$cycloalkyl or a phenyl;

$R_{17}$ represents a $(C_1-C_6)$alkyl, a phenyl, a benzyl, a hydroxy$(C_1-C_4)$alkyl, an amino$(C_1-C_4)$alkyl;

$R_{18}$ and $R_{19}$ each independently represent a hydrogen, a $(C_1-C_4)$alkyl; $R_{18}$ can, in addition, represent a group —$(CH_2)_q$—$NR_5R_6$;

or $R_{18}$ and $R_{19}$, together with the nitrogen atom to which they are attached, represent pyrrolidine;

$R_{20}$ represents hydrogen, a $(C_1-C_4)$alkyl, a benzyl, a hydroxyphenylmethyl, a hydroxy$(C_1-C_4)$alkyl, a mercapto$(C_1-C_4)$alkyl; a —$(CH_2)_3$—NH—C(=NH)$NH_2$ group, a —$(CH_2)_4NH_2$ group, a group —$CH_2$—Im in which Im represents a 4-imidazolyl;

$R_{21}$ represents a $(C_1-C_4)$alkyl, an allyl or a benzyl;

$R_{22}$ and $R_{23}$ each independently represent a $(C_1-C_6)$alkyl; or alternatively $R_{22}$ and $R_{23}$, together with the nitrogen atom to which they are attached, represent pyrrolidine;

$R_{24}$ represents a $(C_1-C_4)$alkyl, a benzyl, an allyl, a hydroxy$(C_1-C_4)$alkyl, a $(C_1-C_4)$alkoxy$(C_1-C_4)$alkyl;

$\ominus$ represents an anion;

$R_{25}$ represents hydrogen or a $(C_1-C_6)$alkyl;

$R_{26}$ represents a $(C_1-C_4)$alkoxycarbonyl, a benzyloxycarbonyl; a $(C_1-C_4)$alkylcarbonyl;

$R_{27}$ represents a hydrogen; a $(C_1-C_4)$alkyl, a $(C_1-C_4)$alkylcarbonyl; a group —CO—$(CH_2)_r$—OH; a group $SO_2R'_7$;

$R_{28}$ represents a group —X—$NR_5R_6$;

s=0 to 3;

t=0 to 3, on the condition that (s+t), in a same group, is greater than or equal to 1;

r=2 to 5;

q=1 to 5;

T represents a direct bond or $(C_1-C_7)$alkylene;

X represents a $(C_2-C_7)$alkylene;

Y represents a $(C_1-C_7)$alkylene;

Z represents a $(C_2-C_6)$alkylene;

the bivalent radicals A and E, together with the carbon atom and the nitrogen atom to which they are attached, constitute a saturated 4- to 7-membered heterocycle which can, in addition, be substituted with one or more $(C_1-C_4)$alkyls;

the bivalent radicals G and L, together with the nitrogen atoms to which they are attached, constitute a imidazolidine or imidazoline ring, the said rings being optionally substituted on the carbon atoms with one or more $(C_1-C_4)$alkyls;

the group —NH—AA(OH) represents the residue of an amino acid:

$$-\mathrm{NH}-\underset{X_a}{\overset{X'_a}{\mathrm{C}}}-\mathrm{COOH}$$

where $X_a$ is hydrogen and $X'_a$ is hydrogen, a $(C_1-C_5)$alkyl or a non-aromatic $C_3-C_{15}$ carbocyclic radical; or alternatively, $X_a$ and $X'_a$, together with the carbon atom to which they are attached, form a non-aromatic $C_3-C_{15}$ carbocycle;

its salts and its quaternary ammonium salts formed with acyclic or cyclic tertiary amines and its solvates.

2. Compound according to claim 1 of formula (Ip):

(Ip)

[structural formula with $R_{4p}$—O, $H_3C$—O, pyrazole ring with CO—NH—AA$_p$(OH), and phenyl ring with $R_{1p}$, $R_{2p}$, $R_{3p}$]

in which:

$R_{1p}$ represents a group chosen from:
—T—CN;
—C(NH$_2$)=NOH;
—C(=NOH)NH(CH$_2$)$_r$NR$_5$R$_6$;
—T—C(NR$_{12}$R$_{13}$)=NR$_{14}$;
—C(NH$_2$)=NO(CH$_2$)$_r$NR$_5$R$_6$;
—T—CONR$_a$R$_b$;
—T—CONR$_7$R$_c$;
—Y—CO$_2$R$_7$;
—OR$_d$;
—T—NR$_5$R$_6$, on condition that R$_5$ and R$_6$ do not simultaneously represent hydrogen when T represents a direct bond;
—T—N(R$_7$)COR$_e$;
—SO$_2$NR$_a$R$_b$;
—T—N(R$_7$)SO$_2$R'$_7$;

—NR$_a$R$_b$ represents a group chosen from:
—NR$_5$R$_6$; —NR$_9$(CH$_2$)$_s$CR$_7$R$_8$(CH$_2$)$_t$NR$_5$R$_6$;

[ring structure with —NR$_7$(CH$_2$)$_8$—CH, A, E, NR$_7$]

[ring structure with N, A, E, C, $R_{10}$, (CH$_2$)$_8$—NR$_5$R$_6$]

[ring structure with N, G, L, NR$_{11}$]

—NR$_7$(CH$_2$)$_q$CN; —NR$_7$(CH$_2$)$_q$C(NR$_{12}$R$_{13}$)=NR$_{14}$;

R$_c$ represents a group chosen from:
—X—OR$_7$; —CHR$_{20}$CO$_2$R$_7$; —(CH$_2$)$_4$CH(NH$_2$)CO$_2$R$_7$;

R$_d$ represents a group chosen from:
—X—NR$_5$R$_6$; —Y—CONR$_5$R$_6$; —Y—CO$_2$R$_7$; —Y—SO$_2$NR$_5$R$_6$;

[ring structure with CH, A, E, N—R$_7$]

R$_e$ represents a group chosen from:
—R$_{16}$; —Y—NR$_5$R$_6$; —Y—NHCOR$_{16}$; —CH(R$_{17}$)NR$_5$R$_6$;

[ring structure with CH, A, E, N—R$_7$]

—(CH$_2$)$_q$CN; —(CH$_2$)$_q$C(NR$_{12}$R$_{13}$)=NR$_{14}$; —NR$_{18}$R$_{19}$;

R$_{2p}$ and R$_{3p}$ each independently represent hydrogen, a $(C_1-C_6)$alkyl, a $(C_3-C_8)$cycloalkylmethyl, a $(C_3-C_8)$cycloalkyl, a halogen, a nitro, a trifluoromethyl, a group —OR$_4$, a group —NR$_5$R$_6$, a 1-pyrrolyl, a cyano, a carbamoyl;

or R$_{2p}$ and R$_{3p}$ together constitute a trimethylene, tetramethylene or pentamethylene group;

R$_{4p}$ represents hydrogen; a $(C_1-C_6)$alkyl; a $(C_3-C_4)$alkenyl; a $(C_3-C_8)$cycloalkyl; a $(C_3-C_8)$cycloalkylmethyl; a $(C_1-C_4)$alkoxy$(C_1-C_4)$alkyl; a benzyl;

R$_5$ and R$_6$ each independently represent a hydrogen, a $(C_1-C_6)$alkyl; or R$_5$ and R$_6$, together with the nitrogen atom to which they are attached, represent pyrrolidine;

R'$_7$ represents a $(C_1-C_4)$alkyl;

R$_7$ represents a hydrogen, a $(C_1-C_4)$alkyl or a benzyl;

R$_8$ represents a hydrogen, a $(C_1-C_4)$alkyl, a hydroxyl, or R$_7$ and R$_8$, together with the carbon atom to which they are attached, constitute a $(C_3-C_5)$cycloalkane;

R$_9$ represents hydrogen, a methyl, a group —X—OH or a group —X—NR$_5$R$_6$;

R$_{10}$ represents a hydrogen, a $(C_1-C_4)$alkyl, a benzyl, a carbamoyl, a cyano;

$R_{11}$ represents a hydrogen, a $(C_1-C_4)$alkyl, a group —X—OH, a group —X—$NR_5R_6$;

$R_{12}$ and $R_{13}$ each independently represent a hydrogen or a $(C_1-C_4)$alkyl;

$R_{14}$ represents hydrogen, $R_{14}$ may, in addition, represent a $(C_1-C_4)$alkyl when $R_{12}$ represents hydrogen and $R_{13}$ represents a $(C_1-C_4)$alkyl;

or $R_{13}$ and $R_{14}$ together represent a group Z;

$R_{15}$ represents hydrogen, a $(C_1-C_4)$alkyl, a group —$(CH_2)_s$$NR_5R_6$;

$R_{16}$ represents hydrogen, a $(C_1-C_8)$alkyl, a $(C_3-C_8)$cycloalkyl, or a phenyl;

$R_{17}$ represents a $(C_1-C_6)$alkyl, a phenyl, a benzyl, a hydroxy$(C_1-C_4)$alkyl, an amino$(C_1-C_4)$alkyl;

$R_{18}$ and $R_{19}$ each independently represent a hydrogen, a $(C_1-C_4)$alkyl; $R_{18}$ can, in addition, represent a group —$(CH_2)_q$—$NR_5R_6$;

or $R_{18}$ and $R_{19}$, together with the nitrogen atom to which they are attached, represent pyrrolidine;

$R_{20}$ represents hydrogen, a $(C_1-C_4)$alkyl, a benzyl, a hydroxyphenylmethyl, a hydroxy$(C_1-C_4)$alkyl, a mercapto$(C_1-C_4)$alkyl; a —$(CH_2)_3$—NH—C(=NH)$NH_2$ group, a —$(CH_2)_4NH_2$ group, a group —$CH_2$—Im in which Im represents a 4-imidazolyl:

s=0 to 3;

t=0 to 3, on the condition that (s+t) is greater than or equal to 1;

r=2 to 5;

q=1 to 5;

T represents a direct bond or $(C_1-C_7)$alkylene;

X represents a $(C_2-C_7)$alkylene;

Y represents a $(C_1-C_7)$alkylene;

Z represents a $(C_2-C_6)$alkylene;

the bivalent radicals A and E, together with the carbon atom and the nitrogen atom to which they are attached, constitute a saturated 5- to 7-membered heterocycle which can, in addition, be substituted with one or more $(C_1-C_4)$alkyls;

the bivalent radicals G and L, together with the nitrogen atoms to which they are attached, constitute a imidazolidine or imidazoline ring, the said rings being optionally substituted on the carbon atoms with one or more $(C_1-C_4)$alkyls;

the group —NH—AAp(OH) represents the residue of an amino acid:

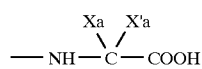

where $X_a$ is hydrogen and $X'_a$ is hydrogen, a $(C_1-C_5)$alkyl or a non-aromatic $C_3-C_{15}$ carbocyclic radical; or alternatively $X_a$ and $X'_a$, together with the carbon atom to which they are attached, form a non-aromatic $C_3-C_{15}$ carbocycle;

and its salts.

3. Compound according to claim 1 of formula:

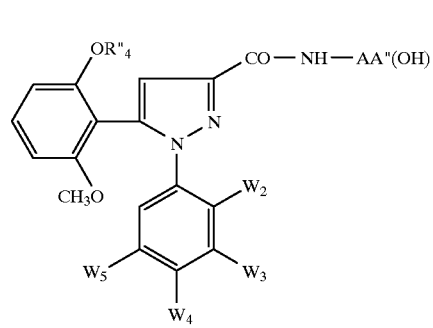

(I")

in which:

R"$_4$ represents hydrogen, a methyl or a cyclopropylmethyl;

AA"(OH) represents a 2-carboxy-2-adamantyl, α-carboxycyclohexylmethyl or 9-carboxybicyclo[3.3.1]nonan-9-yl group;

among the substituents $w_2$, $w_3$, $w_4$ and $w_5$, at least one is hydrogen and at least one other is other than hydrogen, such that:

either (i)

$w_5$ is hydrogen;

$w_3$ is hydrogen or methyl;

$w_2$ is $(C_1-C_4)$alkyl, $(C_3-C_6)$cycloalkyl, $(C_1-C_4)$alkoxy, chlorine or trifluoromethyl, or $w_2$ and $w_3$ together form a 1,4-butylene group;

$w_4$ is chosen either from the following groups:

(i25) 3-dialkylaminopyrrolidinocarbonyl

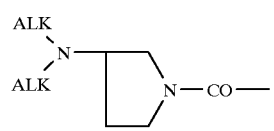

(i28) 1-alkyl-2-pyrrolidinylmethylaminocarbonyl

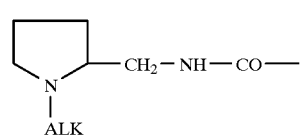

its internal salts and its pharmaceutically acceptable salts, its quaternary ammonium salts and its solvates.

4. Compound according to claim 1, of formula:

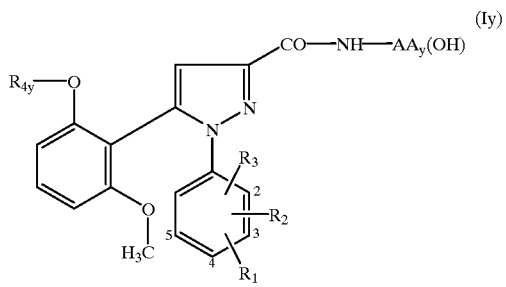

in which:

$R_1$, $R_2$ and $R_3$ are as defined for (I) in claim 1;

$R_{4y}$ represents hydrogen, a $(C_1-C_4)$alkyl group, an allyl or a cyclopropylmethyl; and the group —NH—$AA_y$—(OH) represents the residue of 2-aminoadamantane-2-carboxylic acid or of (S)-x-aminocyclohexaneacetic acid or of 9-aminobicyclo-[3.3.1]-nonane-9-carboxylic acid;

its salts and its quaternary ammonium salts formed with acyclic or cyclic tertiary amines and its solvates.

5. Compound according claim 1 of formula (Iy) in which:

$R_1$, as defined for (I) in claim 1, is at position 4 or 5;

$R_2$, is at position 2 and represents a group chosen from: hydrogen, a $(C_1-C_6)$alkyl, a $(C_3-C_8)$cycloalkyl, a $(C_3-C_8)$cycloalkylmethyl, a $(C_1-C_6)$alkoxy, a $(C_3-C_8)$ cycloalkyloxy, a chlorine, a trifluoromethyl;

$R_3$ is at position 3 and represents hydrogen, a $(C_1-C_6)$ alkyl, a $(C_3-C_8)$ cycloalkyl, a $(C_3-C_8)$ cycloalkylmethyl;

or $R_2$ and $R_3$ together constitute a trimethylene, a tetramethylene or a pentamethylene;

its salts and its quaternary ammonium salts formed with acyclic or cyclic tertiary amines and its solvates.

6. Compound according to claim 1 of formula:

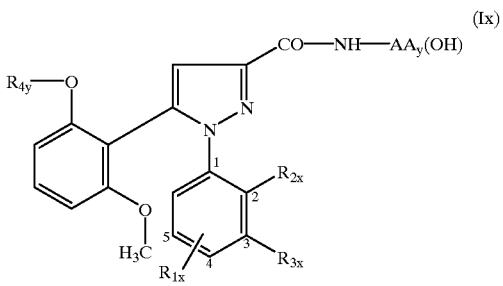

in which:

$R_{4y}$ and NH—$AA_y$(OH) are as defined for (Iy) in claim 4;

$R_{1x}$ is at position 4 or 5 and represents a group chosen from —T—$CONR_aR_b$, —$SO_2NR_aR_b$, —T—$NR_5R_6$, —$N(R_7)COR_e$, —$OR_d$, —$N(R_7)SO_2R'_7$, —T—$NR_{27}R_{28}$; the groups —T—, $R_a$, $R_b$, $R_d$, $R_e$, $R_5$, $R_6$, $R_7$, $R'_7$, $R_{27}$ and $R_{28}$ being as defined for (I) in claim 1;

$R_{2x}$ and $R_{3x}$ each independently represent hydrogen; a $(C_1-C_6)$alkyl; a $(C_3-C_8)$cycloalkyl; a $(C_3-C_8)$ cycloalkylmethyl;

on condition that $R_{2x}$ and $R_{3x}$ do not simultaneously represent hydrogen;

or $R_{2x}$ and $R_{3x}$ together constitute a tetramethylene group;

its salts and its quaternary ammonium salts formed with acyclic or cyclic tertiary amines and its solvates.

7. Compound according to claim 1 of formula:

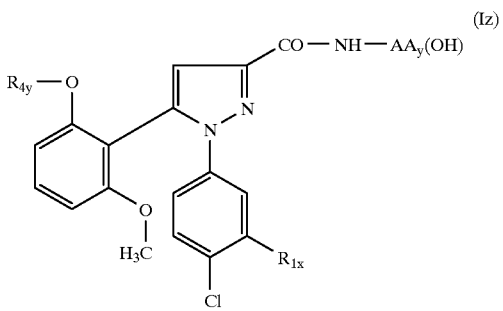

in which $R_{4y}$, $R_{1x}$ and NH—$AA_y$(OH) are as defined in claims 4 and 6; its salts and its quaternary ammonium salts formed with acyclic or cyclic tertiary amines.

8. Compound of formula:

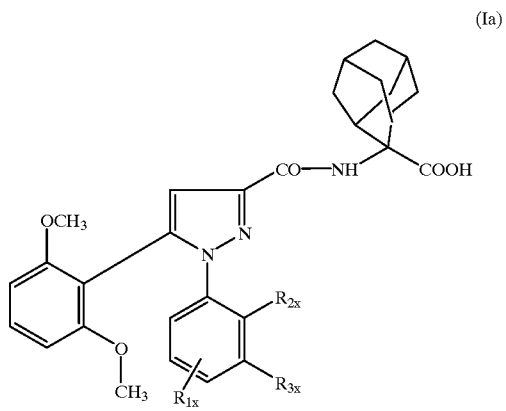

in which:

$R_{1x}$, $R_{2x}$ and $R_{3x}$ are as defined for (Ix) in claim 6;

its salts and its quaternary ammonium salts formed with acyclic or cyclic tertiary amines and its solvates.

9. A pharmaceutical composition, comprising as an active ingredient, the compound according to claim 1 or one of its pharmaceutically acceptable salts, in combination with a pharmaceutically acceptable vehicle.

10. Compound according to claim 4 of formula (Iy) in which:

$R_1$, as defined for (I) in claim 1, is at position 4 or 5;

$R_2$, is at position 2 and represents a group chosen from: hydrogen, a $(C_1-C_6)$alkyl, a $(C_3-C_8)$cycloalkyl, a $(C_3-C_8)$cycloalkylmethyl, a $(C_1-C_6)$alkoxy, a $(C_3-C_8)$ cycloalkyloxy, a chlorine, a trifluoromethyl;

$R_3$ is at position 3 and represents hydrogen, a $(C_1-C_6)$ alkyl, a $(C_3-C_8)$ cycloalkyl, a $(C_3-C_8)$ cycloalkylmethyl;

or $R_2$ and $R_3$ together constitute a trimethylene, a tetramethylene or a pentamethylene;

its salts and its quaternary ammonium salts formed with acyclic or cyclic tertiary amines and its solvates.

11. Compound according to claim 4 of formula:

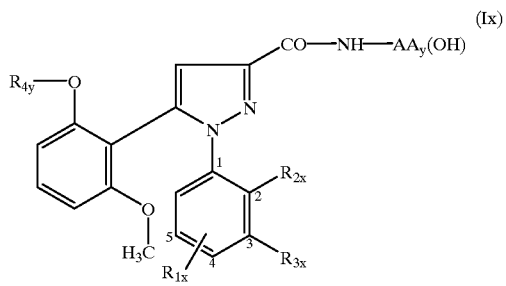

(Ix)

in which:

$R_{4y}$ and NH—$AA_y$(OH) are as defined for (Iy) in claim 4;

$R_{1x}$ is at position 4 or 5 and represents a group chosen from —T—$CONR_aR_b$, —$SO_2NR_aR_b$, —T—$NR_5R_6$, —N($R_7$)$COR_e$, —$OR_d$, —N($R_7$)$SO_2R'_7$, —T—$NR_{27}R_{28}$; the groups —T—, $R_a$, $R_b$, $R_d$, $R_e$, $R_5$, $R_6$, $R_7$, $R'_7$, $R_{27}$ and $R_{28}$ being as defined for (I) in claim 1;

$R_{2x}$ and $R_{3x}$ each independently represent hydrogen; a ($C_1$–$C_6$)alkyl; a ($C_3$–$C_8$)cycloalkyl; a ($C_3$–$C_8$) cycloalkylmethyl;

on condition that $R_{2x}$ and $R_{3x}$ do not simultaneously represent hydrogen;

or $R_{2x}$ and $R_{3x}$ together constitute a tetramethylene group; its salts and its quaternary ammonium salts formed with acyclic or cyclic tertiary amines and its solvates.

12. The compound of claim 1 which is 2-[5-(2,6-Dimethoxyphenyl)-1-[4-[1-pyrrolidinylethyl)carbamoyl]-2-isopropylphenyl]-3-pyrazolylcarbonylamino]-2-adamantanecarboxylic acid, and its pharmaceutically acceptable salts.

13. The compound of claim 1 which is 2-[5-(2,6-Dimethoxyphenyl)-1-[4-[N-(1-ethyl-2-pyrrolidinylmethyl) carbamoyl]-2-isopropylphenyl]-3-pyrazolylcarbonylamino]-2-adamantanecarboxylic acid, and its pharmaceutically acceptable salts.

14. The compound of claim 1 which is 2-[5-(2,6-Dimethoxyphenyl)-1-[4-[[3-(diethyl-amino)-1-pyrrolidiny] carbamoyl]-2-isopropylphenyl]-3-pyrazolycarbonylamino]-2-adamantanecarboxylic acid, and its pharmaceutically acceptable salts.

* * * * *